(12) United States Patent
Scanlan et al.

(10) Patent No.: US 8,236,987 B2
(45) Date of Patent: Aug. 7, 2012

(54) SELECTIVE ESTROGEN RECEPTOR MODULATOR COMPOSITIONS AND METHODS FOR TREATMENT OF DISEASE

(75) Inventors: Thomas S. Scanlan, Portland, OR (US); Toru Iijima, Saitama (JP)

(73) Assignees: The Regents of the University of California, Oakland, CA (US); Oregon Health & Science University, Portland, OR (US)

( * ) Notice: Subject to any disclaimer, the term of this patent is extended or adjusted under 35 U.S.C. 154(b) by 528 days.

(21) Appl. No.: 11/938,129

(22) Filed: Nov. 9, 2007

(65) Prior Publication Data
US 2009/0124698 A1 May 14, 2009

(51) Int. Cl.
*C07C 233/00* (2006.01)
(52) U.S. Cl. ............ 564/207; 564/84; 564/95; 564/171; 564/192; 564/204; 514/627
(58) Field of Classification Search ................. None
See application file for complete search history.

(56) References Cited

U.S. PATENT DOCUMENTS

| 4,016,223 | A | 4/1977 | Rajadhyaksha et al. |
| 7,196,119 | B2 * | 3/2007 | Scanlan et al. ........... 514/627 |

FOREIGN PATENT DOCUMENTS

| WO | WO 2005/041946 A | 5/2005 |
| WO | WO 2007/062067 A2 | 5/2007 |

OTHER PUBLICATIONS

Qiu et al, Journal of Neuroscience (2006), 26(21), 5649-5655.*
PCT Invitation to Pay Additional Fees, PCT/US2008/082865, Mar. 23, 2009, 7 pages.
Database Caplus [Online] Chemical Abstracts Service, Columbus, OH, US; Keil, J.G. et al., "Semisynthetic coumermycins. I. Preparation of 3-acylamido-4-hydroxy-8-methyl-7-[3-0-(5-methyl-2- pyrrolylcarbonyl)noviosyloxy]coumarins," XP002527552, Retrieved from STN Database Accession No. 1969:88192.
Database Caplus [Online] Chemical Abstracts Service, Columbus, OH, US; Tripathi, S. et al., "Design and Synthesis of Some New .alpha.-Phenyl Cinnamoyl Derivatives for Selective Protection of Purine Nucleosides," XP002527553, Retrieved from STN Database Accession No. 2005:1223558.
PCT International Search Report and Written Opinion, PCT Application No. PCT/US2008/082865, Jun. 26, 2009, 21 pages.
European Examination Report, European Application No. 08847112.3, Jan. 14, 2011, 3 pages.

* cited by examiner

*Primary Examiner* — Sudhakar Katakam
(74) *Attorney, Agent, or Firm* — Fenwick & West LLP

(57) ABSTRACT

The present disclosure concerns a new class of selective estrogen receptor modulators (SERMs). The disclosure also includes the identification of a previously unknown membrane associated estrogen receptor. Methods for making and using the disclosed SERMs are disclosed, including pharmaceutical formulations of the disclosed novel compounds in useful compositions.

35 Claims, 16 Drawing Sheets

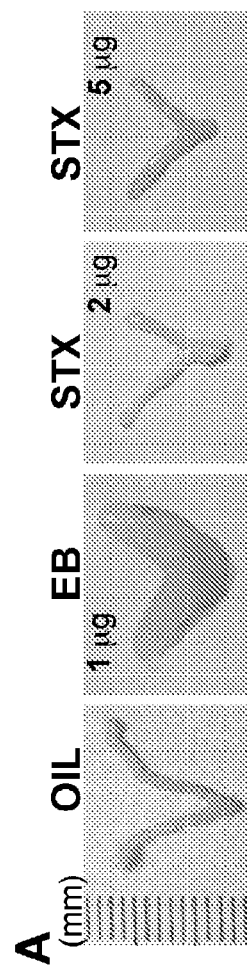
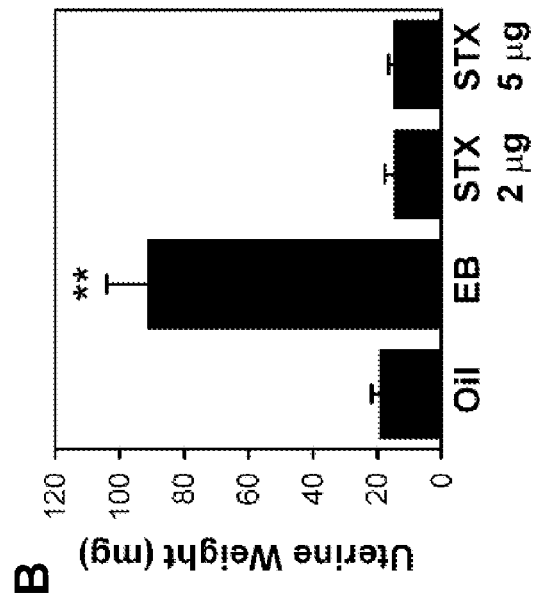
Figure 7B
Figure 7A

SEQUENCE LISTING

```
<160> NUMBER OF SEQ ID NOS: 16

<210> SEQ ID NO 1
<211> LENGTH: 11
<212> TYPE: PRT
<213> ORGANISM: Artificial Sequence
<220> FEATURE:
<223> OTHER INFORMATION: Synthetic construct

<400> SEQUENCE: 1

Leu Gly Leu Asn Leu Lys Glu Tyr Asn Leu Val
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic construct

<400> SEQUENCE: 2

Cys Arg Met His Leu Arg Gln Tyr Glu Leu Leu
1               5                   10

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 3
ggctctggtg atggaata                                                    18

<210> SEQ ID NO 4
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 4
cagaatcacg ctgtctgtt                                                   19

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 5
tccacgttat actggttcac                                                  20

<210> SEQ ID NO 6
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 6
ttgcatcact gaagctctc                                                   19

<210> SEQ ID NO 7
```

```
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
tgtttgtgcc aaagctcatc                                                  20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 8
gtgtcttgca gttgcatagt                                                  20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 9
ctggccttgc tgcttcagat                                                  20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
atggagtagg agcgcttgtc                                                  20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 11
catccactgg tgctgccaag                                                  20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 12
gtcctcggtg tagcccaaga                                                  20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 13
```

```
aaaggcagct tcgggaaggt                                              20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
tggatgtggt acatcaggtc                                              20

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 15
ctgttcggca agtttgacca g                                            21

<210> SEQ ID NO 16
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 16
tgacgccaca cagcacatt                                               19
```

SELECTIVE ESTROGEN RECEPTOR MODULATOR COMPOSITIONS AND METHODS FOR TREATMENT OF DISEASE

STATEMENT OF GOVERNMENT SUPPORT

This invention was made with government support under Grant Nos. DK-57574 from the National Institutes of Health. The United States government has certain rights in this invention.

FIELD

This disclosure concerns novel compounds and methods for their use, including selective estrogen receptor modulators and methods for making such selective estrogen receptor modulators.

BACKGROUND

Estrogens are an important class of steroidal hormones that stimulates the development and maintenance of fundamental sexual characteristics in humans. In addition, estrogens have been demonstrated to affect a variety of diverse biological processes. Many of the incidental effects of estrogens are positive, including the maintenance of bone density, central nervous system function and preservation of memory. However, estrogens also have been demonstrated to have serious negative effects, including promoting the development of breast and endometrial cancers.

Based upon a life expectancy of nearly eighty years in the United States, a woman can expect to spend about a third of her lifetime in a post-menopausal state. A woman's estrogen levels drop dramatically during menopause and menopausal women often experience many side affects associated with the reduction in estrogen production. To treat these conditions, physicians often prescribe hormone replacement therapy, which primarily consists of the administration of estrogen in combination with progestin.

In light of the more serious side effects associated with current hormone replacement therapy, including increased risk of ischemic stroke, myocardial infarction, thromboembolism, cerebrovascular disease, and endometrial carcinoma, a significant amount of research has been carried out to identify effective nonsteroidal estrogen and antiestrogenic compounds.

A large number of compounds have been described that either mimic or block the effects of the most potent estrogen, 17β-estradiol. Compounds that bind to an estrogen receptor and stimulate many of the same biological effects as 17β-estradiol are termed "estrogen receptor agonists." Compounds that inhibit the binding of 17β-estradiol to an estrogen receptor or interfere with the effects of 17β-estradiol binding to an estrogen receptor are referred to as "estrogen receptor antagonists." Compounds that affect different estrogen receptors with different potencies are typically referred to as selective estrogen receptor modulators (SERMs). SERMs may act as either agonists or antagonists to selectively modulate one or more estrogen receptors. Certain SERM compounds have mixed estrogenic and anti-estrogenic activities and act as estrogen receptor agonists in some tissues and as estrogen receptor antagonists in other tissues.

Estrogens, such as 17β-estradiol, have been thought to exert their effects by binding to one of two nuclear estrogen receptors, (ER)α or (ER)β. Because (ER)α and (ER)β are found in different tissues and have been demonstrated to have different biological roles, researchers have focused on the development of SERMs that effect a response by selectively binding to either (ER)α or (ER)β.

Two examples of nonsteroidal SERMs that exhibit different activities towards (ER)α and (ER)β are tamoxifen and raloxifene. Tamoxifen and raloxifene have been developed for the treatment and/or prevention of osteoporosis, cardiovascular disease and breast cancer in addition to the treatment and/or prevention of a variety of other disease states. Both compounds have been shown to exhibit an osteoprotective effect on bone mineral density combined with a positive effect on plasma cholesterol levels and a greatly reduced incidence of certain types of cancer. Unfortunately, tamoxifen and raloxifene both induce side effects such as hot flushes and tamoxifen promotes life-threatening disorders, such as endometrial cancer.

The present disclosure includes novel nonsteroidal SERMs that elicit the desired effects of hormone replacement therapy without inducing the negative effects of hormone replacement therapy or those of known selective estrogen receptor modulators.

SUMMARY

The present disclosure includes novel compounds, compositions and methods for making and using the compounds and compositions. Generally, the disclosed compounds function as selective estrogen receptor modulators (SERMs). In one aspect, the compounds have Formula 1 and include hydrates and pharmaceutically acceptable prodrugs and salts thereof. Moreover, all chiral, diastereomeric and geometric isomeric forms of the disclosed Formulas are intended.

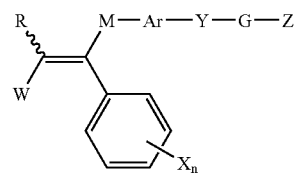

Formula 1

With reference to Formula 1, R can be E or Z with respect to M and R represents aryl, cycloalkyl, or phenyl (optionally substituted with a hydroxy or a lower aliphatic group); X is independently, at each occurrence, hydrogen, hydroxy, alkoxy, or halogen, wherein n=1-2; M comprises a ketone, amide or sulfonamide group. Ar represents an aromatic group and can be any aromatic group, including, without limitation, phenyl, biphenyl, 1-naphthyl, 2-naphthyl, and including heteroaryl groups, such as, by way of example, furan, thiophene, pyrrole, imidazole, oxazole, thiazole, pyridine, and quinoline groups. Y can be attached at any position, such as at the ortho, meta or para position relative to M. In one aspect, Y is a heteroatom, such as —O—, —NR$_1$—, or —S—. In certain embodiments of the disclosed SERMs according to Formula 2 Y represents a phenyl group.

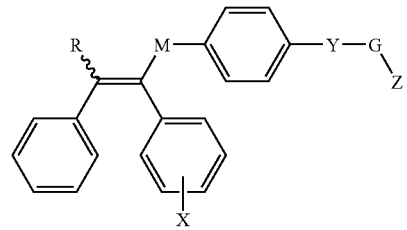

Formula 2

With continued reference to Formulas 1 and 2, G includes a linker group, such as a lower alkyl group, a lower alkylenyl group, a hydrocarbon chain, an oligoethylene glycol chain or the like. In one embodiment of Formula 2 wherein G includes a lower alkylenyl group, G is an ethyl group. Z typically includes a heteroatom. In certain embodiments Z includes a charged moiety, for example an anionic group, such as a boronate, sulfate, sulfonate, phosphate, phosphonate or a carboxy group. In examples wherein Z includes a cationic group, the cationic group can be an amino group, such as a dimethylamino or piperidino group. In other examples Z includes a hydroxyl group. Examples of groups represented by the formula Y-G-Z include those wherein Y is a heteroatom, such as oxygen and the formula -G-Z represents, without limitation, one of the following:

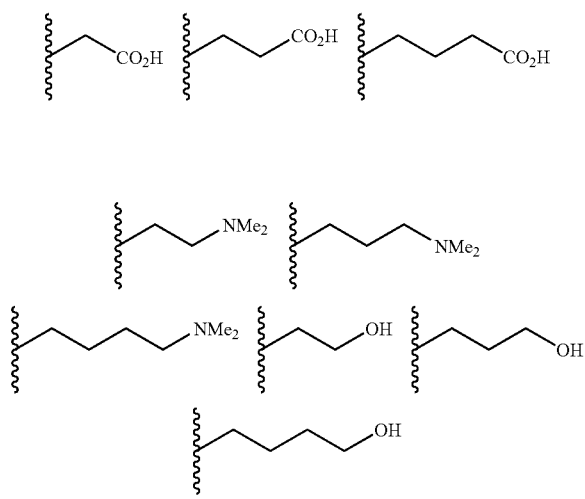

With reference to Formulas 1 and 2, M typically is one of an amide ketone or a sulfonamide group and more typically represents one of —C(O)—; —C(O)—$NR^1$—; —(C=S)N—, or —$SO_2NR^1$—; wherein $R^1$ is hydrogen, a lower alkyl group or aralkyl group. Thus, examples of such compounds can be represented by Formula 3 wherein Q typically forms an amide or sulfonamide linkage (Q represents —$SO_2$— or CO).

With reference to formula 3:

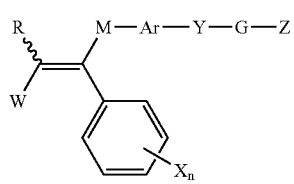

Formula 3 or a pharmaceutically acceptable salt thereof, R represents H or a lower alkyl; W represents naphthyl (optionally substituted with hydroxy, halogen, or lower alkyl) or phenyl (substituted with hydroxy, halogen, or lower alkyl); M represents carbonyl, —(C=O)$NR_1$—, or —(C=S)$NR_1$—; Ar represents an aromatic group; X represents independently at each occurrence, hydroxy, alkoxy, or halogen, wherein n=1-2; Y represents —O—, —$NR_1$—, or —S—; G represents a linker group; Z represents hydroxyl or a charged group; and $R_1$ represents hydrogen or lower alkyl.

With reference to formula 4:

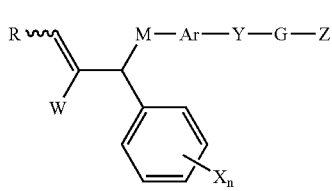

Formula 4 or a pharmaceutically acceptable salt thereof, R represents hydrogen or a lower alkyl; W represents naphthyl (optionally substituted with hydroxy, halogen, or lower alkyl) or phenyl (optionally substituted with hydroxy, halogen, or lower alkyl); M represents carbonyl, —(C=O)$NR_1$—, or —(C=S)$NR_1$—; Ar represents an aromatic group; X represents independently at each occurrence, hydroxy, alkoxy, or halogen, wherein n=1-2; Y represents —O—, —$NR_1$—, or —S—; G represents a linker group; Z represents a carboxyl, hydroxy or amino group, wherein the amino group is optionally substituted with an alkyl; and $R_1$ represents hydrogen or lower alkyl.

With reference to formula 5:

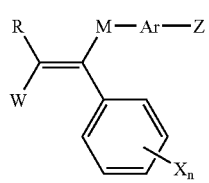

Formula 5 or a pharmaceutically acceptable salt thereof, R represents aryl, cycloalkyl, lower alkyl, phenyl optionally substituted with hydroxyl or lower aliphatic group; W represents naphthyl or phenyl (optionally substituted with H, hydroxyl, halogen, or methyl); M represents a carbonyl, —(C=O)$NR_1$—, or —(C=S)$NR_1$—; Ar represents an aromatic group; X represents independently at each occurrence, hydroxy, alkoxy, or halogen, wherein n=1-2; G represents a linker group; and Z represents hydroxy.

With reference to formula 6:

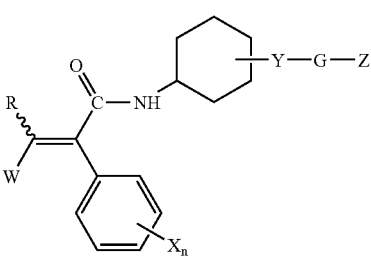

Formula 6 or a pharmaceutically acceptable salt thereof, R represents aryl, cycloalkyl, lower alkyl, phenyl optionally substituted with hydroxy or a lower aliphatic group; W represents naphthyl (optionally substituted with hydroxy, halogen, or lower alkyl) or phenyl (optionally substituted with hydroxy, halogen, or lower alkyl); X represents independently at each occurrence, hydroxy, alkoxy, or halogen, wherein n=1-2; Y represents —O—, —$NR_1$—, or —S—; G represents a linker group; Z represents a carboxyl, hydroxy or amino group, wherein the amino group is optionally substituted with an alkyl; and $R_1$ represents hydrogen or lower alkyl.

The disclosure also includes methods and compositions for treating a variety of disorders, particularly those characterized by an estrogen deficiency such as those associated with ovarectomy, ovarian failure or menopause. Such conditions and disorders include, generally, those described as autonomic dysfunctions, cognitive decline, motor dysfunctions, mood disorders, eating disorders and cardiovascular diseases, as well as different types of disorders. In one aspect, the disclosed compounds exert prophylactic effects against certain types of injuries. For example, the compounds can be used as neuroprotectants. Indeed, compounds that agonize the membrane-associated estrogen receptor identified herein act as neuroprotectants to reduce neuronal cell death in response to ischemic stroke and inhibit reperfusion injury.

Particular compositions include at least one compound according Formula 1 as well as a second therapeutic compound. The second compound also can bind to an estrogen receptor. For example, in one embodiment the second compound is a SERM and in another embodiment the second compound is an estrogen, such as 17β-estradiol, or a progesterone, such as progestin.

BRIEF DESCRIPTION OF THE DRAWINGS

FIG. 7A compares uteri size following treatment with 17β-estradiol versus an exemplary SERM disclosed herein and shows that in 17β-estradiol-treated mice, there was a noticeable increase in uterine size after estradiol benzoate (EB), compared with oil-vehicle treatment or treatment with an exemplary SERM disclosed herein.

FIG. 7B is a bar graph recording the uterine weights for EB treated mice versus oil and SERM treated mice (n=3-5 mice/group).

DETAILED DESCRIPTION

Figure 1:
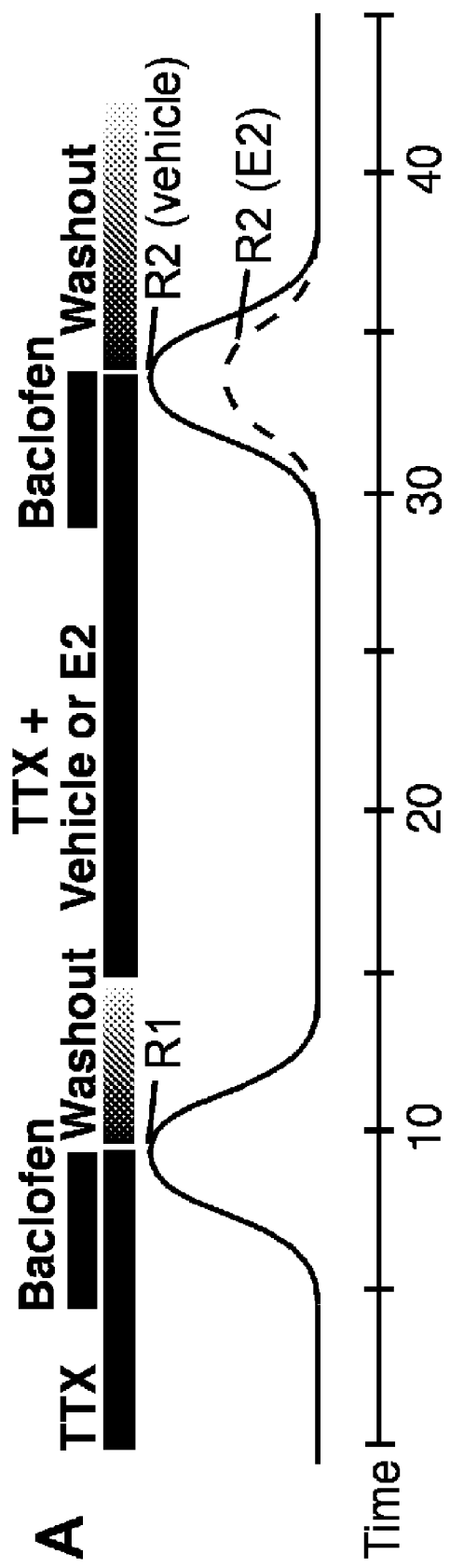
FIG. 1 is a schematic illustrating the protocol for drug administration in the whole-cell patch, voltage clamp studies.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

The specification includes the following acronyms and abbreviations:

| BAPTA: | 1,2-bis-(o-aminophenoxyethane)-N,N,N',N'-tetraacetic acid |
|---|---|
| CTX: | cholera toxin |
| DAG: | diacylglycerol |
| DCM: | dichloromethane |
| $ddH_2O$: | deionized distilled water |
| DMF: | N,N-dimethylformamide |
| EGTA: | ethylene glycol tetraacetic acid |
| EtOAc: | ethyl acetate |
| ERK: | extracellular-signal related kinase |
| GIRK: | G protein-coupled, inwardly-rectifying $K^+$ channel |
| Hex: | hexanes |
| MAPK or MAP kinase: | mitogen activated protein kinase |
| PLC: | phospholipase C |
| PKA: | protein kinase A |
| PKC: | protein kinase C |
| POMC: | proopiomelanocortin |
| SERM: | selective estrogen receptor modulator |
| TTX: | tetrodotoxin |

Ranges can be expressed herein as from "about" one particular value, and/or to "about" another particular value. When such a range is expressed, another embodiment includes from the one particular value and/or to the other particular value. Similarly, when values are expressed as approximations, by use of the qualifier "about," it will be understood that the particular value forms another embodiment. It will be further understood that the endpoints of each of the ranges are significant both in relation to the other endpoint, and independently of the other endpoint.

The disclosed compounds include chiral compounds, such as those that contain an asymmetrically tetrasubstituted carbon atom. Such compounds can be isolated in racemic or in optically active forms. It is known to those of ordinary skill in the art how to synthesize compounds in optically active form.

It also is well known how to prepare optically active compounds by resolution of racemic mixtures of compounds. All chiral, diastereomeric and geometric isomeric forms of the disclosed structures are intended unless specifically indicated otherwise.

In this specification and in the claims which follow, reference will be made to a number of terms which shall be understood to have the following meanings:

"Optional" or "optionally" means that the subsequently described event or circumstance can but need not occur, and that the description includes instances wherein said event or circumstance occurs and instances wherein it does not.

Variables, such as R, G, M, Q, X, Y and Z, used throughout the disclosure are the same variables as previously defined unless stated to the contrary.

The term "estrogen receptor agonist" refers to a compound that acts at an estrogen receptor and has at least some of the same biological effects as 17β-estradiol. Compounds that act at an estrogen receptor to block the effects of 17β-estradiol are called "estrogen receptor antagonists." Typically, the compounds disclosed herein are partial agonists or antagonists, which means that they mimic or block some of the effects of 17β-estradiol, but not others. In some cases the compounds exhibit mixed agonist/antagonist activity, wherein the compounds act as an estrogen receptor agonist in certain tissues, but act as an estrogen receptor antagonist in other tissues. Examples of such compounds disclosed herein exhibit partial agonist activity by binding selectively to one estrogen receptor with higher affinity than to other estrogen receptors. Compounds exhibiting such selectivity are termed "selective estrogen receptor modulators" or "SERMs."

"Hormone replacement therapy" refers to treatment given in response to reduced or insufficient estrogen production in a subject, for example as seen in menopause. Hormone replacement therapy often is undertaken in response to aging, ovarectomy or premature ovarian failure. Hormone replacement therapy is often used to help treat one or more of the secondary effects associated with estrogen insufficiency, such as osteoporosis, heart disease, hot flushes and mood disorders.

"Derivative" refers to a compound or portion of a compound that is derived from or is theoretically derivable from a parent compound.

The term "alkyl group" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl group" refers to a hydrocarbon group of 2 to 24 carbon atoms and structural formula containing at least one carbon-carbon double bond.

The term "alkynyl group" refers to a hydrocarbon group of 2 to 24 carbon atoms and a structural formula containing at least one carbon-carbon triple bond.

The term "halogenated alkyl group" refers to an alkyl group as described above with one or more hydrogen atoms present on these groups substituted with a halogen (F, Cl, Br, I).

The term "cycloalkyl group" refers to a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as described above wherein at least one of the carbon atoms of the ring is substituted with a heteroatom such as, but not limited to, nitrogen, oxygen, sulfur, or phosphorous.

The term "ethylene glycol chain" or "oligoethylene glycol chain" refers to a group having a repeating ethylene glycol unit. The ethylene glycol chain can be any length, however typically it includes from 2 to about 100 and more typically from 2 to about 70 ethylene glycol units. Most typically an oligoethylene glycol chain includes from about 2 to about 20 ethylene glycol units.

The term "aliphatic group" includes alkyl, alkenyl, alkynyl, halogenated alkyl and cycloalkyl groups as described above. A "lower aliphatic" group is a branched or unbranched structure having from 1 to 10 carbon atoms.

The term "aryl group" refers to any carbon-based aromatic group including, but not limited to, benzene, naphthalene, etc. The term "aromatic" also includes "heteroaryl group," which refers to an aromatic group that has at least one heteroatom incorporated within the ring of the aromatic group. Examples of such heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "aralkyl" refers to an aryl group having an alkyl group, as described above, attached to the aryl group. An example of an aralkyl group is a benzyl group.

The term "alkyl amino" includes alkyl groups as described above wherein at least one hydrogen atom is replaced with an amino group.

The term "heteroatom" is understood by those of ordinary skill in the art to refer to an atom other than a carbon atom. Examples of heteroatoms include, without limitation, boron, nitrogen, oxygen, phosphorus and sulfur.

The term "hydrocarbon chain" as used herein therefore typically refers to a chain of carbon atoms, typically comprising from 2 to about 22 carbon atoms. The chain can comprise aliphatic and aryl groups and can comprise straight chain, branched chain and/or cyclic groups.

The term "hydroxyl group" is represented by the formula —OH. The term "alkoxy group" is represented by the formula —OR, wherein R can be an alkyl group, optionally substituted with an alkenyl, alkynyl, aryl, aralkyl, cycloalkyl, halogenated alkyl, or heterocycloalkyl group as described above.

The term "hydroxyalkyl group" refers to an alkyl group that has at least one hydrogen atom substituted with a hydroxyl group. The term "alkoxyalkyl group" refers to an alkyl group that has at least one hydrogen atom substituted with an alkoxy group described above. Where applicable, the alkyl portion of a hydroxyalkyl group or an alkoxyalkyl group can have aryl, aralkyl, halogen, hydroxy, alkoxy The term "amine group" is represented by the formula —NRR', wherein R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "ester" is represented by the formula —OC(O)R, wherein R can be an alkyl, alkenyl, alkynyl, aryl, aralkyl, cycloalkyl, halogenated alkyl, or heterocycloalkyl group described above.

The term "carbonate group" is represented by the formula —OC(O)OR, wherein R can be an alkyl, alkenyl, alkynyl, aryl, aralkyl, cycloalkyl, halogenated alkyl, or heterocycloalkyl group described above.

The term "carboxylic acid" is represented by the formula —C(O)OH.

The term "aldehyde" is represented by the formula —C(O)H.

The term "keto group" is represented by the formula —C(O)R, wherein R is an alkyl, alkenyl, alkynyl, aryl, aralkyl, cycloalkyl, halogenated alkyl, or heterocycloalkyl group described above.

The term "carbonyl group" is represented by the formula C=O.

"Cationic group" or "cationic moiety" refers to a group that is positively charged or can be positively charged. For example, a cationic group can be an amine that is capable of being protonated at a physiologically relevant pH. A second example of a cationic group is a positively charged quaternary amine.

The disclosed compounds also encompass salts including, if several salt-forming groups are present, mixed salts and/or internal salts. The salts are generally pharmaceutically-acceptable salts that are non-toxic. Examples of salt-forming acidic groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Particular compounds possess at least one basic group that can form acid-base salts with inorganic acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 2-phenoxybenzoic acid, 2-acetoxybenzoic acid, embonic acid, nicotinic acid or isonicotinic acid, and in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

The term "ether group" is represented by the formula R(O)R', wherein R and R' can be, independently, an alkyl, alkenyl, alkynyl, aryl, aralkyl, cycloalkyl, halogenated alkyl, or heterocycloalkyl group described above.

The term "halide" refers to F, Cl, Br, or I.

The terms "urethane" and carbamate are represented by the formula —OC(O)NRR', wherein R and R' can be, independently, hydrogen, an alkyl, alkenyl, alkynyl, aryl, aralkyl, cycloalkyl, halogenated alkyl, or heterocycloalkyl group described above.

The groups described above can be optionally substituted with one or more substituents. The definition of any substituent or variable at a particular location in a molecule is independent of its definitions elsewhere in that molecule. Examples of suitable substituents include but are not limited to alkyl, alkenyl, alkynyl, aryl, halo, trifluoromethyl, trifluoromethoxy, hydroxy, alkoxy, oxo, alkanoyl, alkanoyloxy, aryloxy, amino, amido, alkanoylamino, aroylamino, aralkanoylamino, substituted alkanoylamino, aroylamino, aralkanoylamino, substituted alkanoylamino, substituted arylamino, substituted aralkanoylamino, thiol, sulfide, thiono, sulfonyl, sulfonamide, nitro, cyano, carboxy, carbamyl, substituted carbamyl and the like.

The term "prodrug" is intended to include any covalently bonded carriers that release an active parent drug of the present invention in vivo when the prodrug is administered to a subject. Since prodrugs are known to enhance the properties of pharmaceuticals, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying functional groups present in the compound in such a way that the modifications are cleaved, either in routine manipulation or in vivo, to yield the parent compound. Prodrugs include compounds having a hydroxy, amino, or sulfhydryl group functionalized with any group that is cleaved to yield the corresponding hydroxyl, free amino, or free sulfhydryl group, respectively. Examples of prodrugs include, without limitation, compounds having a hydroxy, amino and/or sulfhydryl group acylated with an acetate, formate, and/or benzoate group.

Protected derivatives of the disclosed compound also are contemplated. A variety of suitable for use with the disclosed compounds is disclosed in Greene and Wuts *Protective Groups in Organic Synthesis;* 3rd Ed.; John Wiley & Sons, New York 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure. Reference will now be made in detail to the present preferred embodiments.

I. SELECTION OF PREFERRED COMPOUNDS

Preferred compounds for modulating an estrogen receptor typically are selected for their potency and selectivity in agonizing or antagonizing one or more estrogen receptors. Typically the disclosed compounds selectively bind to a membrane associated estrogen receptor and bind to the nuclear estrogen receptors (ER)α and (ER)β with lower affinity, if at all. As described in the Methods and Examples section below, and as is generally known, efficacy of particular compounds against a target estrogen receptor can be determined in vitro, and the disclosed in vitro methods can be used to screen and identify novel SERMs. Moreover, particular compounds are provided for treating or protecting against various conditions and disorders, including conditions that are associated with menopause or other conditions characterized by estrogen insufficiency, such as those associated with ovarectomy, ovarian failure or menopause. Examples of such conditions include, without limitation, hot flushes, cognitive decline, osteoporosis, depression, ischemic brain damage and atherosclerosis.

The ability of the disclosed compounds to inhibit or ameliorate hot flushes can be determined, for example, in a standard assay that measures the ability of an agent to blunt the increase in tail skin temperature that occurs when morphine-addicted rats undergo acute withdrawal from morphine using naloxone. See, Merchenthaler, et al. The effect of estrogens and antiestrogens in a rat model for hot flush. *Maturitas* 1998, 30, 307-316, which is incorporated herein by reference. See also, Berendsen et al. Effect of tibolone and raloxifene on the tail temperature of oestrogen-deficient rats. *Eur. J. Pharmacol.* 2001, 419, 47-54; and Pan et al. A comparison of oral micronized estradiol with soy phytoestrogen effects on tail skin temperatures of ovariectomized rats. *Menopause* 2001, 8, 171-174. Both the Berendsen and Pan publications are incorporated herein by reference.

Certain disclosed compounds are useful for the treatment of multiple sclerosis. Preferred compounds for treating or suppressing the symptoms of multiple sclerosis can be selected by using the experimental autoimmune encephalomyelitis mouse model described by Polanczyk et al. *Am. J. Pathol.* 2003, 163, 1599-1605. The Polanczyk publication is incorporated herein by reference.

Disclosed compounds that are useful for treating eating disorders, such as anorexia nervosa and/or bulimia nervosa can be identified using a simple feeding assay as is known to those of ordinary skill in the art.

The effect of the disclosed compounds on learning and memory can be assessed using the Morris water maze and object recognition assays according to the protocols described by Stackman et al. *J. Neuroscience* 2002, 22, 10163-10171. The Stackman et al. publication is incorporated herein by reference.

The neuroprotective activity of the disclosed compounds also can be evaluated, for example, in a standard in vitro pharmacological assay using glutamate challenge. See, Zaulyanov, et al. *Cellular & Molecular Neurobiology* 1999, 19: 705-718; and Prokai, et al. *Journal of Medicinal Chemistry* 2001, 44, 110-114. Both the Zaulyanov et al. and Prokai et al. publications are incorporated herein by reference.

The disclosed compounds also can be evaluated for their ability to protect neurons from damage associated with global cerebral ischemia. Compounds can be evaluated for their ability to reduce such damage using the cardiac arrest and cardiopulmonary resuscitation assay described by Vogel et al. *Anesthesiology* 2003, 99, 112-121. In one aspect, the compounds can reduce the damage to neurons even when administered after resuscitation. The Vogel et al. publication is incorporated herein by reference.

Neuroprotection also can be evaluated using a middle cerebral artery occlusion procedure in mice according to the protocol described by Dubal et al. in *Proc. Natl. Acad. Sci. U.S.A.* 2001, 98, 1952-1957; and in *J. Neurosci.* 1999, 6385-6393. Additional assays for evaluating the disclosed compounds in different models of disorders characterized by estrogen insufficiency are described in the Methods and Examples section below.

Use of the compounds is not necessarily limited to conditions involving estrogen insufficiency. Techniques and assays for characterizing the efficacy of therapeutics for treating or preventing such conditions and disorders are well known and are described, for example, by Malamas et al. and Mewshaw et al. in U.S. patent publication numbers 2003/0171412 A1 and 2003/0181519 A1, respectively. Both the Malamas et al. and Mewshaw et al. publications are incorporated herein by reference.

II. PHARMACEUTICAL COMPOSITIONS

Another aspect of the disclosure includes pharmaceutical compositions prepared for administration to a subject and which include a therapeutically effective amount of one or more of the currently disclosed compounds. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. The relationship of these factors to determining a therapeutically effective amount of the disclosed compounds is understood by those of ordinary skill in the art.

The therapeutically effective amount of the compound or compounds administered can vary depending upon the desired effects and the factors noted above. Typically, dosages will be between about 0.01 mg/kg and 100 mg/kg of the subject's body weight, and more typically between about 0.01 mg/kg and 10 mg/kg of the subject's body weight. In one aspect the therapeutically effective amount can be selected to achieve an in vivo concentration of the therapeutic agent in a target tissue of a subject of about the concentration found to be effective in vitro.

In one embodiment, the disclosed SERM is used in combination with additional compounds disclosed herein and/or other therapeutic agents, such as other SERMs, anti-cancer agents or anti-proliferative agents. For example the disclosed compounds may be used with chemotherapeutic agents, such as tamoxifen, taxol, epothilones, methotrexate, and the like. In one aspect, a disclosed SERM is used in combination with a steroid hormone, such as an estrogen, including 17β-estradiol, a progesterone or the like. The estrogen or progesterone can be a naturally occurring or synthetic estrogen or progesterone. When different therapeutic agents are used in combination, the therapeutic agents can be administered together or separately. The therapeutic agents can be administered alone, but more typically are administered with a pharmaceutical carrier selected on the basis of the chosen route of administration and standard pharmaceutical practice.

Any of the SERMs described herein can be combined with a pharmaceutically acceptable carrier to form a pharmaceutical composition. Pharmaceutical carriers are known to those skilled in the art. These most typically would be standard carriers for administration of compositions to humans, including solutions such as sterile water, saline, and buffered solutions at physiological pH. The compositions could also be administered intramuscularly, subcutaneously, or in an aerosol form. Other compounds will be administered according to standard procedures used by those skilled in the art.

Molecules intended for pharmaceutical delivery can be formulated in a pharmaceutical composition. Pharmaceutical compositions can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, sustained release of the pharmaceutical preparation that comprises an effective amount of a disclosed SERM can be beneficial. Slow-release formulations are known to those of ordinary skill in the art. By way of example, polymers such as bis(p-carboxyphenoxy)propane-sebacic-acid or lecithin suspensions can be used to provide sustained release.

It is specifically contemplated in some embodiments that SERM delivery is via an injected and/or implanted drug depot, for instance comprising multi-vesicular liposomes such as in DepoFoam (SkyePharma, Inc, San Diego, Calif.) (see, for instance, Chamberlain et al. *Arch. Neuro.* 1993, 50, 261-264; Katri et al. *J. Pharm. Sci.* 1998, 87, 1341-1346; Ye et al., *J. Control Release* 2000, 64, 155-166; and Howell, *Cancer J.* 2001, 7, 219-227).

III. METHODS FOR USING THE DISCLOSED COMPOUNDS

The disclosed compounds can be used to selectively modulate an estrogen receptor in a subject and thus are useful for treating a variety of disorders, including those characterized by an estrogen deficiency. Moreover, because certain disclosed compounds exhibit selectivity for one or more estrogen receptors, the compounds can be used to treat conditions including but not limited to those described as autonomic dysfunctions, cognitive decline, motor dysfunctions, mood disorders, eating disorders and cardiovascular disorders, as well as different types of disorders. Generally, the compounds are useful for hormone replacement therapy without inducing the same incidence of serious side effects associated with the steroidal hormones (such as estrogen or synthetic estrogens) used in current hormone replacement therapies. The disclosed compounds also avoid side effects such as hot flushes encountered in treatment with currently known SERMs, such as tamoxifen or raloxifene. More specifically, the disclosed compounds can be used to treat disorders including, without limitation, ischemia-induced neuronal death, head trauma, Alzheimer's disease, disorders of temperature regulation, such as hot flushes, sleep cycle disruptions, Parkinson's disease, tardive diskinesia, depression, schizophrenia, anorexia nervosa, bulimia nervosa, cardiovascular disease, atherosclerosis, long QTL syndromes, such as Romano-Ward or Torsades de Pointes syndromes, osteoporosis, rheumatoid arthritis, osteoarthritis, bone fractures and multiple sclerosis. In one embodiment particular compounds can be used to promote vasodilation by modulating fluid balance, such as by blocking epithelial transport of sodium or chloride. Without limitation to theory, the compounds appear to function by activating maxi-K channels. See, Valverde et al. *Science* 1999, 285, 1929-1931.

In another embodiment, the disclosed compounds can be used to treat autoimmune diseases, particularly autoimmune diseases that occur more frequently in women than in men. Examples of such diseases include, without limitation, multiple sclerosis, rheumatoid arthritis, Grave's disease, systemic lupus erythematosus and myasthenia gravis. In another embodiment the disclosed compounds function to maintain or enhance immune competency in a subject. Moreover, the disclosed compounds exert prophylactic effects against certain types of injuries. For example, the compounds can be used as neuroprotectants. Indeed, compounds that agonize the membrane-associated estrogen receptor identified herein act as neuroprotectants in response to ischemic stroke and inhibit reperfusion injury.

Moreover, because of the ability of the disclosed compounds to selectively modulate one or more specific types of estrogen receptor, they can be used to identify the contribution of different estrogen receptors that mediate different physiological effects. The disclosed compounds also can be used to bind to and identify the particular class of membrane bound receptors at which these agents act. Indeed, a working embodiment of the disclosed selective estrogen receptor modulators had a ten-fold higher potency than 17β-estradiol for the membrane-associated receptor and a million-fold lower affinity than 17β-estradiol for the nuclear estrogen receptors (ER)α and (ER)β.

Another application of the disclosed compounds is affinity chromatography. Because examples of the presently disclosed compounds bind to a novel, membrane-associated estrogen receptor, the compounds can be used to purify the receptor, or remove the receptor from a sample. To use the compounds, they typically are attached to a solid support as is known to those of ordinary skill in the art. The compounds can be attached directly or via a linker molecule. Exemplary affinity chromatography techniques suitable for use with the disclosed compounds are disclosed in Current Protocols in Protein Science, John Wiley & Sons (J. E. Coligan et al., Eds.).

IV. SYNTHESIS

The compounds disclosed herein, as well as analogs of such compounds that will be readily apparent to those of ordinary skill in the art of medicinal chemistry upon consideration of this disclosure, can be prepared in a number ways using techniques well known to those of ordinary skill in the art. Exemplary methods for making particular compounds are described below. It is understood by those of ordinary skill in the art of organic synthesis that these methods are generalizable to the synthesis of compounds not explicitly described below upon consideration of the functionality of the molecule in view of the reagents and reactions disclosed. In view of the disclosed conditions, a person of ordinary skill in the art will recognize alternate methods for preparing analogous compounds that may have functional groups that are incompatible with the specific conditions disclosed herein.

Depending upon the functional groups present in a given transformation, protecting groups for various groups may be preferred for masking the group during the transformation. Suitable protecting groups for various functionalities are described in Greene and Wuts *Protective Groups in Organic Synthesis;* 3rd Ed.; John Wiley & Sons, New York (1999).

One embodiment of a method for synthesizing the disclosed compounds is illustrated in Scheme 3, below. With reference to Scheme 3, the method includes providing a compound 2 and converting compound 2 to compound 4. Compound 2 was prepared according to the protocol reported by Weatherman et al. *Chemistry & Biology* 2001, 8, 427-436. In working examples compound 2 was subjected to lithium-halogen exchange conditions, followed by reaction with allyl chloroformate to give compound 4. Compound 6 was prepared via palladium-catalyzed cleavage of the allyl ester group. In working examples, catalytic $Pd(PPh_3)_4$ was used along with $PhSiH_3$ to produce compound 6. Compound 6 is a versatile intermediate that can be used to prepare a variety of N-substituted acrylamide derivatives. For example, any primary or secondary amine can be incorporated via an amide bond forming reaction with compound 6. The method illustrated in Scheme 3 produces both the E and Z isomers, compounds 8 and 9, respectively.

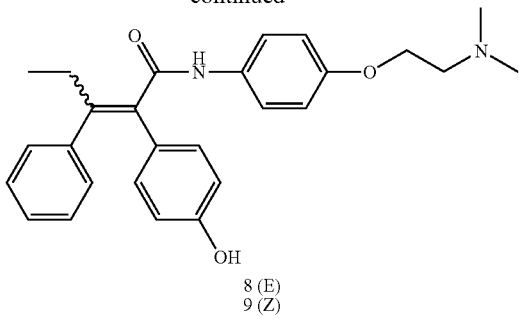

8 (E)
9 (Z)

Additional SERMs can be prepared according to Scheme 4. With reference to Scheme 4, compound 10 can be prepared from diphenylacetylene. A variety of alkyl groups (in addition to ethyl) can be introduced in this step by various techniques. The iodo group introduced in compound 10 can be used to introduce a carboxy group, such as the carboxy methyl ester 12, which is readily converted to the corresponding carboxylic acid 7. Carboxylic acid 7 can be reacted with a variety of primary and secondary amines to yield the corresponding amides, such as 8 and the corresponding Z isomer 9.

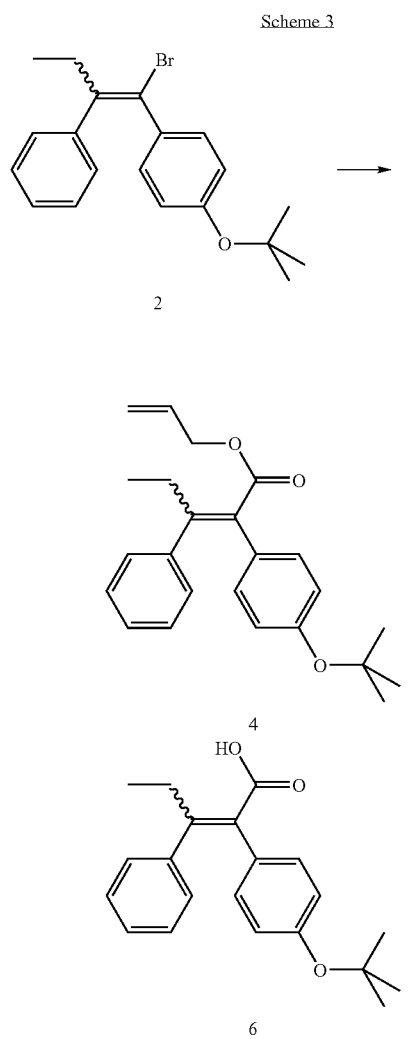

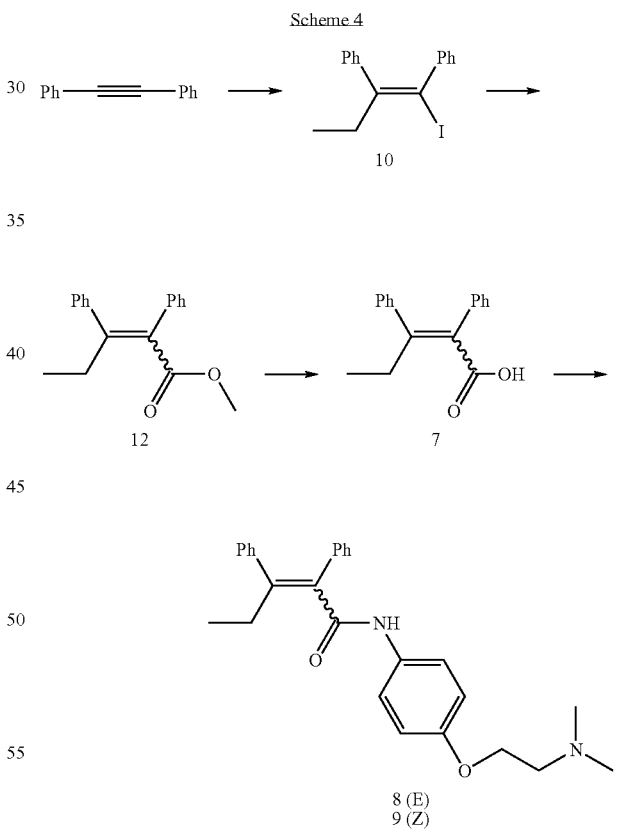

Disubstituted acrylamide derivatives can be prepared according to the method illustrated in Scheme 5. With reference to Scheme 5, bis-allylation of 18 yields 20. Aldol reaction of 20 with benzaldehyde yields 22, which undergoes elimination to yield 24, as a mixture of E and Z isomers. Cleavage of the allyl protecting groups yields 26, followed by amide bond formation to form E and Z isomers, 28 and 30, respectively.

Scheme 5

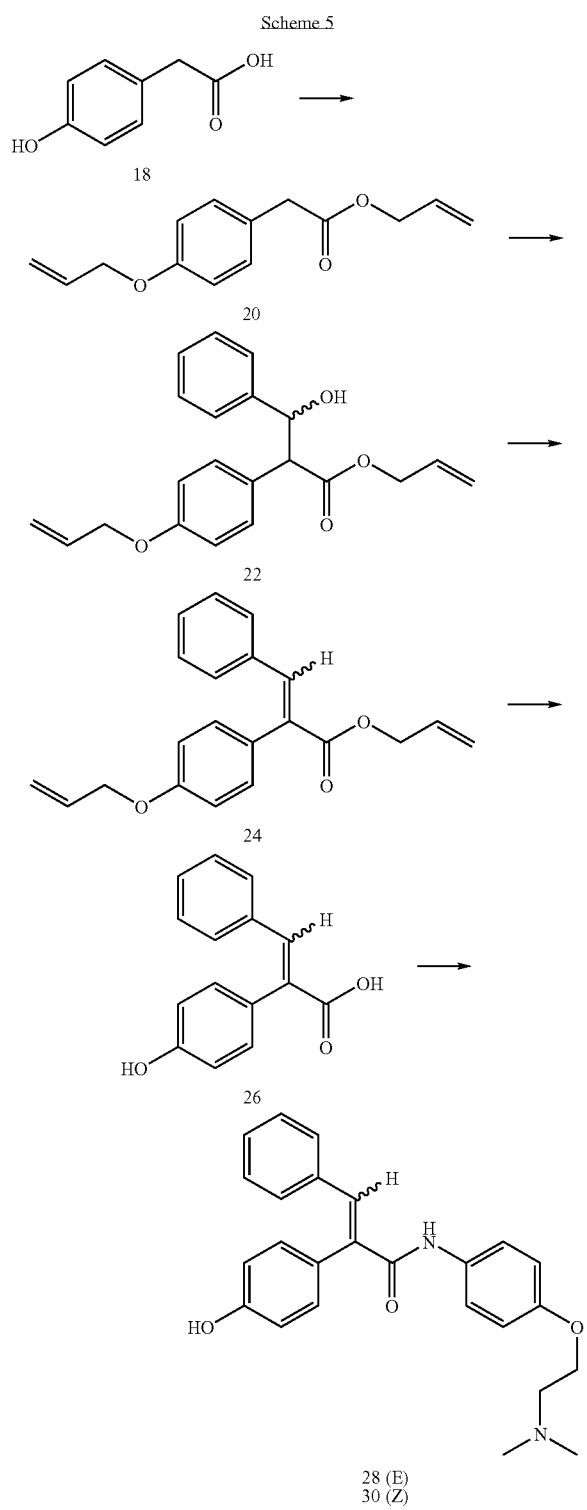

Scheme 6

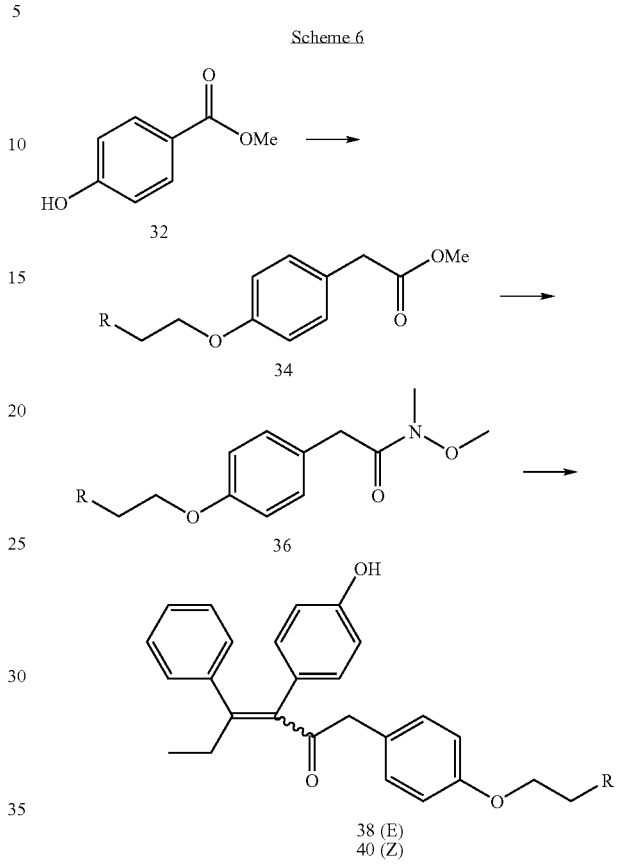

diate 34 is reacted with the lithium anion of compound prepared from compound 2 (Scheme 3), to yield, after deprotection, E and Z isomers 38 and 40, respectively.

Scheme 6 depicts an embodiment of a method for synthesizing vinyl ketone derived SERMs. With reference to Scheme 6, alkylation of compound 32 is a versatile reaction that can be used to introduce a variety of groups. For example, R can include, with limitation, a hydroxy group, a protected hydroxy group, a carboxy group, a protected carboxy group, an amine or a protected amino group. In working examples R was a dimethyl amino group or a piperidino group. Intermediate 34 is reacted with the lithium anion of compound prepared from compound 2 (Scheme 3), to yield, after deprotection, E and Z isomers 38 and 40, respectively.

V. METHODS AND EXAMPLES

The foregoing disclosure is further explained by the following non-limiting examples.

Scheme 7

(E)-Ethyl 2-(4-(methoxymethoxy)phenyl)-3-phenylpent-2-enoate (2). To a mixture of Ethyl 2-pentynoate (5.5 g, 43.6 mmol), 1-iodo-4-(methoxymethoxy)benzene (23.0 g, 87.1 mmol), Phenylboronic acid (10.6 g, 86.9 mmol) in DMF (132 ml) was added a solution of $K_2CO_3$ (12.1 g, 87.5 mmol) in $H_2O$ (33 ml) under ice cooling, then the mixture was stirred at room temperature for 10 min. $PdCl_2(PhCN)_2$ (167 mg, 0.435 mmol) was added under Ar atmosphere, and the mixture was stirred at room temperature for 24 h. The reaction was quenched with $H_2O$ under ice cooling, and the whole was extracted with $Et_2O$. The organic layer was washed with $H_2O$, brine, dried over $Na_2SO_4$, then concentrated. Purification by silica gel flash column chromatography (eluent: hexane/AcOEt, 30:1 to 10:1) gave 2 (29%) and the regioisomer (24%). 2: colorless oil; $^1$H-NMR ($CDCl_3$) δ 1.00 (3H, t, J=7.4), 1.31 (3H, t, J=7.1 Hz), 2.63 (2H, q, J=7.4 Hz), 3.42 (3H, s), 4.28 (2H, q, J=7.1 Hz), 5.07 (2H, s), 6.75 (2H, d, J=8.8 Hz), 6.90 (2H, d, J=8.8 Hz), 7.04 (2H, m), 7.12-7.21 (3H, m); regioisomer: $H^1$-NMR ($CDCl_3$) δ 1.02 (3H, t, J=7.4 Hz), 1.29 (3H, t, J=7.1 Hz), 2.64 (2H, q, J=7.4 Hz), 3.45 (3H, s), 4.27 (2H, q, J=7.1 Hz), 5.10 (2H, s), 6.81 (2H, d, J=8.8 Hz), 6.95 (2H, d, J=8.8 Hz), 7.00 (2H, m), 7.06-7.14 (3H, m).

(E)-2-(4-(methoxymethoxy)phenyl)-3-phenylpent-2-enoic acid (3). To a solution of 2 (3.4 g, 9.99 mmol) in MeOH (85 ml) was added 2N NaOH (50 ml), and the mixture was stirred at 80° C. for 15 h. After cooling, 2 N HCl (50 ml) was added drop wise under ice cooling, and the whole was extracted with AcOEt, the organic layer was washed with brine, dried over $Na_2SO_4$, then concentrated. The residual solid was triturated with hexanes to give 3 (88%). 3: colorless powder; $^1$H-NMR (CDCl$_3$) δ 1.03 (3H, t, J=7.4 Hz), 2.81 (2H, q, J=7.4 Hz), 3.42 (3H, s), 5.08 (2H, s), 6.78 (2H, d, J=8.8 Hz), 6.94 (2H, d, J=8.8 Hz), 7.02 (2H, m), 7.11-7.19 (3H, m).

(E)-N-(4-(2-(dimethylamino)ethoxy)phenyl)-2-(4-(methoxymethoxy)phenyl)-3-phenylpent-2-enamide (4). Method A; To a mixture of 3 (2.50 g, 8.00 mmol), EDC.HCl (1.84 g, 9.60 mmol) and HOBt (1.30 g, 9.62 mmol) in DMF (50 ml) was added a solution of 4-(2-(dimethylamino)ethoxy)benzene-amine dihydrochloride (2.23 g, 8.81 mmol) and N,N-Diisopropylethylamine (4.13 g, 32.0 mmol) under ice cooling, and the mixture was stirred at room temperature for 18 h. The reaction was quenched with saturated aqueous NaHCO$_3$ under ice cooling, and the whole was extracted with AcOEt, the organic layer was washed with H$_2$O×2, brine, dried over Na$_2$SO$_4$, then concentrated. Purification by silica gel flash column chromatography (eluent: AcOEt then CHCl$_3$/MeOH, 10:1) and recystallization from AcOEt-hexanes gave 4 (43%). 4: colorless powder; $^1$H-NMR (CDCl$_3$) δ 1.05 (3H, t, J=7.4), 2.33 (6H, s), 2.71 (2H, t, J=5.7 Hz), 2.77 (2H, q, J=7.4 Hz), 3.43 (3H, s), 4.04 (2H, t, J=5.7 Hz), 5.09 (2H, s), 6.78 (2H, d, J=8.8 Hz), 6.88 (2H, d, J=9.0 Hz), 7.00 (2H, d, J=8.8 Hz), 7.00 (1H, brs) 7.06 (2H, m), 7.12-7.23 (3H, m), 7.41 (2H, d, J=9.0 Hz).

Method B; To a mixture of 3 (2.90 g, 9.28 mmol), 4-(2-(dimethylamino)ethoxy)benzenamine dihydrochloride (2.58 g, 10.2 mmol), 4-Dimethylaminopyridine (56.7 mg, 0.464 mmol) in CH$_2$Cl$_2$ (100 ml) was added O-Benzotriazoyl-N,N,N',N'-tetramethyluronium Hexafluorophosphate (3.87 g, 10.2 mmol) under ice cooling, and the mixture was stirred at 0° C. for 10 min. Then N,N-Diisopropylethylamine (4.19 g, 32.4 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by Biotage (eluent: CH$_2$Cl$_2$ to CH$_2$Cl$_2$/MeOH, 6:1) gave the colorless solid. The solid was triturated with Et$_2$O-hexane to give 4 (65%).

(E)-N-(4-(2-(dimethylamino)ethoxy)phenyl)-2-(4-hydroxyphenyl)-3-phenylpent-2-enamide (5). Method A; To a suspension of 4 (1.39 g, 2.93 mmol) in MeOH (4 ml) was added a solution of 3N HCl in AcOEt (10 ml) under ice cooling, and the mixture was stirred at room temperature for 2 h. A solution of NaHCO$_3$ (2.8 g) in H$_2$O was poured into the reaction mixture under ice cooling, and the whole was extracted with AcOEt and a little MeOH. The organic layer was washed with brine, dried over Na$_2$SO$_4$, and then concentrated. The residual solid was triturated with Et$_2$O to give 5 (91%). 5: colorless powder; $^1$H-NMR (CD$_3$OD) δ 0.97 (3H, t, J=7.4 Hz), 2.38 (6H, s), 2.65 (2H, q, J=7.4 Hz), 2.82 (2H, t, J=5.4 Hz), 4.11 (2H, t, J=5.74 Hz), 6.50 (2H, d, J=8.8 Hz), 6.92 (2H, d, J=8.8 Hz), 6.94 (2H, d, J=9.2 Hz) 7.11-7.25 (5H, m), 7.53 (2H, d, J=9.1 Hz). $^{13}$C-NMR (CD$_3$OD) δ 13.21, 30.40, 45.76, 59.09, 66.74, 115.69, 115.75, 123.42, 127.91, 129.10, 129.31, 130.42, 131 0.78, 132.98, 136.10, 141.52, 143.52, 157.10, 157.55, 171.92. HRMS calcd for C$_{27}$H$_{30}$N$_2$O$_3$: 430.2256. Found: 430.2264.

Method B; To a solution of 4 (2.89 g, 6.09 mmol) in MeOH (40 ml) was added 4N HCl in 1,4-dioxane (15.2 ml) under ice cooling, and the mixture was stirred at room temperature for 2 h. A solution of NaHCO$_3$ in H$_2$O was poured into the reaction mixture under ice cooling, and the whole was extracted with AcOEt. The organic layer was washed with brine, dried over Na$_2$SO$_4$, and then concentrated. The residual solid was triturated with AcOEt to give 5 (89%).

Scheme 7-2

(E)-N-(4-hydroxyphenyl)-2-(4-(methoxymethoxy)phenyl)-3-phenylpent-2-enamide (6a). To a mixture of 3 (60 mg, 0.192 mmol), 4-aminophenol (23.0 mg, 0.211 mmol), 4-Dimethylaminopyridine (1.2 mg, 0.00982 mmol) and N,N-Diisopropylethylamine (37.2 mg, 0.287 mmol) in CH$_2$Cl$_2$ (2 ml) was added O-Benzotriazoyl-N,N,N',N'-tetramethyluronium Hexafluorophosphate (76.5 mg, 0.202 mmol) under ice cooling, and the mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by silica gel flash column chromatography (eluent: hexane/AcOEt, 3:1 to 2:1) gave 6a (68%). 6a: colorless powder; $^1$H-NMR (CDCl$_3$) δ 1.05 (3H, t, J=7.5 Hz), 2.77 (2H, t, J=7.5 Hz), 3.43 (3H, s), 5.09 (2H, s), 6.79 (4H, m), 7.00 (2H, d, J=8.8 Hz), 7.00 (1H, brs), 7.07 (2H, m), 7.15-7.22 (3H, m), 7.37 (2H, d, J=8.8 Hz).

(E)-N-(4-(3-(dimethylamino)propoxy)phenyl)-2-(4-(methoxymethoxy)phenyl)-3-phenylpent-2-enamide (6b). To a mixture of 3 (60 mg, 0.192 mmol), 4-(3-(dimethylamino)propoxy)benzenamine dihydrochloride (56.4 mg, 0.211 mmol), 4-Dimethylaminopyridine (1.2 mg, 0.00982 mmol) in CH$_2$Cl$_2$ (3 ml) was added O-Benzotriazoyl-N,N,N',N'-tetramethyluronium Hexafluorophosphate (76.5 mg, 0.202 mmol) under ice cooling, and the mixture was stirred at 0° C. for 10 min. Then N,N-Diisopropylethylamine (86.8 mg, 0.672 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by silica gel flash column chromatography (eluent: CHCl$_3$/MeOH, 20:1 to 10:1) gave the colorless solid (100%). The solid was triturated with Et$_2$O-hexane to give 6b (75%). 6b: colorless powder; $^1$H-NMR (CDCl$_3$) δ 1.05 (3H, t, J=7.4 Hz), 2.05 (2H, m), 2.42 (6H, s), 2.66 (2H, m), 2.77 (2H, q, J=7.4 Hz), 3.43 (3H, s), 4.00 (2H, t, J=6.2 Hz), 5.09 (2H, s), 6.79 (2H, d, J=9.0 Hz), 6.84 (2H, d, J=9.0 Hz), 7.00 (2H, d, J=9.0 Hz), 7.00 (1H, brs) 7.06 (2H, m), 7.13-7.23 (3H, m), 7.40 (2H, d, J=9.0 Hz).

(E)-N-((1r,4r)-4-(2-(dimethylamino)ethoxy)cyclohexyl)-2-(4-(methoxymethoxy)phenyl)-3-phenylpent-2-enamide (6c). To a mixture of 3 (90 mg, 0.288 mmol), (1r,4r)-4-(2-(dimethylamino)ethoxy)cyclohexanamine dihydrochloride (89.6 mg, 0.346 mmol), 4-Dimethylaminopyridine (1.8 mg, 0.0147 mmol) in CH$_2$Cl$_2$ (3 ml) was added O-Benzotriazoyl-N,N,N',N'-tetramethyluronium Hexafluorophosphate (120 mg, 0.316 mmol) under ice cooling, and the mixture was stirred at 0° C. for 10 min. Then N,N-Diisopropylethyllamine (130 mg, 1.01 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by Biotage 12M (eluent: CH$_2$Cl$_2$ to CH$_2$Cl$_2$/MeOH, 6:1) gave the colorless solid (88%). The solid was triturated with Et$_2$O-hexane to give 6c (73%). 6c: colorless powder; $^1$H-NMR (CDCl$_3$) δ 1.00 (3H, t, J=7.4 Hz), 1.13 (2H, m), 1.39 (2H, m), 2.04 (4H, (E)-N,2-bis(4-hydroxyphenyl)-3-phenylpent-2-enamide (7a). To a solution of 6a (45 mg, 0.112 mmol) in MeOH (1 ml) was added a solution of 4N HCl in dioxane (0.3 ml) under ice cooling, and the mixture was stirred at room temperature for 2 h. H$_2$O was poured into the reaction mixture under ice cooling, and the whole was extracted with AcOEt. The organic layer was washed with brine, dried over Na$_2$SO$_4$, and then concentrated. The residue was crystallized with Et$_2$O to give 7a (76%). 7a: colorless powder; $^1$H-NMR (CD$_3$OD) δ 0.97 (3H, t, J=7.5 Hz), 2.64 (2H, q, J=7.5 Hz), 6.51 (2H, d, J=8.8 Hz), 6.76 (2H, d, J=8.8 Hz), 6.92 (2H, d, J=8.8 Hz), 7.12-7.25 (5H, m), 7.40 (2H, d, J=8.8 Hz). HRMS calcd for C$_{23}$H$_{22}$NO$_3$: 360.1600. Found: 360.1605.

(E)-N-(4-(3-(dimethylamino)propoxy)phenyl)-2-(4-hydroxyphenyl)-3-phenylpent-2-enamide (7b). To a solution of 6b (55 mg, 0.113 mmol) in MeOH (0.5 ml) was added 3N HCl in AcOEt (0.5 ml) under ice cooling, and the mixture was stirred at room temperature for 1 h. A solution of NaHCO$_3$ (139 mg) in H$_2$O was poured into the reaction mixture under ice cooling, and the whole was extracted with AcOEt and a little MeOH. The organic layer was washed with brine, dried over Na$_2$SO$_4$, and then concentrated. The residue was crystallized with Et$_2$O to give 7b (76%). 7b: colorless powder; $^1$H-NMR (CD$_3$OD) δ 0.97 (3H, t, J=7.4 Hz), 1.99 (2H, m), 2.35 (6H, s), 2.59-2.66 (4H, m), 4.02 (2H, t, J=6.1 Hz), 6.51 (2H, d, J=8.8 Hz), 6.90 (2H, d, J=9.2 Hz), 6.92 (2H, d, J=8.8 Hz), 7.12-7.23 (5H, m), 7.50 (2H, d, J=9.2 Hz). HRMS calcd for C$_{28}$H$_{33}$N$_2$O$_3$ [M+H]$^+$: 445.2491. Found: 445.2507.

(E)-N-((1r,4r)-4-(2-(dimethylamino)ethoxy)cyclohexyl)-2-(4-hydroxyphenyl)-3-phenylpent-2-enamide (7c). To a solution of 6c (90 mg, 0.187 mmol) in MeOH (3 ml) was added 4N HCl in 1,4-dioxane (0.47 ml) under ice cooling, and the mixture was stirred at room temperature for 2 h. A solution of NaHCO$_3$ in H$_2$O was poured into the reaction mixture under ice cooling, and the whole was extracted with AcOEt. The organic layer was washed with brine, dried over Na$_2$SO$_4$, and then concentrated. The residue was crystallized with Et$_2$O to give 7c (93%). 7c: colorless powder; $^1$H-NMR (CD$_3$OD) δ 0.94 (6H, d, J=7.5 Hz), 1.36 (2H, m), 1.98 (2H, m), 2.09 (2H, m), 2.30 (6H, s), 2.53-2.59 (4H, m), 3.28 (2H, m), 3.61 (2H, t, J=5.8 Hz), 3.78 (1H, m), 6.47 (2H, d, J=8.8 Hz), 6.84 (2H, d, J=8.8 Hz), 7.09 (2H, m), 7.11-7.21 (3H, m). HRMS calcd for C$_{27}$H$_{37}$N$_2$O$_3$ [M+H]$^+$: 437.2804. Found: 437.2814.

Scheme 7-3

N-(4-(2-(dimethylamino)ethoxy)phenyl)-2-(4-(methoxymethoxy)phenyl)-3-phenylpent-3-enamide (3b). (byproduct). 3b: colorless powder; $^1$H-NMR (CDCl$_3$) δ 1.63 (3H, d, J=6.7 Hz), 2.32 (3H, s), 2.69 (2H, t, J=5.8 Hz), 3.48 (3H, s), 4.02 (2H, t, J=5.8 Hz), 4.61 (1H, s), 5.17 (2H, s), 5.72 (1H, q, J=6.7 Hz), 6.84 (2H, t, J=8.9 Hz), 7.01 (2H, d, J=8.9 Hz), 7.16 (2H, m), 7.20-7.32 (8H, m).

N-(4-(2-(dimethylamino)ethoxy)phenyl)-2-(4-hydroxyphenyl)-3-phenylpent-3-enamide (8). To a solution of 3b (30 mg, 0.0632 mmol) in MeOH (1 ml) was added 3N HCl in AcOEt (0.5 ml) under ice cooling, and the mixture was stirred at room temperature for 1 h. A solution of NaHCO$_3$ (139 mg) in H$_2$O was poured into the reaction mixture under ice cooling, and the whole was extracted with AcOEt. The organic layer was washed with brine, dried over Na$_2$SO$_4$, and then concentrated. The residue was crystallized with Et$_2$O to give 8 (67%). 8: colorless powder; $^1$H-NMR (CD$_3$OD) δ 1.53 (3H, dd, J=1.4, 6.8 Hz), 2.35 (6H, s), 2.77 (2H, t, J=5.4 Hz), 4.06 (2H, t, J=5.4 Hz), 4.64 (1H, brt), 5.53 (2H, dq, J=1.5, 6.8 Hz), 6.74 (2H, d, J=8.6 Hz), 6.85 (2H, d, J=9.2 Hz), 7.18-7.22 (5H, m), 7.27-7.32 (4H, m). HRMS calcd for C$_{27}$H$_{31}$N$_2$O$_3$ [M+H]$^+$: 431.2335. Found: 431.2348.

(E)-N-(4-(2-(dimethylamino)ethoxy)phenyl)-2-(4-(methoxymethoxy)phenyl)-N-methyl-3-phenylpent-2-enamide (9). To a solution of 3 (60 mg, 0.126 mmol) in DMF (1.5 ml) was added 60% NaH (6.0 mg, 0.15 mmol) under ice cooling, then the mixture was stirred at room, temperature for 10 min. Iodomethane (21.5 mg, 0.151 mmol) was added under ice cooling, and the mixture was stirred at room temperature for 1 h. The reaction was quenched with H$_2$O under ice cooling, and the whole was extracted with AcOEt. The organic layer was washed with H$_2$O, brine, dried over Na$_2$SO$_4$, then concentrated. Purification by silica gel flash column chromatography (eluent: CH$_2$Cl$_2$ to CH$_2$Cl$_2$/MeOH, 20:1) gave 9 (100%). 9: colorless powder; $^1$H-NMR (CDCl$_3$) δ 0.95 (3H, t, J=7.4 Hz), 2.34 (6H, s), 2.63 (2H, m), 2.71 (2H, q, J=5.6 Hz), 3.30 (3H, s), 3.43 (3H, s), 4.00 (2H, d, J=5.6H), 5.04 (2H, s), 6.47 (2H, d, J=9.0 Hz), 6.56 (2H, d, J=9.0 Hz), 6.68 (2H, d, J=9.3 Hz), 6.72 (2H, d, J=9.2 Hz), 6.85 (2H, m), 7.05-7.15 (3H, m).

(E)-N-(4-(2-(dimethylamino)ethoxy)phenyl)-2-(4-hydroxyphenyl)-N-methyl-3-phenylpent-2-enamide (10). Compound 10 was prepared by same method as that used for the preparation of compound 8. 10: colorless powder (84%); $^1$H-NMR (CD$_3$OD) δ 0.92 (3H, t, J=7.3 Hz), 2.36 (6H, s), 2.62 (2H, m), 2.79 (2H, t, J=5.3 Hz), 3.28 (3H, s), 4.07 (2H, t, J=5.3 Hz), 6.26-6.31 (4H, m), 6.76-6.82 (4H, m), 6.87 (2H, m), 7.06-7.16 (3H, m). HRMS calcd for C$_{28}$H$_{33}$N$_2$O$_3$: 445.2491. Found: 445.2502.

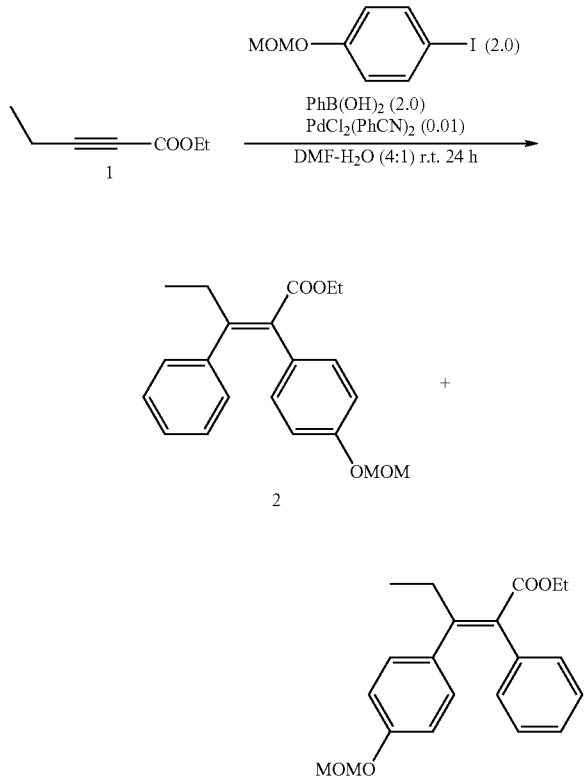

-continued
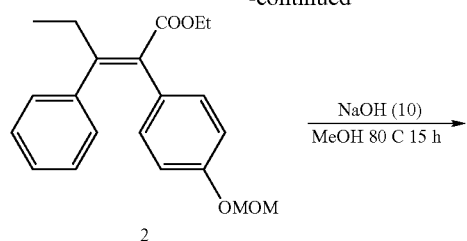
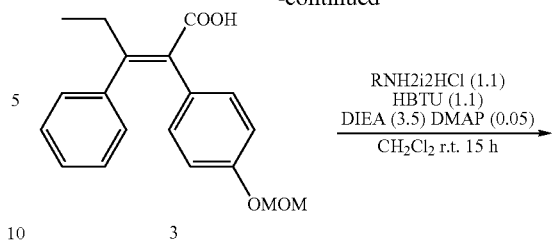
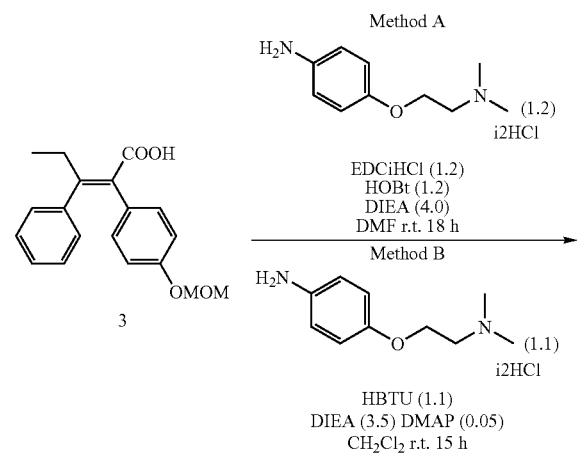
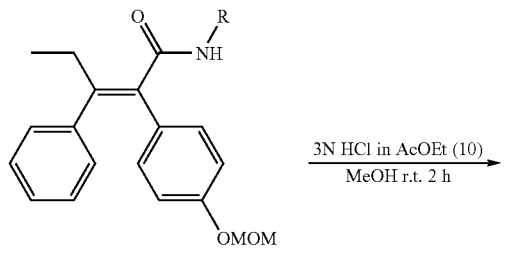
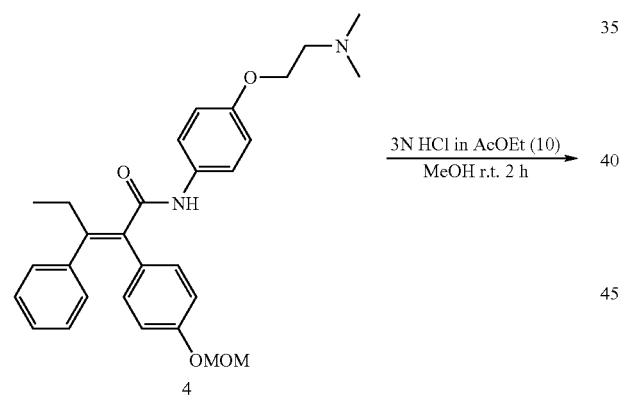
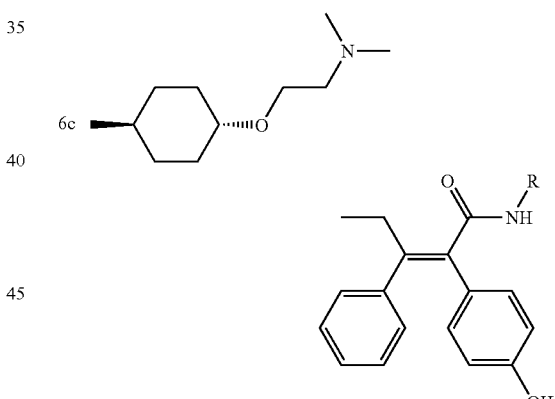
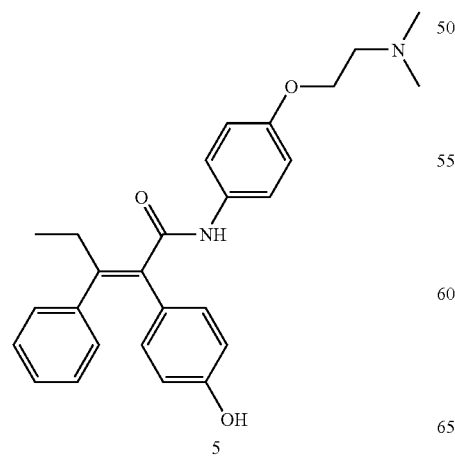
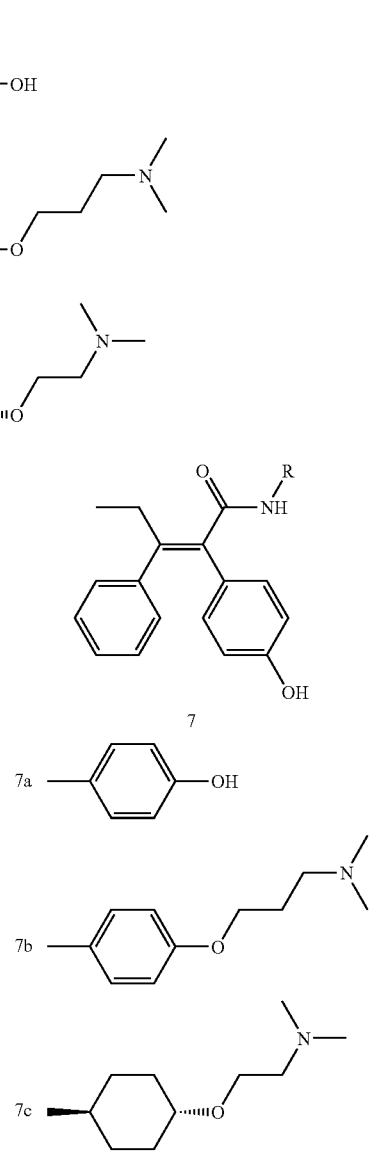

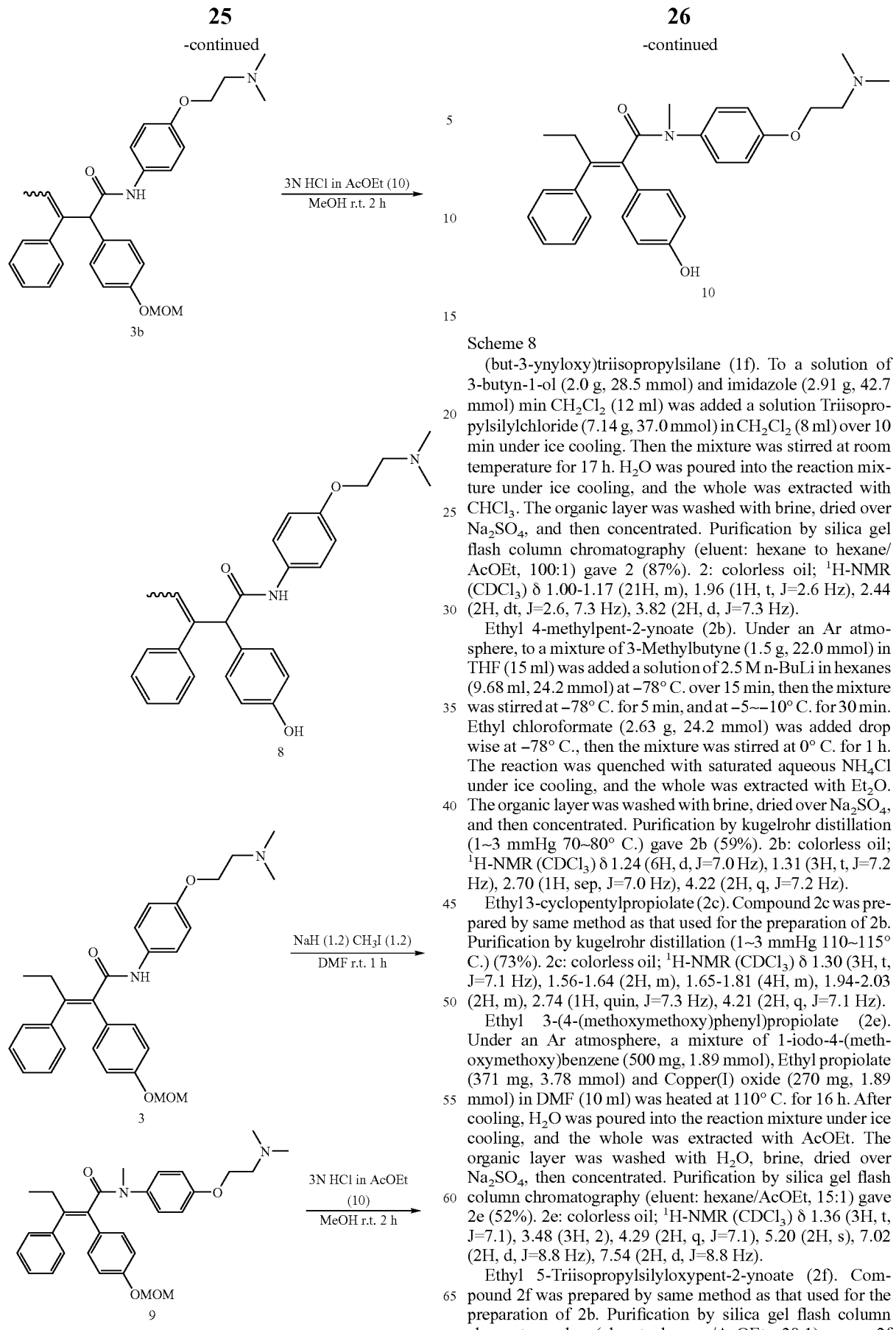

Scheme 8

(but-3-ynyloxy)triisopropylsilane (1f). To a solution of 3-butyn-1-ol (2.0 g, 28.5 mmol) and imidazole (2.91 g, 42.7 mmol) min $CH_2Cl_2$ (12 ml) was added a solution Triisopropylsilylchloride (7.14 g, 37.0 mmol) in $CH_2Cl_2$ (8 ml) over 10 min under ice cooling. Then the mixture was stirred at room temperature for 17 h. $H_2O$ was poured into the reaction mixture under ice cooling, and the whole was extracted with $CHCl_3$. The organic layer was washed with brine, dried over $Na_2SO_4$, and then concentrated. Purification by silica gel flash column chromatography (eluent: hexane to hexane/AcOEt, 100:1) gave 2 (87%). 2: colorless oil; $^1$H-NMR ($CDCl_3$) δ 1.00-1.17 (21H, m), 1.96 (1H, t, J=2.6 Hz), 2.44 (2H, dt, J=2.6, 7.3 Hz), 3.82 (2H, d, J=7.3 Hz).

Ethyl 4-methylpent-2-ynoate (2b). Under an Ar atmosphere, to a mixture of 3-Methylbutyne (1.5 g, 22.0 mmol) in THF (15 ml) was added a solution of 2.5 M n-BuLi in hexanes (9.68 ml, 24.2 mmol) at −78° C. over 15 min, then the mixture was stirred at −78° C. for 5 min, and at −5~−10° C. for 30 min. Ethyl chloroformate (2.63 g, 24.2 mmol) was added drop wise at −78° C., then the mixture was stirred at 0° C. for 1 h. The reaction was quenched with saturated aqueous $NH_4Cl$ under ice cooling, and the whole was extracted with $Et_2O$. The organic layer was washed with brine, dried over $Na_2SO_4$, and then concentrated. Purification by kugelrohr distillation (1~3 mmHg 70~80° C.) gave 2b (59%). 2b: colorless oil; $^1$H-NMR ($CDCl_3$) δ 1.24 (6H, d, J=7.0 Hz), 1.31 (3H, t, J=7.2 Hz), 2.70 (1H, sep, J=7.0 Hz), 4.22 (2H, q, J=7.2 Hz).

Ethyl 3-cyclopentylpropiolate (2c). Compound 2c was prepared by same method as that used for the preparation of 2b. Purification by kugelrohr distillation (1~3 mmHg 110~115° C.) (73%). 2c: colorless oil; $^1$H-NMR ($CDCl_3$) δ 1.30 (3H, t, J=7.1 Hz), 1.56-1.64 (2H, m), 1.65-1.81 (4H, m), 1.94-2.03 (2H, m), 2.74 (1H, quin, J=7.3 Hz), 4.21 (2H, q, J=7.1 Hz).

Ethyl 3-(4-(methoxymethoxy)phenyl)propiolate (2e). Under an Ar atmosphere, a mixture of 1-iodo-4-(methoxymethoxy)benzene (500 mg, 1.89 mmol), Ethyl propiolate (371 mg, 3.78 mmol) and Copper(I) oxide (270 mg, 1.89 mmol) in DMF (10 ml) was heated at 110° C. for 16 h. After cooling, $H_2O$ was poured into the reaction mixture under ice cooling, and the whole was extracted with AcOEt. The organic layer was washed with $H_2O$, brine, dried over $Na_2SO_4$, then concentrated. Purification by silica gel flash column chromatography (eluent: hexane/AcOEt, 15:1) gave 2e (52%). 2e: colorless oil; $^1$H-NMR ($CDCl_3$) δ 1.36 (3H, t, J=7.1), 3.48 (3H, 2), 4.29 (2H, q, J=7.1), 5.20 (2H, s), 7.02 (2H, d, J=8.8 Hz), 7.54 (2H, d, J=8.8 Hz).

Ethyl 5-Triisopropylsilyloxypent-2-ynoate (2f). Compound 2f was prepared by same method as that used for the preparation of 2b. Purification by silica gel flash column chromatography (eluent: hexane/AcOEt, 30:1) gave 2f (96%). 2f: yellow oil; $^1$H-NMR (CDCl$_3$) δ 0.98-1.15 (21H, m), 1.30 (3H, t, J=7.1 Hz), 2.58 (2H, t, J=7.1 Hz), 3.87 (2H, t, J=7.1 Hz), 4.22 (2H, q, J=7.1 Hz).

(E)-Ethyl 2-(4-(methoxymethoxy)phenyl)-3-phenylhex-2-enoate(3a). A mixture of Ethyl 2-hexynoate (250 mg, 1.78 mmol), 1-iodo-4-(methoxymethoxy)benzene (940 mg, 3.56 mmol), Phenylboronic acid (434 mg, 3.56 mmol) and K$_2$CO$_3$ (492 mg, 3.56 mmol) in DMF (6 ml)-H$_2$O (1.5 ml) was stirred at room temperature for 10 min. Then PdCl$_2$(PhCN)$_2$ (6.8 mg, 0.0177 mmol) was added under Ar atmosphere, and the mixture was stirred at room temperature for 24 h. The reaction was quenched with H$_2$O under ice cooling, and the whole was extracted with Et$_2$O. The organic layer was washed with H$_2$O, brine, dried over Na$_2$SO$_4$, then concentrated. Purification by silica gel flash column chromatography (eluent: hexane/AcOEt, 30:1 to 15:1) gave 3a (29%). 3a: colorless oil; $^1$H-NMR (CDCl$_3$) δ 0.89 (3H, t, J=7.3 Hz), 1.32 (3H, t, J=7.1 Hz), 1.39 (2H, m), 2.58 (2H, m), 3.42 (3H, s), 4.28 (2H, q, J=7.1 Hz), 5.07 (2H, s), 6.75 (2H, d, J=8.8 Hz), 6.90 (2H, d, J=8.8 Hz), 7.04 (2H, m), 7.10-7.20 (3H, m).

Compound 3b~f was prepared by same method as that used for the preparation of 3a.

(E)-Ethyl 2-(4-(methoxymethoxy)phenyl)-4-methyl-3-phenylpent-2-enoate (3b). Purification by silica gel flash column chromatography (eluent: hexane/AcOEt, 30:1 to 10:1) gave 3b (38%). 3b: colorless oil; $^1$H-NMR (CDCl$_3$) δ 1.05 (6H, d, J=6.8 Hz), 1.32 (3H, t, J=7.1 Hz), 3.08 (1H, sep, J=6.8 Hz), 3.40 (3H, s), 4.28 (2H, q, J=7.1 Hz), 5.05 (2H, s), 6.71 (2H, d, J=8.8 Hz), 6.95 (2H, d, J=8.8 Hz), 7.00 (2H, m), 7.12-7.21 (3H, m).

(E)-Ethyl 3-cyclopentyl-2-(4-(methoxymethoxy)phenyl)-3-phenylacrylate (3c). Purification by silica gel flash column chromatography (eluent: hexane/AcOEt, 30:1 to 10:1) gave 3c (29%). 3c: colorless oil; $^1$H-NMR (CDCl$_3$) δ 1.22-1.43 (2H, m), 1.32 (3H, t, J=7.1 Hz), 1.47-1.56 (4H, m), 1.87 (2H, m), 3.05 (1H, m), 3.40 (3H, s), 4.27 (2H, q, J=7.1 Hz), 5.05 (2H, s), 6.71 (2H, d, J=8.8 Hz), 6.94 (2H, d, J=8.8 Hz), 6.99 (2H, m), 7.10-7.19 (3H, m).

Ethyl 2-(4-(methoxymethoxy)phenyl)-3,3-diphenylacrylate (3d). Purification by silica gel flash column chromatography (eluent: hexane/AcOEt, 30:1 to 5:1) gave 3d (62%). 3d: colorless powder; $^1$H-NMR (CDCl$_3$) δ 0.95 (3H, t, J=7.1 Hz), 3.45 (3H, s), 4.01 (2H, q, J=7.1 Hz), 5.12 (2H, s), 6.83 (2H, d, J=9.0 Hz), 7.02 (4H, m), 7.11-7.16 (3H, m), 7.24-7.32 (5H, m).

(Z)-Ethyl 2,3-bis(4-(methoxymethoxy)phenyl)-3-phenylacrylate (3e). Purification by silica gel flash column chromatography (eluent: hexane/AcOEt, 10:1 to 5:1) gave 3e (70%). 3e: colorless powder; $^1$H-NMR (CDCl$_3$) δ 1.02 (3H, t, J=7.1 Hz), 3.45 (3H, s), 3.49 (3H, s), 4.06 (2H, q, J=7.1 Hz), 5.12 (2H, s), 5.18 (2H, s), 6.82 (2H, d, J=9.0 Hz), 6.97 (2H, d, J=8.8 Hz), 7.00 (2H, d, J=9.0 Hz), 7.02 (2H, m), 7.11-7.20 (5H, m).

(E)-Ethyl 5-triisopropylsilyoxy-2-(4-(methoxymethoxy)phenyl)-3-phenylpent-2-enoate (3f). Purification by silica gel flash column chromatography (eluent: hexane/AcOEt, 30:1 to 20:1) gave 3f (37%). 3f: yellow oil; $^1$H-NMR (CDCl$_3$) δ 0.94-1.06 (21H, m), 1.31 (3H, t, J=7.1 Hz), 2.91 (2H, d, J=7.3 Hz), 3.42 (3H, s), 3.70 (2H, t, J=7.3 Hz), 4.27 (2H, q, J=7.1 Hz), 5.07 (2H, s), 6.75 (2H, d, J=9.0 Hz), 6.92 (2H, d, J=9.0 Hz), 7.06 (2H, m), 7.10-7.17 (3H, m).

(E)-2-(4-(methoxymethoxy)phenyl)-3-phenylhex-2-enoic acid (4a). To a solution of 3a (140 mg, 0.395 mmol) in MeOH (5 ml) was added 2N NaOH (2 ml) and the mixture was stirred at 80° C. for 15 h. After cooling, 2 N HCl (2 ml) was added drop wise under ice cooling, and the whole was extracted with AcOEt, the organic layer was washed with brine, dried over Na$_2$SO$_4$, then concentrated. The residual solid was triturated with hexanes to give 4a (78%). 4a: colorless powder; $^1$H-NMR (CDCl$_3$) δ 0.91 (3H, t, J=7.4 Hz), 1.42 (2H, m), 2.76 (2H, m), 3.42 (3H, s), 5.08 (2H, s), 6.78 (2H, d, J=8.8 Hz), 6.94 (2H, d, J=8.8 Hz), 7.01 (2H, m), 7.12-7.18 (3H, m).

Compound 4b~f was prepared by same method as that used for the preparation of 4a.

(E)-2-(4-(methoxymethoxy)phenyl)-4-methyl-3-phenylpent-2-enoic acid(4b). 4b: colorless powder (84%); $^1$H-NMR (CDCl$_3$) δ 1.07 (6H, d, J=6.8 Hz), 3.40 (3H, s), 3.44 (1H, sep, J=6.8 Hz), 5.05 (2H, s), 6.74 (2H, d, J=8.8 Hz), 6.95-6.99 (4H, m), 7.10-7.19 (3H, m).

(E)-3-Cyclopentyl-2-(4-(methoxymethoxy)phenyl)-3-phenylacrylic acid (4c). colorless powder (90%); $^1$H-NMR (CDCl$_3$) δ 1.36 (2H, m), 1.52 (4H, m), 1.90 (2H, m), 3.40 (3H, s), 3.41 (1H, m), 5.05 (2H, s), 6.74 (2H, d, J=8.8 Hz), 6.93-6.98 (4H, m), 7.10-7.18 (3H, m).

2-(4-(methoxymethoxy)phenyl)-3,3-diphenylacrylic acid (4d). colorless powder (93%); $^1$H-NMR (DMSO-d$_6$) δ 3.34 (3H, s), 5.10 (2H, s), 6.74 (2H, m), 6.90 (2H, m), 6.98 (2H, d, J=8.3 Hz), 7.08-7.27 (6H, m), 7.32 (2H, m).

(Z)-2,3-bis(4-(methoxymethoxy)phenyl)-3-phenylacrylic acid (4e). Purification by silica gel flash column chromatography (eluent hexane/AcOEt, 3:1 to AcOEt) gave the colorless solid (84%). The solid was triturated with hexane to give 4e (56%). 4e: colorless powder; $^1$H-NMR (DMSO-d$_6$) δ 3.45 (3H, s), 3.50 (3H, s), 5.12 (2H, s), 5.19 (2H, s), 6.84 (2H, d, J=8.8 Hz), 6.97-7.02 (4H, m), 7.03 (2H, d, J=8.8 Hz), 7.11-7.17 (3H, m), 7.21 (2H, d, J=8.8 Hz).

(E)-5-Triisopropylsilyloxy-2-(4-(methoxymethoxy)phenyl)-3-phenylpent-2-enoic acid (4f). Purification by silica gel flash column chromatography (eluent hexane/AcOEt, 3:1 to 1:1) gave the 4f (27%). 4f: colorless oil; $^1$H-NMR (CDCl$_3$) δ 1.09 (18H, m), 1.13-1.22 (3H, m), 3.03 (2H, t, J=5.5 Hz), 3.42 (3H, s), 3.75 (2H, t, J=5.5 Hz), 5.07 (2H, s), 6.76 (2H, d, J=9.0 Hz), 6.88 (2H, d, J=9.0 Hz), 7.06 (2H, m), 7.10-7.17 (3H, m).

(E)-N-(4-(2-(Dimethylamino)ethoxy)phenyl)-2-(4-(methoxymethoxy)phenyl)-3-phenylhex-2-enamide (5a). To a mixture of 4a (50 mg, 0.153 mmol), 4-(2-(dimethylamino)ethoxy)benzenamine dihydrochloride (42.6 mg, 0.168 mmol), 4-Dimethylaminopyridine (0.9 mg, 0.00736 mmol) in CH$_2$Cl$_2$ (2 ml) was added O-Benzotriazoyl-N,N,N',N'-tetramethyluronium Hexafluorophosphate (60.9 mg, 0.161 mmol) under ice cooling, and the mixture was stirred at 0° C. for 10 min. Then N,N-Diisopropylethylamine (69.2 mg, 0.534 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by silica gel flash column chromatography (eluent: AcOEt to CHCl$_3$/MeOH, 10:1) gave the colorless solid (100%). The solid was triturated with Et$_2$O-hexane to give 5a (84%). 5a: colorless powder; $^1$H-NMR (CDCl$_3$) δ 0.91 (3H, t, J=7.4 Hz), 1.44 (2H, m), 2.43 (6H, s), 2.72 (2H, m), 2.84 (2H, t, J=5.4 Hz), 3.43 (3H, s), 4.10 (2H, t, J=5.4 Hz), 5.08 (2H, s), 6.78 (2H, d, J=8.8 Hz), 6.87 (2H, d, J=9.0 Hz), 7.00 (2H, d, J=8.8 Hz), 7.00 (1H, brs), 7.06 (2H, m), 7.11-7.22 (3H, m), 7.41 (2H, d, J=9.0 Hz).

Compound 5b~f was prepared by same method as that used for the preparation of 5a.

(E)-N-(4-(2-(Dimethylamino)ethoxy)phenyl)-2-(4-(methoxymethoxy)phenyl)-4-methyl-3-phenylpent-2-enamide (5b). Purification by silica gel flash column chromatography (eluent: CH$_2$Cl$_2$ to CH$_2$Cl$_2$/MeOH, 5:1) gave the colorless solid (92%). The solid was triturated with hexane to give 5b (70%). 5b: colorless powder; $^1$H-NMR (CDCl$_3$) δ

1.08 (6H, t, J=6.8 Hz), 2.36 (6H, s), 2.75 (2H, t, J=5.4 Hz), 3.40 (3H, s), 3.48 (1H, m), 4.07 (2H, t, J=5.4 Hz), 5.05 (2H, s), 6.73 (2H, d, J=8.6 Hz), 6.89 (2H, d, J=9.0 Hz), 6.99-7.04 (4H, m), 7.08 (1H, brs), 7.13-7.23 (3H, m), 7.43 (2H, d, J=9.0 Hz).

(E)-N-(4-(2-(Dimethylamino)ethoxy)phenyl)-3-cyclopentyl-2-(4-(methoxymethoxy)phenyl)-3-phenylacrylamide (5c). Purification by silica gel flash column (eluent: AcOEt to CHCl$_3$/MeOH, 5:1) gave the colorless solid (89%). The solid was triturated with Et$_2$O-hexane to give 5c (55%). 5c: colorless powder; $^1$H-NMR (CDCl$_3$) δ 1.34-1.60 (7H, m), 1.85-1.95 (2H, m), 2.34 (6H, s), 2.73 (2H, t, J=5.6 Hz), 3.40 (3H, s), 4.05 (2H, t, J=5.6 Hz), 5.05 (2H, s), 6.73 (2H, d, J=8.8 Hz), 6.89 (2H, d, J=9.0 Hz), 6.99-7.04 (4H, m), 7.10 (1H, brs), 7.13-7.23 (3H, m), 7.43 (2H, d, J=9.0 Hz).

N-(4-(2-(Dimethylamino)ethoxy)phenyl)-2-(4-(methoxymethoxy)phenyl)-3,3-diphenylacrylamide (5d). Purification by silica gel flash column (eluent: AcOEt to CHCl$_3$/MeOH, 10:1) gave the colorless solid (79%). The solid was triturated with Et$_2$O to give 5d (68%). 5d: colorless powder; $^1$H-NMR (CDCl$_3$) δ 2.32 (6H, s), 2.69 (2H, t, J=5.8 Hz), 3.45 (3H, s), 4.00 (2H, t, J=5.8 Hz), 5.12 (2H, s), 6.77 (2H, d, J=9.0 Hz), 6.85 (2H, d, J=8.8 Hz), 6.97 (1H, brs), 7.01-7.05 (4H, m), 7.10 (2H, d, J=8.8 Hz), 7.17 (2H, m), 7.26-7.36 (6H, m).

(Z)-N-(4-(2-(Dimethylamino)ethoxy)phenyl)-2,3-bis(4-(methoxymethoxy)phenyl)-3-phenylacrylamide (5e). Purification by silica gel flash column (eluent: AcOEt to CHCl$_3$/MeOH, 5:1) gave the colorless solid (61%). The solid was triturated with Et$_2$O to give 5e (39%). 5e: colorless powder; $^1$H-NMR (CDCl$_3$) δ 2.33 (6H, s), 2.70 (2H, t, J=5.7 Hz), 3.45 (3H, s), 3.45 (3H, s), 4.01 (2H, t, J=5.7 Hz), 5.12 (2H, s), 5.12 (6H, s), 6.79 (2H, d, J=8.9 Hz), 6.84 (2H, d, J=8.8 Hz), 6.96 (2H, d, J=8.6 Hz), 7.01 (1H, brs), 7.02-7.05 (2H, m), 7.08 (2H, d, J=8.8 Hz), 7.09 (2H, d, J=9.1 Hz), 7.14-7.20 (3H, m), 7.26 (2H, d, J=8.6 Hz).

(E)-N-(4-(2-(Dimethylamino)ethoxy)phenyl)-5-triisopropylsilyloxy-2-(4-(methoxymethoxy)phenyl)-3-phenylpent-2-enamide (5f). Purification by silica gel flash column (eluent: AcOEt to CHCl$_3$/MeOH, 10:1) gave 5f (65%). 5f: colorless powder; $^1$H-NMR (CDCl$_3$) δ 1.00-1.10 (21H, m), 2.37 (6H, s), 2.76 (2H, t, J=5.7 Hz), 3.05 (2H, t, J=5.9 Hz), 3.42 (3H, s), 3.77 (2H, t, J=5.9 Hz), 4.08 (2H, t, J=5.7 Hz), 5.08 (2H, s), 6.77 (2H, d, J=8.8 Hz), 6.90 (2H, d, J=9.1 Hz), 6.96 (2H, d, J=8.8 Hz), 7.10 (2H, m), 7.14-7.18 (3H, m), 7.49 (2H, d, J=9.1 Hz), 8.70 (1H, brs).

(E)-N-(4-(2-(dimethylamino)ethoxy)phenyl)-5-hydroxy-2-(4-(methoxymethoxy)phenyl)-3-phenylpent-2-enamide (5 g). To a solution of 5f (95 mg, 0.147 mmol) in THF (2 ml) was added a 1M solution of tetrabutylammonium fluoride (0.18 ml) in THF under ice cooling, and the mixture was stirred at room temperature for 30 min. H$_2$O was poured into the reaction mixture under ice cooling, and the whole was extracted with AcOEt. The organic layer was washed with brine, dried over Na$_2$SO$_4$, and then concentrated. Purification by silica gel flash column chromatography (eluent: AcOEt to CHCl$_3$/MeOH, 5:1) gave 5 g (90%). 5 g: colorless oil; $^1$H-NMR (CDCl$_3$) δ 2.74 (2H, t, J=5.7 Hz), 3.02 (2H, t, J=5.6 Hz), 3.43 (3H, s), 3.63 (2H, t, J=5.6 Hz), 4.06 (2H, t, J=5.7 Hz), 5.09 (2H, s), 6.79 (2H, d, J=8.3 Hz), 6.88 (2H, d, J=9.1 Hz), 6.99 (2H, d, J=8.6 Hz), 7.09 (2H, m), 7.16-7.21 (3H, m), 7.45 (2H, d, J=8.8 Hz), 7.82 (1H, brs).

(E)-N-(4-(2-(Dimethylamino)ethoxy)phenyl)-2-(4-hydroxyphenyl)-3-phenylhex-2-enamide (6a). To a solution of 5a (45 mg, 0.0921 mmol) in MeOH (1 ml) was added 3N HCl in AcOEt (0.5 ml) under ice cooling, and the mixture was stirred at room temperature for 1 h. A solution of NaHCO$_3$ (139 mg) in H$_2$O was poured into the reaction mixture under ice cooling, and the whole was extracted with AcOEt and a little MeOH. The organic layer was washed with brine, dried over Na$_2$SO$_4$, and then concentrated. The residue was crystallized with Et$_2$O to give 6a (83%). 6a: colorless powder; $^1$H-NMR (CD$_3$OD) δ 0.87 (3H, t, J=7.4 Hz), 1.38 (2H, m), 2.46 (6H, s), 2.59 (2H, m), 2.91 (2H, t, J=5.1 Hz), 4.14 (2H, t, J=5.1 Hz), 6.51 (2H, d, J=8.6 Hz), 6.92-6.96 (4H, m), 7.10-7.24 (5H, m), 7.53 (2H, d, J=8.8 Hz). HRMS calcd for C$_{28}$H$_{33}$N$_2$O$_3$ [M+H]$^+$: 445.2491. Found: 445.2510.

(E)-N-(4-(2-(dimethylamino)ethoxy)phenyl)-2-(4-hydroxyphenyl)-4-methyl-3-phenylpent-2-enamide (6b). To a solution of 5b (90 mg, 0.184 mmol) in MeOH (3 ml) was added 4N HCl in 1,4-dioxane (0.5 ml) under ice cooling, and the mixture was stirred at room temperature for 2 h. A solution of NaHCO$_3$ in H$_2$O was poured into the reaction mixture under ice cooling, and the whole was extracted with AcOEt. The organic layer was washed with brine, dried over Na$_2$SO$_4$, and then concentrated. The residue was crystallized with Et$_2$O to give 6b (84%). 6b: colorless powder; $^1$H-NMR (CD$_3$OD) δ 1.07 (6H, d, J=6.8 Hz), 2.37 (6H, s), 2.79 (2H, t, J=5.4 Hz), 3.12 (1H, sep, J=5.4 Hz), 4.11 (2H, t, J=5.4 Hz), 6.46 (2H, d, J=8.8 Hz), 6.94 (2H, d, J=9.1 Hz), 6.95 (2H, d, J=8.8 Hz), 7.10 (2H, m), 7.16-7.25 (3H, m), 7.52 (2H, d, J=9.1 Hz). HRMS calcd for C$_{28}$H$_{33}$N$_2$O$_3$ [M+H]$^+$: 445.2491. Found: 445.2510.

Compound 6c~e was prepared by same method as that used for the preparation of 6a, 6b.

(E)-N-(4-(2-(Dimethylamino)ethoxy)phenyl)-3-cyclopentyl-2-(4-hydroxyphenyl)-3-phenylacrylamide (6c). 6c: colorless powder (AcOEt, 87%); $^1$H-NMR (CD$_3$OD) δ 1.40-1.58 (6H, m), 1.82-1.92 (2H, m), 2.36 (6H, s), 2.79 (2H, t, J=5.4 Hz), 3.10 (1H, m), 4.10 (2H, t, J=5.4 Hz), 6.45 (2H, d, J=8.9 Hz), 6.94 (2H, d, J=9.1 Hz), 6.95 (2H, d, J=8.9 Hz), 7.09 (2H, m), 7.14-7.24 (3H, m), 7.53 (2H, d, J=9.1 Hz). HRMS calcd for C$_{30}$H$_{35}$N$_2$O$_3$ [M+H]$^+$: 471.2648. Found: 471.2663.

N-(4-(2-(Dimethylamino)ethoxy)phenyl)-2-(4-hydroxyphenyl)-3,3-diphenylacrylamide (6d). 6d: colorless powder (Et$_2$O, 80%); $^1$H-NMR (CD$_3$OD) δ 2.35 (6H, s), 2.77 (2H, t, J=5.4 Hz), 4.06 (2H, t, J=5.4 Hz), 6.59 (2H, d, J=8.6 Hz), 6.99 (2H, d, J=9.2 Hz), 6.95 (2H, d, J=8.8 Hz), 7.07 (2H, m), 7.14 (2H, d, 9.0 Hz), 7.14-7.19 (3H, m), 7.23-7.29 (3H, m), 7.33 (2H, m). HRMS calcd for C$_{31}$H$_{30}$N$_2$O$_3$ [M+H]$^+$: 479.2335. Found: 479.2357.

(Z)-N-(4-(2-(Dimethylamino)ethoxy)phenyl)-2,3-bis(4-hydroxyphenyl)-3-phenylacrylamide (6e). 6e: colorless powder (AcOEt-hexane, 74%); $^1$H-NMR (CD$_3$OD) δ 2.37 (6H, s), 2.80 (2H, t, J=5.4 Hz), 4.07 (2H, t, J=5.4 Hz), 6.56 (2H, d, J=8.6 Hz), 6.67 (2H, d, J=8.8 Hz), 6.84 (2H, d, J=9.1 Hz), 6.96 (2H, d, J=8.6 Hz), 7.07 (2H, m), 7.13-7.19 (5H, m), 7.20 (2H, d, J=9.1 Hz). HRMS calcd for C$_{31}$H$_{31}$N$_2$O$_4$ [M+H]$^+$: 495.2284. Found: 495.2295.

(E)-N-(4-(2-(dimethylamino)ethoxy)phenyl)-5-hydroxy-2-(4-hydroxyphenyl)-3-phenylpent-2-enamide (6f). To a solution of 5 g (60 mg, 0.122 mmol), N,N-Diisopropylethylamine (39.4 mg, 0.305 mmol) in CH$_2$Cl$_2$ (3 ml) was added Acetic anhydride (24.9 mg, 0.243 mmol) under ice cooling, and the mixture was stirred at room temperature for 2 h. H$_2$O was poured into the reaction mixture under ice cooling, and the whole was extracted with CHCl$_3$. The organic layer was washed with brine, dried over Na$_2$SO$_4$, and then concentrated. To a solution of the residue in AcOEt (2 ml) was added 4N HCl in 1,4-dioxane (0.4 ml) and MeOH (0.5 ml) under ice cooling, and the mixture was stirred at room temperature for 1 h. A solution of NaHCO$_3$ in H$_2$O was poured into the reaction mixture under ice cooling, and the whole was extracted with AcOEt. The organic layer was washed with brine, dried over Na$_2$SO$_4$, and then concentrated. To a solution of the residue in MeOH (3 ml) was added 2N NaOH (0.171 ml) under ice cooling, and the mixture was stirred at room temperature for 40 min. 2N HCl (0.170 ml) was added under ice cooling, then NaHCO$_3$ in H$_2$O was poured into the reaction mixture. The whole was extracted with AcOEt, and the organic layer was washed with brine, dried over Na$_2$SO$_4$, and then concentrated. The residue was crystallized with AcOEt to give 6f (48%). 6f: colorless powder; $^1$H-NMR (CD$_3$OD) δ 2.44 (6H, s), 2.88-2.92 (4H, m), 3.56 (2H, t, J=6.6 Hz), 4.14 (2H, t, J=5.4 Hz), 6.51 (2H, d, J=8.8 Hz), 6.89 (2H, d, J=8.8 Hz), 6.95 (2H, d, J=9.1 Hz), 7.14 (2H, m), 7.16-7.24 (3H, m), 7.58 (2H, d, J=9.1 Hz). HRMS calcd for C$_{27}$H$_{31}$N$_2$O$_4$ [M+H]$^+$: 447.2284. Found: 447.2292.

Scheme 8

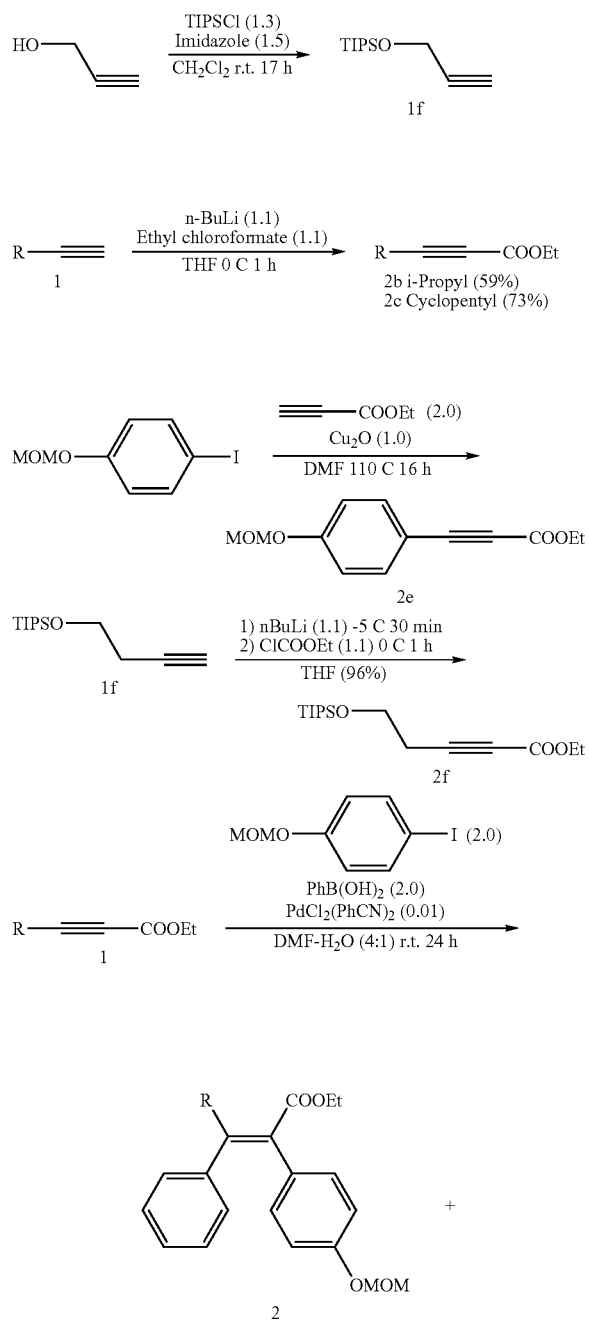
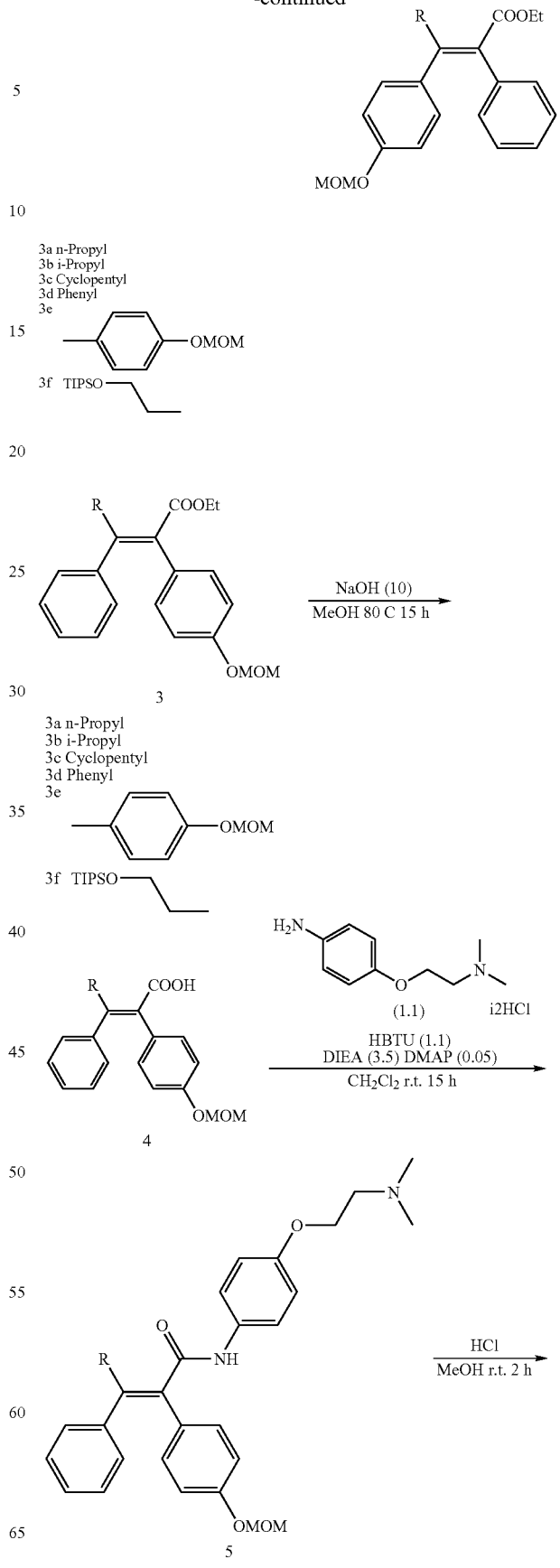

-continued

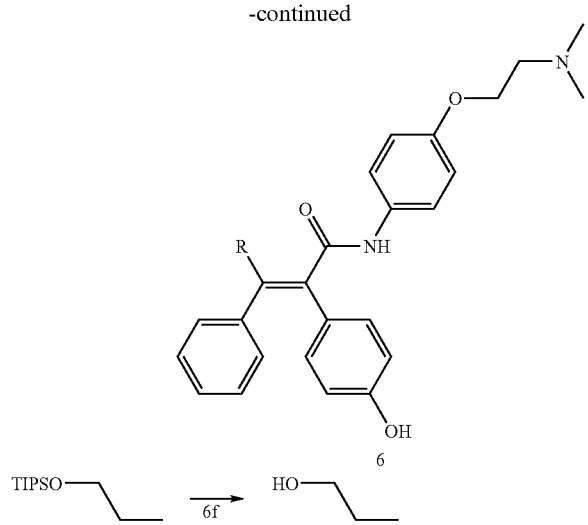

Scheme 9

Ethyl 3-cyclopropylpropiolate (2). Under an Ar atmosphere, to a mixture of Ethynylcyclopropane (1.00 g, 15.1 mmol) in THF (10 ml) was added a solution of 2.5 M n-BuLi in hexanes (6.60 ml, 16.5 mmol) at −78° C. over 15 min, then the mixture was stirred at −78° C. for 5 min, and at −10° C. for 30 min. Ethyl chloroformate (1.89 g, 16.6 mmol) was added drop wise at −78° C., then the mixture was stirred at 0° C. for 1 h. The reaction was quenched with saturated aqueous NH$_4$Cl under ice cooling, and the whole was extracted with Et$_2$O. The organic layer was washed with brine, dried over Na$_2$SO$_4$, and then concentrated. Purification by kugelrohr distillation (5~8 mmHg 100~110° C.) (77%). 2: colorless oil; $^1$H-NMR (CDCl$_3$) δ 0.86-0.98 (4H, m), 1.30 (3H, t, J=7.1 Hz), 1.38 (1H, m), 4.20 (2H, q, J=7.1 Hz).

(E)-Ethyl 3-cyclopropyl-2-(4-(methoxymethoxy)phenyl)-3-phenylacrylate (3) and (E)-Ethyl 3-cyclopropyl-3-(4-(methoxymethoxy)phenyl)-2-phenylacrylate(4). To a mixture of 2 (215 mg, 1.56 mmol), Iodobenzene (637 mg, 3.12 mmol), 4-(methoxymethoxy)phenylboronic acid (568 mg, 3.12 mmol) and K$_2$CO$_3$ (431 mg, 3.12 mmol) in DMF (10 ml)-H$_2$O (2.5 ml) was stirred at room temperature for 10 min. Then PdCl$_2$(PhCN)$_2$ (6.0 mg, 0.0156 mmol) was added under Ar atmosphere, and the mixture was stirred at room temperature for 24 h. The reaction was quenched with H$_2$O under ice cooling, and the whole was extracted with Et$_2$O. The organic layer was washed with H$_2$O, brine, dried over Na$_2$SO$_4$, then concentrated. Purification by silica gel flash column chromatography (eluent: hexane to hexane/AcOEt, 10:1) gave 3 (24%) and 4 (28%). 3: colorless oil; $^1$H-NMR (CDCl$_3$) δ 0.42 (2H, m), 0.77 (2H, m), 1.31 (3H, t, J=7.1 Hz), 2.27 (1H, m), 3.40 (3H, s), 4.29 (2H, q, J=7.1 Hz), 5.05 (2H, s), 6.71 (2H, d, J=9.0 Hz), 6.90 (2H, d, J=9.0 Hz), 6.94 (2H, m), 7.06-7.17 (3H, m). 4: colorless oil; $^1$H-NMR (CDCl$_3$) δ 0.39 (2H, m), 0.62 (2H, m), 0.84 (3H, t, J=7.1 Hz), 1.72 (1H, m), 3.49 (3H, s), 3.83 (2H, q, J=7.1 Hz), 5.18 (2H, s), 6.98 (2H, d, J=8.8 Hz), 7.06 (2H, d, J=8.8 Hz), 7.83 (1H, m), 7.40 (2H, m), 7.49 (2H, m).

(E)-ethyl 3-cyclopropyl-3-(4-(methoxymethoxy)phenyl)-2-phenylacrylate (5). To a mixture of 2 (385 mg, 2.79 mmol), 1-iodo-4-(methoxymethoxy)benzene (1.47 g, 5.57 mmol), Phenylboronic acid (680 mg, 5.58 mmol) and K$_2$CO$_3$ (771 mg, 5.58 mmol) in DMF (8.5 ml)-H$_2$O (2.2 ml) was stirred at room temperature for 10 min. Then PdCl$_2$(PhCN)$_2$ (10.7 mg, 0.0279 mmol) was added under Ar atmosphere, and the mixture was stirred at room temperature for 24 h. The reaction was quenched with H$_2$O under ice cooling, and the whole was extracted with Et$_2$O. The organic layer was washed with H$_2$O, brine, dried over Na$_2$SO$_4$, then concentrated. Purification by silica gel flash column chromatography (eluent: hexane/AcOEt, 30:1 to 10:1) gave 5 (29%). 5: colorless oil; $^1$H-NMR (CDCl$_3$) δ 0.44 (2H, m), 0.79 (2H, m), 1.29 (3H, t, J=7.2 Hz), 2.30 (1H, m), 3.43 (3H, s), 4.28 (2H, q, J=7.1 Hz), 5.08 (2H, s), 6.78 (2H, d, J=8.8 Hz), 6.85 (2H, d, J=8.8 Hz), 6.99 (2H, m), 7.03-7.09 (3H, m).

(E)-3-cyclopropyl-2-(4-(methoxymethoxy)phenyl)-3-phenylacrylic acid (7).

To a solution of 3 (105 mg, 0.298 mmol) in MeOH (3 ml) was added 2N NaOH (1.5 ml), and the mixture was stirred at 80° C. for 24 h. After cooling, 2 N HCl (1.5 ml) was added drop wise under ice cooling, and the whole was extracted with AcOEt, the organic layer was washed with brine, dried over Na$_2$SO$_4$, then concentrated. The residual solid was triturated with hexanes to give 7 (75%). 7: colorless powder; $^1$H-NMR (CDCl$_3$) δ 0.45 (2H, m), 0.83 (2H, m), 2.73 (1H, m), 3.40 (3H, s), 5.04 (2H, s), 6.73 (2H, d, J=9.0 Hz), 6.89 (2H, m), 6.92 (2H, d, J=9.0 Hz), 7.05-7.14 (3H, m).

Compound 10, 13 was prepared by same method as that used for the preparation of 7.

(Z)-3-cyclopropyl-3-(4-(methoxymethoxy)phenyl)-2-phenylacrylic acid (10). colorless powder (58%); $^1$H-NMR (CDCl$_3$) δ 0.40 (2H, m), 0.61 (2H, m), 1.64 (1H, m), 3.50 (3H, s), 5.18 (2H, s), 6.98 (2H, d, J=8.5 Hz), 7.03 (2H, d, J=8.5 Hz), 7.33 (1H, m), 7.39-7.45 (4H, m).

(E)-3-cyclopropyl-3-(4-(methoxymethoxy)phenyl)-2-phenylacrylic acid (13). colorless powder (84%); $^1$H-NMR (CDCl$_3$) δ 0.47 (2H, m), 0.84 (2H, m), 2.74 (1H, m), 3.41 (3H, s), 5.06 (2H, s), 6.76 (2H, d, J=9.0 Hz), 6.80 (2H, d, J=9.0 Hz), 7.00 (2H, m), 7.03-7.11 (3H, m).

(E)-N-(4-(2-(dimethylamino)ethoxy)phenyl)-3-cyclopropyl-2-(4-(methoxymethoxy)phenyl)-3-phenylacrylamide (8). To a mixture of 7 (65 mg, 0.200 mmol), 4-(2-(dimethylamino)ethoxy)benzenamine dihydrochloride (42.6 mg, 0.168 mmol), 4-Dimethylaminopyridine (1.2 mg, 0.00982 mmol) in CH$_2$Cl$_2$ (3 ml) was added O-Benzotriazoyl-N,N,N',N'-tetramethyluronium Hexafluorophosphate (83.4 mg, 0.220 mmol) under ice cooling, and the mixture was stirred at 0° C. for 10 min. Then N,N-Diisopropylethylamine (90.4 mg, 0.701 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by silica gel flash column chromatography (eluent: CH$_2$Cl$_2$ to CH$_2$Cl$_2$/MeOH, 6:1) gave the colorless solid (100%). The solid was triturated with hexane to give 8 (80%). 8: colorless powder; $^1$H-NMR (CDCl$_3$) δ 0.45 (2H, m), 0.79 (2H, m), 2.36 (6H, s), 2.55 (1H, m), 2.76 (2H, t, J=5.5 Hz), 3.41 (3H, s), 4.07 (2H, t, J=5.5 Hz), 5.05 (2H, s), 6.74 (2H, d, J=8.8 Hz), 6.88 (2H, d, J=8.8 Hz), 6.95-6.99 (4H, m), 7.10-7.20 (4H, m), 7.44 (2H, d, J=8.8 Hz).

Compound 11, 14 was prepared by same method as that used for the preparation of 8.

(Z)-N-(4-(2-(dimethylamino)ethoxy)phenyl)-3-cyclopropyl-3-(4-(methoxymethoxy)phenyl)-2-phenylacrylamide (11). Purification by silica gel flash column chromatography (eluent: CH$_2$Cl$_2$ to CH$_2$Cl$_2$/MeOH, 6:1) gave the colorless solid (94%). The solid was triturated with Et₂O-hexane to give 11 (67%). 11: colorless powder; ¹H-NMR (CDCl₃) δ 0.41 (2H, m), 0.65 (2H, m), 1.73 (1 h, m), 2.33 (6H, s), 2.55 (1H, m), 2.70 (2H, brt), 3.46 (3H, s), 3.98 (2H, t, J=5.7 Hz), 5.15 (2H, s), 6.70 (2H, d, J=9.1 Hz), 6.70 (1H, brs), 6.93 (2H, d, J=8.8 Hz), 7.02 (2H, d, J=8.6 Hz), 7.17 (2H, d, J=8.3 Hz), 7.34 (1H, m), 7.43 (2H, t, J=7.5 Hz), 7.56 (2H, m).

(E)-N-(4-(2-(dimethylamino)ethoxy)phenyl)-3-cyclopropyl-3-(4-(methoxymethoxy)phenyl)-2-phenylacrylamide (14). Purification by silica gel flash column chromatography (eluent: AcOEt to CHCl₃/MeOH, 5:1) gave the colorless solid (94%). The solid was triturated with Et₂O-hexane to give 14 (72%). 14: colorless powder; ¹H-NMR (CDCl₃) δ 0.47 (2H, m), 0.81 (2H, m), 2.33 (6H, s), 2.54 (1H, m), 2.72 (2H, t, J=5.7 Hz), 3.44 (3H, s), 4.04 (2H, t, J=5.5 Hz), 5.09 (2H, s), 6.80 (4H, m), 7.04-7.13 (5H, m), 7.17 (1H, brs), 7.43 (2H, d, J=9.1 Hz).

(E)-N-(4-(2-(dimethylamino)ethoxy)phenyl)-3-cyclopropyl-2-(4-hydroxyphenyl)-3-phenylacrylamide (9). To a solution of 8 (70 mg, 0.144 mmol) in MeOH (3 ml) was added 4N HCl in 1,4-dioxane (0.4 ml) under ice cooling, and the mixture was stirred at room temperature for 3 h. A solution of NaHCO₃ in H₂O was poured into the reaction mixture under ice cooling, and the whole was extracted with AcOEt. The organic layer was washed with brine, dried over Na₂SO₄, and then concentrated. The residual solid was crystallized with Et₂O to give 9 (88%). 9: colorless powder; ¹H-NMR (CD₃OD) δ 0.42 (2H, m), 0.73 (2H, m), 1.99 (1H, m), 2.35 (6H, s), 2.77 (2H, t, J=5.4 Hz), 4.10 (2H, t, J=5.4 Hz), 6.47 (2H, d, J=8.8 Hz), 6.91 (2H, d, J=8.8 Hz), 6.94 (2H, d, J=9.1 Hz), 7.06 (2H, m), 7.13-7.23 (3H, m), 7.56 (2H, d, J=9.3 Hz). HRMS calcd for $C_{28}H_{31}N_2O_3$ [M+H]⁺: 443.2335. Found: 443.2353.

Compound 12, 15 was prepared by same method as that used for the preparation of 9.

(Z)-N-(4-(2-(dimethylamino)ethoxy)phenyl)-3-cyclopropyl-3-(4-hydroxyphenyl)-2-phenylacrylamide (12). colorless powder (AcOEt, 78%); ¹H-NMR (CD₃OD) δ 0.39 (2H, m), 0.64 (2H, m), 1.79 (1H, m), 2.31 (6H, s), 2.72 (2H, t, J=5.4 Hz), 4.01 (2H, t, J=5.4 Hz), 6.72 (2H, d, J=8.6 Hz), 6.76 (2H, d, J=9.1 Hz), 7.00 (2H, d, J=9.1 Hz), 7.10 (2H, d, J=8.6 Hz), 7.32 (1H, m), 7.41 (2H, t, J=7.5 Hz), 7.60 (2H, m). HRMS calcd for $C_{28}H_{31}N_2O_3$ [M+H]⁺: 443.2335. Found: 443.2338.

(E)-N-(4-(2-(dimethylamino)ethoxy)phenyl)-3-cyclopropyl-3-(4-hydroxyphenyl)-2-phenylacrylamide (15). colorless powder (AcOEt, 80%); ¹H-NMR (CD₃OD) δ 0.46 (2H, m), 0.75 (2H, m), 1.97 (1H, m), 2.36 (6H, s), 2.79 (2H, t, J=5.5 Hz), 4.10 (2H, t, J=5.5 Hz), 6.60 (2H, d, J=8.8 Hz), 6.87 (2H, d, J=8.6 Hz), 6.94 (2H, d, J=9.1 Hz), 7.02-7.12 (5H, m), 7.57 (2H, d, J=9.1 Hz). HRMS calcd for $C_{28}H_{31}N_2O_3$ [M+H]⁺: 443.2335. Found: 443.2347.

Scheme 9

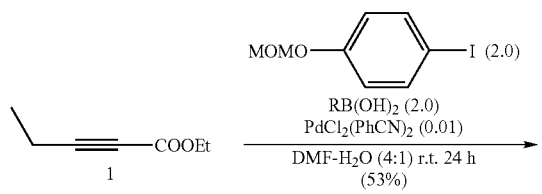

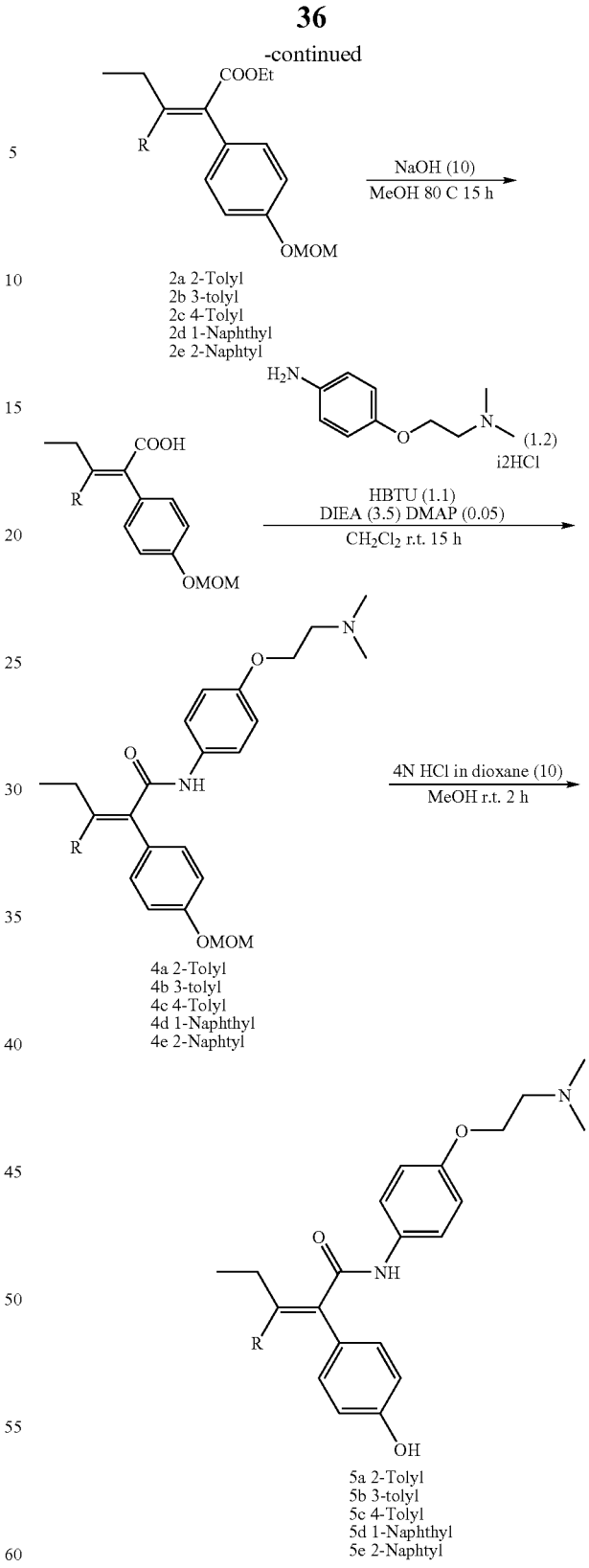

Scheme 10

(E)-ethyl 2-(4-(methoxymethoxy)phenyl)-3-o-tolylpent-2-enoate (2a). A mixture of Ethyl 2-pentynoate (350 mg, 2.77 mmol), 1-iodo-4-(methoxymethoxy)benzene (1.46 g, 5.53 mmol), 2-Methylphenylboronic acid (753 mg, 5.53 mmol)

and K$_2$CO$_3$ (766 mg, 5.54 mmol) in DMF (8.5 ml)-H$_2$O (2.2 ml) was stirred at room temperature for 10 min. Then PdCl$_2$(PhCN)$_2$ (10.6 mg, 0.0276 mmol) was added under Ar atmosphere, and the mixture was stirred at room temperature for 24 h. The reaction was quenched with H$_2$O under ice cooling, and the whole was extracted with Et$_2$O. The organic layer was washed with H$_2$O, brine, dried over Na$_2$SO$_4$, then concentrated. Purification by silica gel flash column chromatography (eluent: hexane/AcOEt, 30:1) gave 2a (27%). 2a: colorless oil; $^1$H-NMR (CDCl$_3$) δ 1.02 (3H, t, J=7.5 Hz), 1.33 (3H, t, J=7.1 Hz), 2.04 (3H, s), 2.56 (2H, m), 3.42 (3H, s), 4.30 (2H, m), 5.06 (2H, s), 6.72 (2H, d, J=8.8 Hz), 6.88 (2H, d, J=8.8 Hz), 7.00-7.12 (5H, m).

Compound 2b-e was prepared by same method as that used for the preparation of 2a.

(E)-ethyl 2-(4-(methoxymethoxy)phenyl)-3-m-tolylpent-2-enoate (2b). Purification by silica gel flash column chromatography (eluent: hexane/AcOEt, 30:1) gave 2b (18%). 2b: colorless oil; $^1$H-NMR (CDCl$_3$) δ 1.00 (3H, t, J=7.4 Hz), 1.32 (3H, t, J=7.1 Hz), 2.22 (3H, s), 2.61 (2H, q, J=7.4 Hz), 3.43 (3H, s), 4.28 (2H, q, J=7.1 Hz), 5.08 (2H, s), 6.76 (2H, d, J=8.6 Hz), 6.81 (1H, m), 6.87 (1H, m), 6.95 (1H, m), 7.04 (1H, t, J=7.5 Hz).

(E)-ethyl 2-(4-(methoxymethoxy)phenyl)-3-p-tolylpent-2-enoate (2c). Purification by silica gel flash column chromatography (eluent: hexane/AcOEt, 30:1) gave 2c (29%). 2c: colorless oil; $^1$H-NMR (CDCl$_3$) δ 0.99 (3H, t, J=7.4 Hz), 1.31 (3H, t, J=7.1 Hz), 2.27 (3H, s), 2.61 (2H, q, J=7.4 Hz), 3.44 (3H, s), 4.28 (2H, q, J=7.1 Hz), 5.09 (2H, s), 6.76 (2H, d, J=9.1 Hz), 6.90-6.94 (4H, m), 6.98 (2H, d, J=8.1 Hz).

(E)-ethyl 2-(4-(methoxymethoxy)phenyl)-3-(naphthalen-1-yl)pent-2-enoate (2d). Purification by Biotage 40M (eluent: hexane to hexane/AcOEt, 10:1) gave 2d (24%). 2d: colorless oil; $^1$H-NMR (CDCl$_3$) δ 1.01 (3H, t, J=7.5 Hz), 1.36 (3H, t, J=7.2 Hz), 2.59 (1H, dq, J=13.3, 7.5 Hz), 2.81 (1H, dq, J=13.3, 7.5 Hz), 3.34 (3H, s), 4.34 (2H, m), 4.96 (2H, s), 6.57 (2H, d, J=8.8 Hz), 6.87 (2H, d, J=9.1 Hz), 7.12 (1H, dd, J=1.3, 7.1 Hz), 7.31 (1H, dd, J=7.1, 8.1 Hz), 7.40-7.46 (2H, m), 7.68 (1H, d, J=8.3 Hz), 7.78 (1H, m), 7.90 (1H, m).

(E)-ethyl 2-(4-(methoxymethoxy)phenyl)-3-(naphthalen-2-yl)pent-2-enoate (2e). Purification by Biotage 40M (eluent: hexane to hexane/AcOEt, 10:1) gave 2e (29%). 2e: colorless oil; $^1$H-NMR (CDCl$_3$) δ 1.02 (3H, t, J=7.4 Hz), 1.34 (3H, t, J=7.1 Hz), 2.73 (2H, q, J=7.4 Hz), 3.39 (3H, s), 4.31 (2H, q, J=7.1 Hz), 5.04 (2H, s), 6.71 (2H, d, J=8.8 Hz), 6.94 (2H, d, J=8.8 Hz), 7.12 (1H, dd, J=1.8, 8.3 Hz), 7.41-7.45 (2H, m), 7.59 (1H, m), 7.62 (1H, d, J=8.6 Hz), 7.69-7.77 (2H, m).

(E)-2-(4-(methoxymethoxy)phenyl)-3-o-tolylpent-2-enoic acid (3a). To a solution of 2a (240 mg, 0.677 mmol) in MeOH (7 ml) was added 2N NaOH (3.4 ml) and the mixture was stirred at 80° C. for 18 h. After cooling, 2 N HCl (3.4 ml) was added drop wise under ice cooling, and the whole was extracted with AcOEt, the organic layer was washed with brine, dried over Na$_2$SO$_4$, then concentrated. The residual solid was triturated with hexanes to give 3a (79%). 3a: colorless powder; $^1$H-NMR (CDCl$_3$) δ 1.05 (3H, t, J=7.5 Hz), 2.08 (3H, s), 2.68 (1H, m), 2.77 (1H, m), 3.41 (3H, s), 5.07 (2H, s), 6.75 (2H, d, J=8.7 Hz), 6.93 (2H, d, J=8.7 Hz), 7.01 (2H, m), 7.05-7.09 (3H, m).

Compound 3b-e was prepared by same method as that used for the preparation of 3a.

(E)-2-(4-(methoxymethoxy)phenyl)-3-m-tolylpent-2-enoic acid (3b). 3b: colorless powder (71%); $^1$H-NMR (CDCl$_3$) δ 1.03 (3H, t, J=7.4 Hz), 2.22 (3H, s), 2.79 (2H, q, J=7.4 Hz), 3.43 (3H, s), 5.09 (2H, s), 6.79 (3H, m), 6.85 (1H, m), 6.94 (3H, m), 7.04 (1H, t, J=7.6 Hz).

(E)-2-(4-(methoxymethoxy)phenyl)-3-p-tolylpent-2-enoic acid (3c). 3c: colorless powder (84%); $^1$H-NMR (CDCl$_3$) δ 1.02 (3H, t, J=7.4 Hz), 2.26 (3H, s), 2.79 (2H, q, J=7.4 Hz), 3.44 (3H, s), 5.10 (2H, s), 6.79 (2H, d, J=8.8 Hz), 6.90 (2H, d, J=8.3 Hz), 6.95 (2H, d, J=8.8 Hz), 6.97 (2H, d, J=8.3 Hz).

(E)-2-(4-(methoxymethoxy)phenyl)-3-(naphthalen-1-yl)pent-2-enoic acid (3d). 3e: colorless powder (83%); $^1$H-NMR (CDCl$_3$) δ 1.05 (3H, t, J=7.5 Hz), 2.70 (1H, dq, J=13.0, 7.5 Hz), 3.08 (2H, dq, J=13.0, 7.5 Hz), 3.34 (3H, s), 4.97 (2H, s), 6.61 (2H, d, J=9.0 Hz), 6.92 (2H, d, J=9.0 Hz), 7.08 (1H, m), 7.30 (1H, m), 7.41-7.49 (2H, m), 7.67 (1H, d, J=8.6 Hz), 7.78 (1H, m), 7.89 (1H, m).

(E)-2-(4-(methoxymethoxy)phenyl)-3-(naphthalen-2-yl)pent-2-enoic acid (3e). 3e: colorless powder (80%); $^1$H-NMR (CDCl$_3$) δ 1.05 (3H, t, J=7.3 Hz), 2.91 (2H, q, J=7.3 Hz), 3.38 (3H, s), 5.04 (2H, s), 6.74 (2H, d, J=8.8 Hz), 6.99 (2H, d, J=8.8 Hz), 7.10 (1H, dd, J=1.6, 8.5 Hz), 7.41-7.45 (4H, m), 7.57 (1H, m), 7.61 (1H, d, J=8.8 Hz), 7.69-7.77 (2H, m).

(E)-N-(4-(2-(dimethylamino)ethoxy)phenyl)-2-(4-(methoxymethoxy)phenyl)-3-o-tolylpent-2-enamide (4a). To a mixture of 3a (90 mg, 0.276 mmol), 4-(2-(dimethylamino)ethoxy)benzenamine dihydrochloride (76.9 mg, 0.304 mmol), 4-Dimethylaminopyridine (1.7 mg, 0.00139 mmol) in CH$_2$Cl$_2$ (3 ml) was added O-Benzotriazoyl-N,N,N',N'-tetramethyluronium Hexafluorophosphate (110 mg, 0.290 mmol) under ice cooling, and the mixture was stirred at 0° C. for 10 min. Then N,N-Diisopropylethylamine (125 mg, 0.965 mmol) was added under ice cooling. The mixture was stirred at 0° C. for 5 min, and at room temperature for 15 h. The reaction was quenched with saturated aqueous NaHCO$_3$ under ice cooling, and the whole was extracted with CHCl$_3$, the organic layer was washed with brine, dried over Na$_2$SO$_4$, and then concentrated. Purification by silica gel flash column chromatography (eluent: AcOEt to CHCl$_3$/MeOH, 10:1) gave colorless solid (97%). The solid was triturated with Et$_2$O-hexane to give 4a (70%). 4a: colorless powder; $^1$H-NMR (CDCl$_3$) δ 1.06 (3H, t, J=7.5 Hz), 2.08 (3H, s), 2.36 (6H, s), 2.71 (2H, q, J=7.5 Hz), 2.75 (2H, t, J=5.6 Hz), 3.42 (3H, s), 4.06 (2H, t, J=5.6 Hz), 5.07 (2H, s), 6.75 (2H, d, J=8.6 Hz), 6.89 (2H, d, J=9.1 Hz), 6.98 (2H, d, J=8.8 Hz), 6.99-7.12 (5H, m), 7.43 (2H, d, J=8.8 Hz).

Compound 4b~e was prepared by same method as that used for the preparation of 4a.

(E)-N-(4-(2-(dimethylamino)ethoxy)phenyl)-2-(4-(methoxymethoxy)phenyl)-3-m-tolylpent-2-enamide (4b). Purification by silica gel flash column chromatography (eluent: AcOEt to CHCl$_3$/MeOH, 10:1) gave colorless solid (90%). The solid was triturated with Et$_2$O-hexane to give 4b (65%). 4b: colorless powder; $^1$H-NMR (CDCl$_3$) δ 1.04 (3H, t, J=7.5 Hz), 2.24 (3H, s), 2.37 (6H, s), 2.72-2.78 (4H, m), 3.43 (3H, s), 4.07 (2H, t, J=5.7 Hz), 5.09 (2H, s), 6.79 (2H, d, J=8.8 Hz), 6.83 (1H, m), 6.88 (2H, d, J=9.1 Hz), 6.90 (1H, m), 6.95-7.03 (2H, m), 7.00 (2H, d, J=8.8 Hz), 7.06 (1H, t, J=7.6 Hz), 7.42 (2H, d, J=9.1 Hz).

(E)-N-(4-(2-(dimethylamino)ethoxy)phenyl)-2-(4-(methoxymethoxy)phenyl)-3-p-tolylpent-2-enamide (4c). Purification by silica gel flash column chromatography (eluent: AcOEt to CHCl$_3$/MeOH, 5:1) gave colorless solid (91%). The solid was triturated with Et$_2$O-hexane to give 4c (63%). 4c: colorless powder; $^1$H-NMR (CDCl$_3$) δ 1.04 (3H, t, J=7.5 Hz), 2.28 (3H, s), 2.34 (6H, s), 2.71-2.77 (4H, m), 3.44 (3H, s), 4.04 (2H, t, J=5.8 Hz), 5.10 (2H, s), 6.79 (2H, d, J=8.9 Hz), 6.88 (2H, d, J=9.1 Hz), 6.95 (2H, d, J=8.3 Hz), 6.98-7.02 (5H, m), 7.41 (2H, d, J=9.1 Hz).

(E)-N-(4-(2-(dimethylamino)ethoxy)phenyl)-2-(4-(methoxymethoxy)phenyl)-3-(naphthalen-1-yl)pent-2-enamide (4d). Purification by Biotage (eluent: CH$_2$Cl$_2$ to CH$_2$Cl$_2$/MeOH, 6:1) gave colorless solid (94%). The solid was triturated with Et$_2$O-hexane to give 4d (68%). 4d: colorless powder; $^1$H-NMR (CDCl$_3$) δ 1.07 (3H, t, J=7.3 Hz), 2.51 (6H, s), 2.73 (1H, m), 2.92 (2H, br), 3.05 (1H, m), 3.35 (3H, s), 4.18 (2H, d, J=5.6 Hz), 4.97 (2H, s), 6.61 (2H, d, J=8.9 Hz), 6.90 (2H, d, J=9.1 Hz), 6.95 (2H, d, J=8.8 Hz), 7.09 (1H, brs), 7.14 (1H, d, J=6.8 Hz), 7.33 (1H, m), 7.41-7.47 (4H, m), 7.68 (1H, m), 7.79 (1H, m), 7.93 (1H, m).

(E)-N-(4-(2-(dimethylamino)ethoxy)phenyl)-2-(4-(methoxymethoxy)phenyl)-3-(naphthalen-2-yl)pent-2-enamide (4e). Purification by Biotage (eluent: CH$_2$Cl$_2$ to CH$_2$Cl$_2$/MeOH, 6:1) gave colorless solid (89%). The solid was triturated with Et$_2$O-hexane to give 4d (76%). 4d: colorless powder; $^1$H-NMR (CDCl$_3$) δ 1.07 (3H, t, J=7.3 Hz), 2.36 (6H, s), 2.75 (2H, t, J=5.6 Hz), 2.87 (2H, q, J=7.3 Hz), 3.39 (3H, s), 4.07 (2H, t, J=5.6 Hz), 5.04 (2H, s), 6.74 (2H, d, J=9.1 Hz), 6.89 (2H, d, J=8.9 Hz), 7.03 (1H, brs), 7.04 (2H, d, J=8.8 Hz), 7.14 (1H, dd, J=1.8, 8.6 Hz), 7.41-7.45 (4H, m), 7.60-7.64 (2H, m), 7.70-7.77 (2H, m).

(E)-N-(4-(2-(dimethylamino)ethoxy)phenyl)-2-(4-hydroxyphenyl)-3-o-tolylpent-2-enamide (5a). To a solution of 4a (75 mg, 0.153 mmol) in MeOH (2 ml) was added 4N HCl in 1,4-dioxane (0.4 ml) under ice cooling, and the mixture was stirred at room temperature for 2 h. A solution of NaHCO$_3$ in H$_2$O was poured into the reaction mixture under ice cooling, and the whole was extracted with AcOEt. The organic layer was washed with brine, dried over Na$_2$SO$_4$, and then concentrated. The residual was crystallized with AcOEt to give 5a (74%). 5a: colorless powder; $^1$H-NMR (CD$_3$OD) δ 0.97 (3H, t, J=7.5 Hz), 2.09 (3H, s), 2.37 (6H, s), 2.58 (2H, q, J=7.5 Hz), 2.80 (2H, t, J=5.5 Hz), 4.11 (2H, t, J=5.5 Hz), 6.47 (2H, d, J=8.8 Hz), 6.90 (2H, d, J=9.1 Hz), 6.94 (2H, d, J=9.1 Hz), 7.05-7.15 (4H, m), 7.53 (2H, d, J=9.1 Hz). HRMS calcd for C$_{28}$H$_{33}$N$_2$O$_3$ [M+H]$^+$: 445.2491. Found: 445.2497.

Compound 5b-e was prepared by same method as that used for the preparation of 5a.

(E)-N-(4-(2-(dimethylamino)ethoxy)phenyl)-2-(4-hydroxyphenyl)-3-m-tolylpent-2-enamide (5b). 5b: colorless powder (AcOEt, 86%); $^1$H-NMR (CD$_3$OD) δ 0.97 (3H, t, J=7.4 Hz), 2.23 (3H, s), 2.36 (6H, s), 2.62 (2H, q, J=7.4 Hz), 2.79 (2H, t, J=5.4 Hz), 4.10 (2H, t, J=5.4 Hz), 6.51 (2H, d, J=8.9 Hz), 6.90-6.95 (5H, m), 6.96-7.01 (2H, m), 7.09 (1H, t, J=7.6 Hz), 7.53 (2H, d, J=9.1 Hz). HRMS calcd for C$_{28}$H$_{33}$N$_2$O$_3$ [M+H]$^+$: 445.2491. Found: 445.2506.

(E)-N-(4-(2-(dimethylamino)ethoxy)phenyl)-2-(4-hydroxyphenyl)-3-p-tolylpent-2-enamide (5c). 5c: colorless powder (AcOEt, 74%); $^1$H-NMR (CD$_3$OD) δ 0.96 (3H, t, J=7.4 Hz), 2.28 (3H, s), 2.36 (6H, s), 2.62 (2H, q, J=7.4 Hz), 2.79 (2H, t, J=5.4 Hz), 4.10 (2H, t, J=5.4 Hz), 6.51 (2H, d, J=8.8 Hz), 6.92 (2H, d, J=8.8 Hz), 6.94 (2H, d, J=9.1 Hz), 7.00-7.05 (4H, m), 7.52 (2H, d, J=9.3 Hz). HRMS calcd for C$_{28}$H$_{33}$N$_2$O$_3$ [M+H]$^+$: 445.2491. Found: 445.2504.

(E)-N-(4-(2-(dimethylamino)ethoxy)phenyl)-2-(4-hydroxyphenyl)-3-(naphthalen-1-yl)pent-2-enamide (5d). 5c: colorless powder (AcOEt-hexane, 77%); $^1$H-NMR (CD$_3$OD) δ 0.96 (3H, t, J=7.5 Hz), 2.38 (6H, s), 2.67 (1H, dq, J=13.6, 7.5 Hz), 2.78 (1H, dq, J=13.6, 7.5 Hz), 2.81 (2H, d, J=5.4 Hz), 4.10 (2H, t, J=5.4 Hz), 6.33 (2H, d, J=8.8 Hz), 6.88 (2H, d, J=9.1 Hz), 6.97 (2H, d, J=9.1 Hz), 7.26 (1H, d, J=7.1 Hz), 7.39 (1H, m), 7.42-7.46 (2H, m), 7.58 (1H, d, J=9.1 Hz), 7.74 (1H, d, J=8.3 Hz), 7.81 (1H, m). HRMS calcd for C$_{31}$H$_{33}$N$_2$O$_3$ [M+H]$^+$: 481.2491. Found: 481.2493.

(E)-N-(4-(2-(dimethylamino)ethoxy)phenyl)-2-(4-hydroxyphenyl)-3-(naphthalen-2-yl)pent-2-enamide (5e). 5e: colorless powder (AcOEt-hexane, 83%); $^1$H-NMR (CD$_3$OD) δ 1.01 (3H, t, J=7.5 Hz), 2.37 (6H, s), 2.76 (2H, q, J=7.5 Hz), 2.80 (2H, d, J=5.5 Hz), 4.12 (2H, t, J=5.5 Hz), 6.48 (2H, d, J=8.6 Hz), 6.93-6.97 (4H, m), 7.23 (1H, d, J=8.6 Hz), 7.40-7.44 (2H, m), 7.55 (2H, d, J=9.1 Hz), 7.66-7.70 (2H, m), 7.72 (1H, m), 7.77 (1H, m). HRMS calcd for C$_{31}$H$_{33}$N$_2$O$_3$ [M+H]$^+$: 481.2491. Found: 481.2499.

Scheme 10

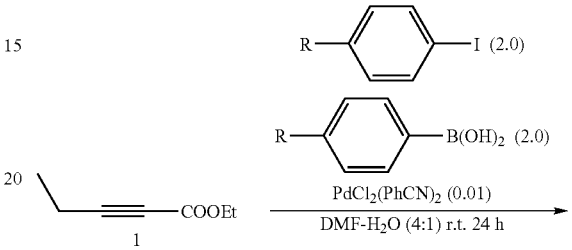

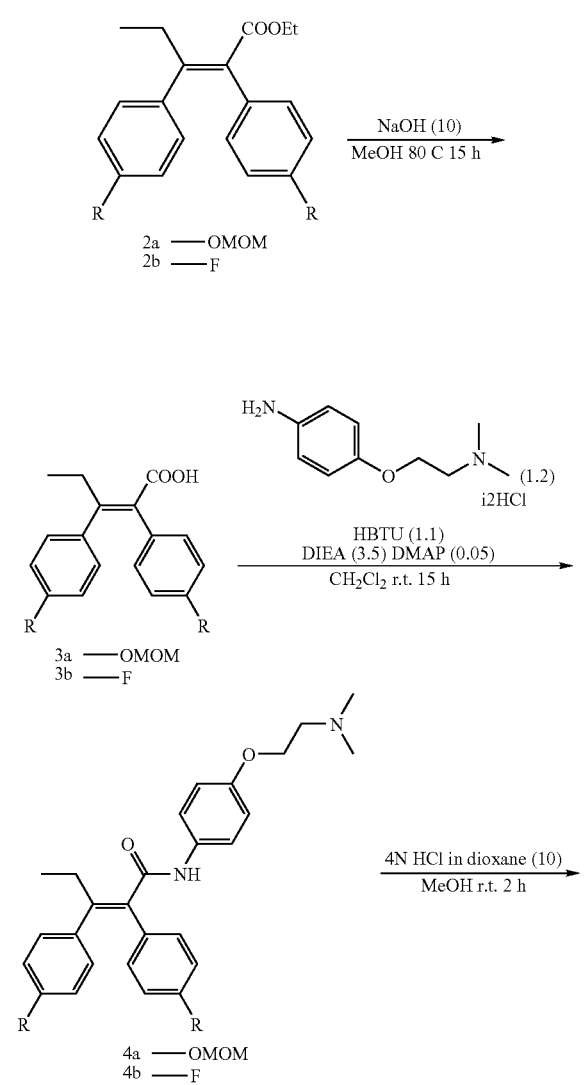

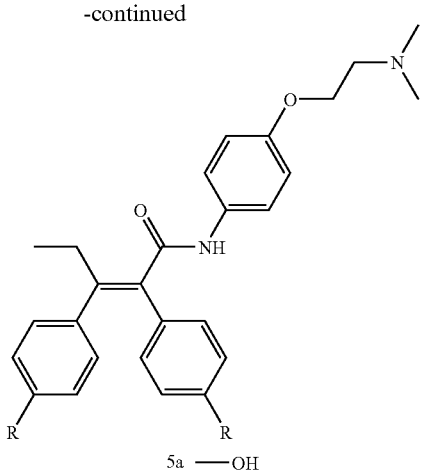

5a —— OH

Scheme 11

(E)-ethyl 2,3-bis(4-(methoxymethoxy)phenyl)pent-2-enoate(2a). To a mixture of Ethyl 2-pentynoate (250 mg, 1.98 mmol), 1-iodo-4-(methoxymethoxy)benzene (1.05 g, 3.98 mmol), 4-(methoxymethoxy)phenylboronic acid (721 mg, 3.96 mom) in DMF (12 ml) was added a solution of $K_2CO_3$ (547 mg, 3.96 mom) in $H_2O$ (3 ml) under ice cooling, then the mixture was stirred at room temperature for 10 min. $PdCl_2(PhCN)_2$ (7.6 mg, 0.0198 mmol) was added under Ar atmosphere, and the mixture was stirred at room temperature for 24 h. The reaction was quenched with $H_2O$ under ice cooling, and the whole was extracted with $Et_2O$. The organic layer was washed with $H_2O$, brine, dried over $Na_2SO_4$, then concentrated. Purification by silica gel flash column chromatography (eluent: hexane/AcOEt, 20:1 to 10:1) gave 2a (59%). 2a: colorless oil; $^1$H-NMR (CDCl$_3$) δ 1.00 (3H, t, J=7.4), 1.31 (3H, t, J=7.1 Hz), 2.60 (2H, q, J=7.4 Hz), 3.44 (3H, s), 3.46 (3H, s), 4.27 (2H, q, J=7.1 Hz), 5.09 (2H, s), 5.12 (2H, s), 6.77 (2H, d, J=8.4 Hz), 6.83 (2H, d, J=8.4 Hz), 6.91 (2H, d, J=8.2 Hz), 6.96 (2H, d, J=8.4 Hz).

(E)-ethyl 2,3-bis(4-fluorophenyl)pent-2-enoate (2b). Compound 2b was prepared by same method as that used for the preparation of 2a. Purification by silica gel flash column chromatography (eluent: hexane/AcOEt, 30:1) gave 2b (43%). 2b: colorless oil; $^1$H-NMR (CDCl$_3$) δ 1.01 (3H, t, J=7.4), 1.30 (3H, t, J=7.1 Hz), 2.65 (2H, q, J=7.4 Hz), 4.27 (2H, q, J=7.1 Hz), 6.80 (2H, t, J=8.6 Hz), 6.86 (2H, t, J=8.6 Hz), 6.92-7.00 (4H, m).

(E)-2,3-bis(4-(methoxymethoxy)phenyl)pent-2-enoic acid (3a). To a solution of 2a (420 mg, 1.05 mmol) in MeOH (10 ml) was added 2N NaOH (5.3 ml), and the mixture was stirred at 80° C. for 15 h. After cooling, 2 N HCl (5.3 ml) was added drop wise under ice cooling, and the whole was extracted with AcOEt, the organic layer was washed with brine, dried over $Na_2SO_4$, then concentrated. The residual solid was triturated with hexanes to give 3a (86%). 3a: colorless powder; $^1$H-NMR (CDCl$_3$) $^1$H-NMR (CDCl$_3$) δ 1.02 (3H, t, J=7.4), 2.77 (2H, q, J=7.4 Hz), 3.43 (3H, s), 3.45 (3H, s), 5.09 (2H, s), 5.11 (2H, s), 6.79 (2H, d, J=8.8 Hz), 6.82 (2H, d, J=8.8 Hz), 6.94 (2H, d, J=8.8 Hz), 6.94 (2H, d, J=8.6 Hz).

(E)-2,3-bis(4-fluorophenyl)pent-2-enoic acid (3b). Compound 3b was prepared by same method as that used for the preparation of 3a. 3b: colorless powder (86%); $^1$H-NMR (CDCl$_3$) δ 1.03 (3H, t, J=7.4), 2.82 (2H, q, J=7.4 Hz), 6.83 (2H, t, J=8.7 Hz), 6.86 (2H, t, J=8.8 Hz), 6.93-7.00 (4H, m).

(E)-N-(4-(2-(dimethylamino)ethoxy)phenyl)-2,3-bis(4-(methoxymethoxy)phenyl)pent-2-enamide (4a). To a mixture of 3a (150 mg, 0.403 mmol), 4-(2-(dimethylamino)ethoxy)benzenamine dihydrochloride (112 mg, 0.442 mmol), 4-Dimethylaminopyridine (2.5 mg, 0.0205 mmol) in $CH_2Cl_2$ (5 ml) was added O-Benzotriazoyl-N,N,N',N'-tetramethyluronium Hexafluorophosphate (160 mg, 0.422 mmol) under ice cooling, and the mixture was stirred at 0° C. for 10 min. Then N,N-Diisopropylethylamine (182 mg, 1.41 mmol) was added under ice cooling. The mixture was stirred at 0° C. for 5 min, and at room temperature for 15 h. The reaction was quenched with saturated aqueous $NaHCO_3$ under ice cooling, and the whole was extracted with $CHCl_3$, the organic layer was washed with brine, dried over $Na_2SO_4$, and then concentrated. Purification by silica gel flash column chromatography (eluent: AcOEt to $CHCl_3$/MeOH, 10:1) gave the colorless solid (84%). The solid was triturated with $Et_2O$-hexane to give 4a (77%). 4a: colorless powder; $^1$H-NMR (CDCl$_3$) δ 1.04 (3H, t, J=7.4), 2.33 (6H, s), 2.71 (2H, t, J=5.7 Hz), 2.74 (2H, q, J=7.4 Hz), 3.44 (3H, s), 3.47 (3H, s), 4.04 (2H, t, J=5.7 Hz), 5.10 (2H, s), 5.13 (2H, s), 6.80 (2H, d, J=8.6 Hz), 6.85 (2H, d, J=8.8 Hz), 6.88 (2H, d, J=9.0 Hz), 6.98 (2H, d, J=8.8 Hz), 7.00 (1H, brs), 7.01 (2H, d, J=8.8 Hz), 7.40 (2H, d, J=9.0 Hz).

(E)-N-(4-(2-(dimethylamino)ethoxy)phenyl)-2,3-bis(4-fluorophenyl)pent-2-enamide (4b). Compound 4b was prepared by same method as that used for the preparation of 4a. Purification by silica gel flash column chromatography (eluent: $CHCl_3$/MeOH, 20:1) gave the colorless oil (94%). The residue was crystallized with $Et_2O$-hexane to give 4b (65%). 4b: colorless powder; $^1$H-NMR (CDCl$_3$) δ 1.04 (3H, t, J=7.3), 2.36 (6H, s), 2.72-2.80 (4H, m), 4.06 (2H, t, J=5.6 Hz), 6.82-6.91 (6H, m), 6.95 (1H, brs), 6.98-7.07 (4H, m), 7.40 (2H, d, J=9.2 Hz). HRMS calcd for $C_{27}H_{29}F_2N_2O_2$ [M+H]$^+$: 451.2197. Found: 451.2215.

(E)-N-(4-(2-(dimethylamino)ethoxy)phenyl)-2,3-bis(4-hydroxyphenyl)pent-2-enamide (5). To a solution of 4a (45 mg, 0.0842 mmol) in MeOH (1 ml) was added 3N HCl in AcOEt (0.5 ml) under ice cooling, and the mixture was stirred at room temperature for 2 h. A solution of $NaHCO_3$ (126 mg) in $H_2O$ was poured into the reaction mixture under ice cooling, and the whole was extracted with AcOEt and a little MeOH. The organic layer was washed with brine, dried over $Na_2SO_4$, and then concentrated. The residual solid was crystallized with $Et_2O$ to give 5 (68%). 5: colorless powder; $^1$H-NMR (CD$_3$OD) δ 0.98 (3H, t, J=7.4 Hz), 2.45 (6H, s), 2.61 (2H, q, J=7.4 Hz), 2.90 (2H, t, J=5.3 Hz), 4.14 (2H, t, J=5.3 Hz), 6.54 (2H, d, J=8.8 Hz), 6.63 (2H, d, J=8.6 Hz), 6.92-6.97 (6H, m), 7.52 (2H, d, J=9.0 Hz). HRMS calcd for $C_{27}H_{31}N_2O_4$ [M+H]$^+$: 447.2284. Found: 447.2298.

Scheme 11

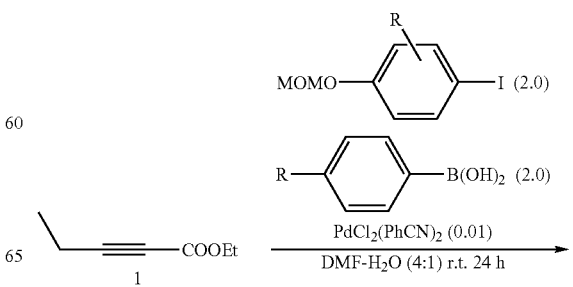

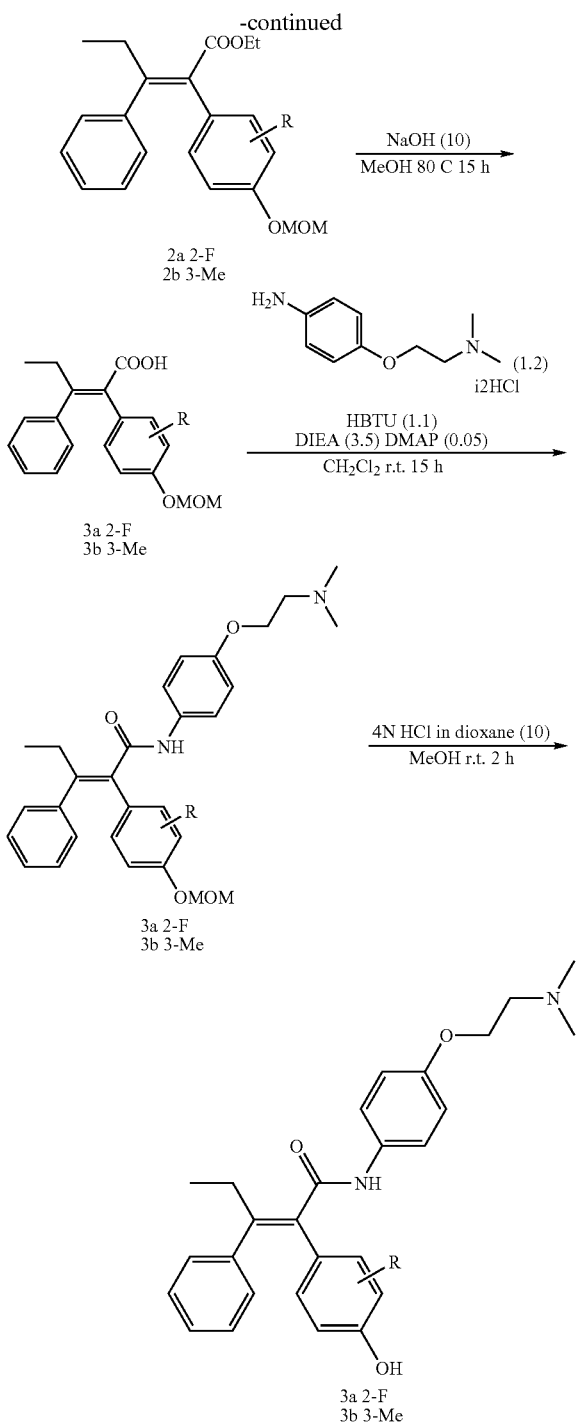

2a 2-F
2b 3-Me 3a 2-F
3b 3-Me 3a 2-F
3b 3-Me 3a 2-F
3b 3-Me

Scheme 12

(E)-ethyl 2-(3-(methoxymethoxy)phenyl)-3-phenylpent-2-enoate (2a). A mixture of Ethyl 2-pentynoate (350 mg, 2.77 mmol), 1-iodo-3-(methoxymethoxy)benzene (1.46 g, 5.53 mmol), Phenylboronic acid (675 mg, 5.54 mmol) and $K_2CO_3$ (766 mg, 5.54 mmol) in DMF (8 ml)-$H_2O$ (2 ml) was stirred at room temperature for 10 min. Then $PdCl_2(PhCN)_2$ (10.6 mg, 0.0276 mmol) was added under Ar atmosphere, and the mixture was stirred at room temperature for 24 h. The reaction was quenched with $H_2O$ under ice cooling, and the whole was extracted with $Et_2O$. The organic layer was washed with $H_2O$, brine, dried over $Na_2SO_4$, then concentrated. Purification by Biotage HPFC (eluent: hexane to hexane/AcOEt, 10:1) gave 2a (25%). 2a: colorless oil; $^1$H-NMR (CDCl$_3$) δ 1.02 (3H, t, J=7.4 Hz), 1.31 (3H, t, J=7.2 Hz), 2.65 (2H, t, J=7.4 Hz), 3.33 (3H, s), 4.29 (2H, t, J=7.2 Hz), 4.91 (2H, s), 6.65 (1H, m), 6.68 (1H, m), 6.74 (1H, ddd, J=1.0, 2.5, 8.3 Hz), 7.00-7.05 (3H, m), 7.10-7.19 (3H, m).

Compound 2b~c was prepared by same method as that used for the preparation of 2a.

(E)-ethyl 2-(4-(methoxymethoxy)-2-methylphenyl)-3-phenylpent-2-enoate (2b). Purification by Biotage HPFC (eluent: hexane to hexane/AcOEt, 10:1) gave 2b (16%). 2b: colorless oil; $^1$H-NMR (CDCl$_3$) δ 1.06 (3H, t, J=7.4 Hz), 1.26 (3H, t, J=7.1 Hz), 2.12 (3H, s), 2.75 (2H, t, J=7.4 Hz), 3.42 (3H, s), 4.21 (2H, t, J=7.1 Hz), 5.06 (2H, s), 6.60 (1H, dd, J=2.8, 8.3 Hz), 6.66 (1H, d, J=2.8 Hz), 6.85 (1H, d, J=8.3 Hz), 6.97 (2H, m), 7.05-7.13 (3H, m).

(E)-ethyl 2-(3-fluoro-4-(methoxymethoxy)phenyl)-3-phenylpent-2-enoate (2c). Purification by Biotage HPFC (eluent: hexane/$CH_2Cl_2$, 1:1 to $CH_2Cl_2$) gave 2c (21%). 2c: colorless oil; $^1$H-NMR (CDCl$_3$) δ 1.01 (3H, t, J=7.5 Hz), 1.32 (3H, t, J=7.1 Hz), 2.64 (2H, t, J=7.5 Hz), 3.46 (3H, s), 4.28 (2H, t, J=7.1 Hz), 5.11 (2H, s), 6.67 (1H, m), 6.73 (1H, dd, J=2.0, 12.4 Hz), 6.90 (1H, t, J=8.6 Hz), 7.03 (2H, m), 7.15-7.21 (3H, m).

(E)-2-(3-(methoxymethoxy)phenyl)-3-phenylpent-2-enoic acid (3a). To a solution of 2a (195 mg, 0.573 mmol) in MeOH (6 ml) was added 2N NaOH (3 ml) and the mixture was stirred at 80° C. for 15 h. After cooling, 2 N HCl (3 ml) was added drop wise under ice cooling, and the whole was extracted with AcOEt, the organic layer was washed with brine, dried over $Na_2SO_4$, then concentrated. The residual solid was triturated with hexanes to give 3a (69%). 3a: colorless powder; $^1$H-NMR (CDCl$_3$) δ 1.04 (3H, t, J=7.5 Hz), 2.83 (2H, t, J=7.5 Hz), 3.34 (3H, s), 4.93 (2H, s), 6.68 (1H, m), 6.73 (1H, d, J=7.6 Hz), 6.77 (2H, dd, J=2.5, 7.8 Hz), 7.01-7.07 (3H, m), 7.10-7.18 (3H, m).

Compound 3b~c was prepared by same method as that used for the preparation of 3a.

(E)-2-(4-(methoxymethoxy)-2-methylphenyl)-3-phenylpent-2-enoic acid (3b). 3b: colorless powder (60%); $^1$H-NMR (CDCl$_3$) δ 1.07 (3H, t, J=7.5 Hz), 2.17 (3H, s), 2.91 (2H, m), 3.42 (3H, s), 5.06 (2H, s), 6.61 (1H, t, J=2.5, 8.6 Hz), 6.70 (1H, d, J=2.5 Hz), 6.83 (1H, d, J=8.3 Hz), 6.96 (2H, m), 7.07-7.15 (3H, m).

(E)-2-(3-fluoro-4-(methoxymethoxy)phenyl)-3-phenylpent-2-enoic acid (3c). 3c: colorless powder (82%); $^1$H-NMR (CDCl$_3$) δ 1.03 (3H, t, J=7.5 Hz), 2.82 (2H, q, J=7.5 Hz), 3.46 (3H, s), 5.12 (2H, s), 6.71 (1H, m), 6.77 (1H, d, J=2.0, 12.1 Hz), 6.93 (1H, t, J=8.5 Hz), 7.01 (2H, m), 7.13-7.21 (3H, m).

(E)-N-(4-(2-(dimethylamino)ethoxy)phenyl)-2-(3-(methoxymethoxy)phenyl)-3-phenylpent-2-enamide (4a). To a mixture of 3a (70 mg, 0.224 mmol), 4-(2-(dimethylamino)ethoxy)benzenamine dihydrochloride (62.4 mg, 0.246 mmol), 4-Dimethylaminopyridine (1.4 mg, 0.0115 mmol) in $CH_2Cl_2$ (3 ml) was added O-Benzotriazoyl-N,N,N',N'-tetramethyluronium Hexafluorophosphate (93.4 mg, 0.246 mmol) under ice cooling, and the mixture was stirred at 0° C. for 10 min. Then N,N-Diisopropylethylamine (101 mg, 0.781 mmol) was added under ice cooling. The mixture was stirred at 0° C. for 5 min, and at room temperature for 15 h. The reaction was quenched with saturated aqueous $NaHCO_3$ under ice cooling, and the whole was extracted with $CHCl_3$, the organic layer was washed with brine, dried over $Na_2SO_4$, and then concentrated. Purification by Biotage HPFC (eluent: $CH_2Cl_2$ to $CH_2Cl_2$/MeOH, 6:1) gave the colorless solid (99%). The solid was triturated with $Et_2O$-hexane to give 4a (65%). 4a: colorless powder; $^1$H-NMR (CDCl$_3$) δ 1.06 (3H, t, J=7.4 Hz), 2.36 (6H, s), 2.75 (2H, t, J=5.4 Hz), 2.79 (2H, t, J=7.4 Hz), 3.34 (3H, s), 4.07 (2H, t, J=5.4 Hz), 4.90 (2H, s), 6.71 (1H, m), 6.77 (1H, ddd, J=1.0, 2.5, 8.1 Hz), 6.81 (1H, m), 6.88 (2H, d, J=9.1 Hz), 7.02 (1H, brs), 7.05-7.09 (3H, m), 7.12-7.21 (3H, m), 7.41 (2H, d, J=8.8 Hz).

Compound 4b~c was prepared by same method as that used for the preparation of 4a.

(E)-N-(4-(2-(dimethylamino)ethoxy)phenyl)-2-(4-(methoxymethoxy)-2-methylphenyl)-3-phenylpent-2-enamide (4b). Purification by Biotage HPFC (eluent: $CH_2Cl_2$ to $CH_2Cl_2$/MeOH, 6:1) gave the colorless solid (86%). The solid was triturated with $Et_2O$-hexane to give 4b (68%). 4b: colorless powder; $^1$H-NMR (CDCl$_3$) δ 1.12 (3H, t, J=7.3 Hz), 2.24 (3H, s), 2.54 (6H, s), 2.96 (4H, m), 3.44 (3H, s), 4.18 (2H, brt), 5.08 (2H, s), 6.62 (1H, m), 6.76 (1H, m), 6.84 (2H, d, J=8.8 Hz), 6.84 (1H, m), 6.90 (1H, brs), 6.97 (2H, m), 7.06-7.14 (3H, m), 7.33 (2H, d, J=8.8 Hz).

(E)-N-(4-(2-(dimethylamino)ethoxy)phenyl)-2-(3-fluoro-4-(methoxymethoxy)phenyl)-3-phenylpent-2-enamide (4c). Purification by Biotage HPFC (eluent: $CH_2Cl_2$ to $CH_2Cl_2$/MeOH, 6:1) gave pale yellow solid (89%). The solid was triturated with hexane to give 4c (70%). 4c: colorless powder; $^1$H-NMR (CDCl$_3$) δ 1.04 (3H, t, J=7.5 Hz), 2.36 (6H, s), 2.72-2.78 (4H, m), 3.47 (3H, s), 4.07 (2H, t, J=5.7 Hz), 5.13 (2H, s), 6.78-6.83 (2H, m), 6.89 (2H, d, J=9.1 Hz), 6.94 (1H, t, J=8.7 Hz), 7.01 (1H, brs), 7.06 (2H, m), 7.14-7.24 (3H, m), 7.42 (2H, d, J=9.1 Hz).

(E)-N-(4-(2-(dimethylamino)ethoxy)phenyl)-2-(3-hydroxyphenyl)-3-phenylpent-2-enamide (5a). To a solution of 4a (50 mg, 0.105 mmol) in MeOH (2 ml) was added 4N HCl in 1,4-dioxane (0.26 ml) under ice cooling, and the mixture was stirred at room temperature for 3 h. A solution of $NaHCO_3$ in $H_2O$ was poured into the reaction mixture under ice cooling, and the whole was extracted with AcOEt. The organic layer was washed with brine, dried over $Na_2SO_4$, and then concentrated. The residual was crystallized with AcOEt to give 5a (73%). 5a: colorless powder; $^1$H-NMR (CD$_3$OD) δ 0.97 (3H, t, J=7.5 Hz), 2.36 (6H, s), 2.66 (2H, q, J=7.5 Hz), 2.79 (2H, t, J=5.4 Hz), 4.10 (2H, t, J=5.4 Hz), 6.52 (1H, dd, J=1.0, 8.1 Hz), 6.57 (1H, m), 6.64 (1H, m), 6.90 (1H, t, J=7.8 Hz), 6.94 (2H, d, J=9.1 Hz), 7.13-7.23 (5H, m), 7.53 (2H, d, J=9.1 Hz). HRMS calcd for $C_{27}H_{31}N_2O_3$ [M+H]$^+$: 431.2335. Found: 431.2336.

Compound 5b~c was prepared by same method as that used for the preparation of 5a.

(E)-N-(4-(2-(dimethylamino)ethoxy)phenyl)-2-(4-hydroxy-2-methylphenyl)-3-phenylpent-2-enamide (5b). 5b: colorless powder (AcOEt-Et$_2$O, 80%); $^1$H-NMR (CD$_3$OD) δ 1.04 (3H, t, J=7.3 Hz), 2.10 (3H, s), 2.36 (6H, s), 2.74-2.80 (4H, m), 4.10 (2H, t, J=5.4 Hz), 6.41 (1H, dd, J=2.5, 8.1 Hz), 6.45 (1H, d, J=2.5 Hz), 6.92 (2H, d, J=9.1 Hz), 6.99 (1H, d, J=8.1 Hz), 7.06-7.16 (5H, m), 7.44 (2H, d, J=9.1 Hz). HRMS calcd for $C_{28}H_{33}N_2O_3$ [M+H]$^+$: 445.2491. Found: 445.2298.

(E)-N-(4-(2-(dimethylamino)ethoxy)phenyl)-2-(3-fluoro-4-hydroxyphenyl)-3-phenylpent-2-enamide (5c). 5c: colorless powder (AcOEt, 71%); $^1$H-NMR (CD$_3$OD) δ 0.98 (3H, t, J=7.4 Hz), 2.36 (6H, s), 2.64 (2H, q, J=7.4 Hz), 2.78 (2H, t, J=5.4 Hz), 4.11 (2H, t, J=5.4 Hz), 6.64 (1H, t, J=8.8 Hz), 6.70-6.76 (2H, m), 6.94 (2H, d, J=9.1 Hz), 7.14 (2H, m), 7.18-7.28 (3H, m), 7.53 (2H, d, J=9.1 Hz). HRMS calcd for $C_{27}H_{30}FN_2O_3$ [M+H]$^+$: 449.2240. Found: 449.2258.

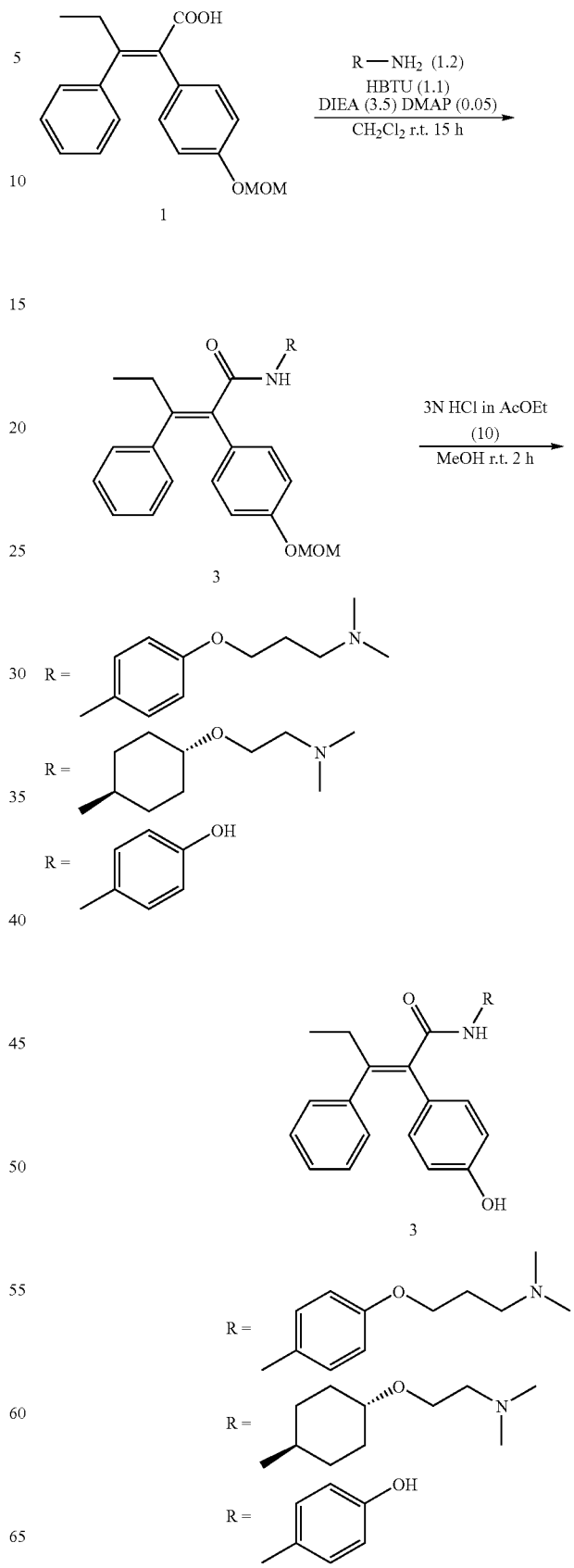

Scheme 12

| Compound | Structure | Name | Category |
|---|---|---|---|
| 1 | 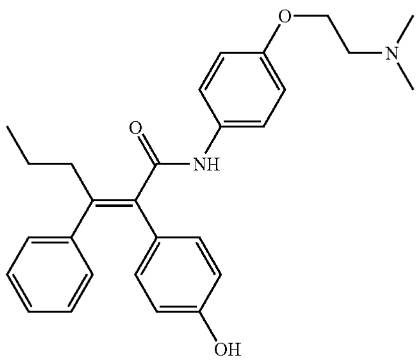 | A071A | A |
| 2 | 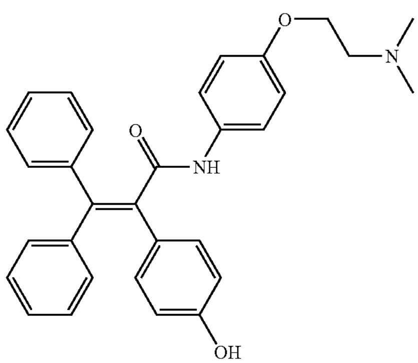 | A075A | A |
| 3 | 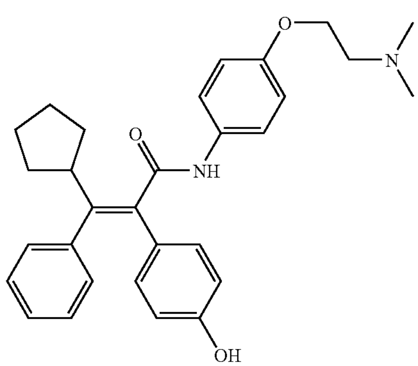 | A144A | A |
| 4 | 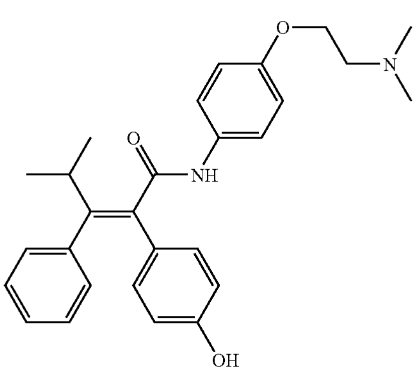 | B001A | A |

-continued

| Compound | Structure | Name | Category |
|---|---|---|---|
| 5 | 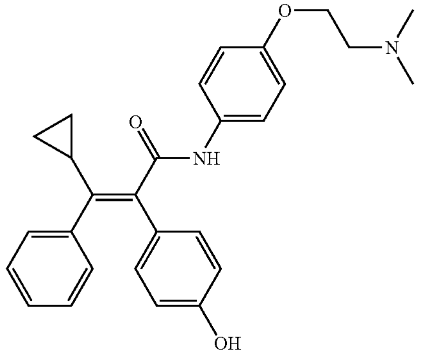 | B034A | A |
| 6 | 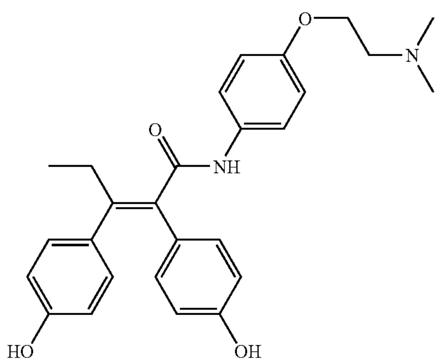 | A074A | B, E |
| 7 | 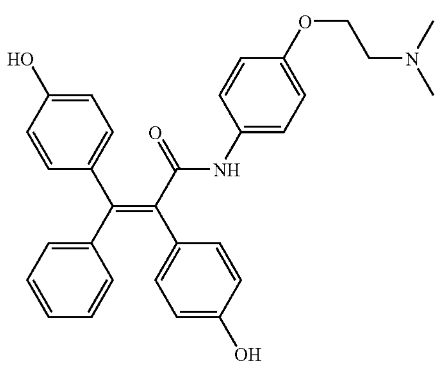 | A140A | A, E |
| 8 | 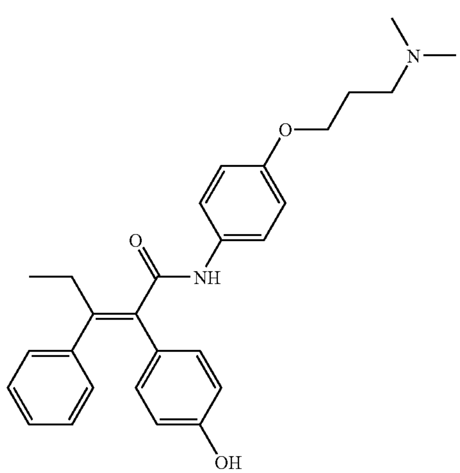 | A065A | C |

-continued
| Compound | Structure | Name | Category |
|---|---|---|---|
| 9 | 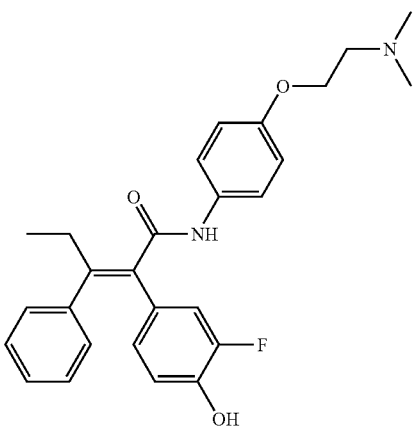 | B043A | D |
| 10 | 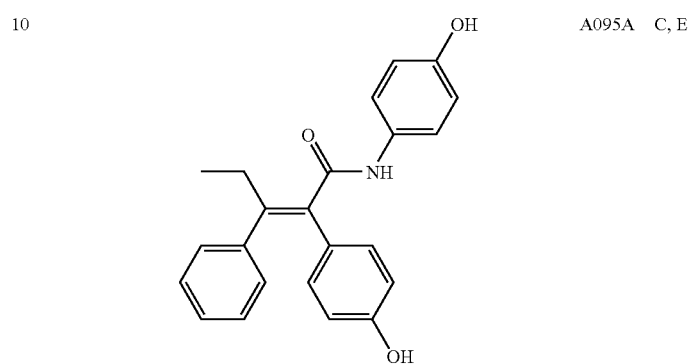 | A095A | C, E |
| 11 | 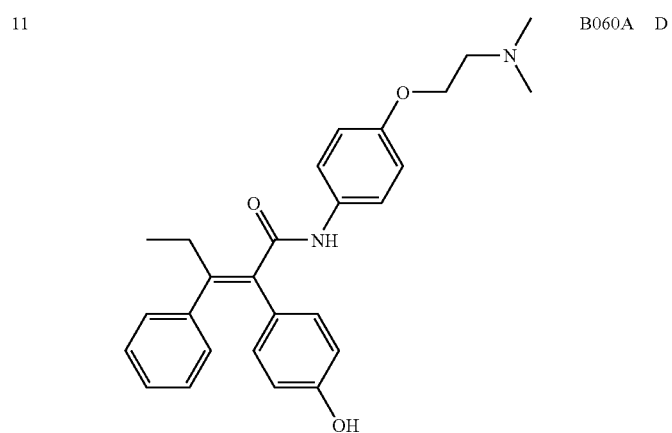 | B060A | D |

-continued
| Compound | Structure | Name | Category |
|---|---|---|---|
| 12 | 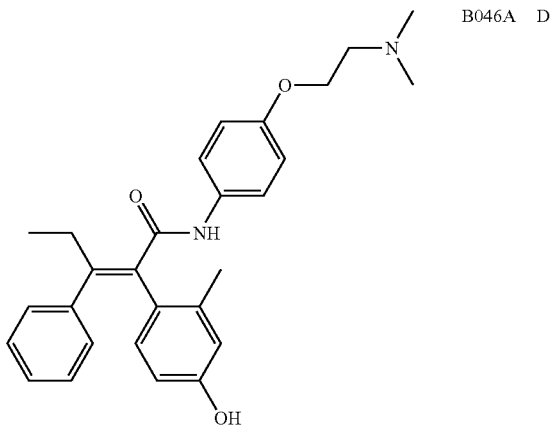 | B046A | D |
| 13 | 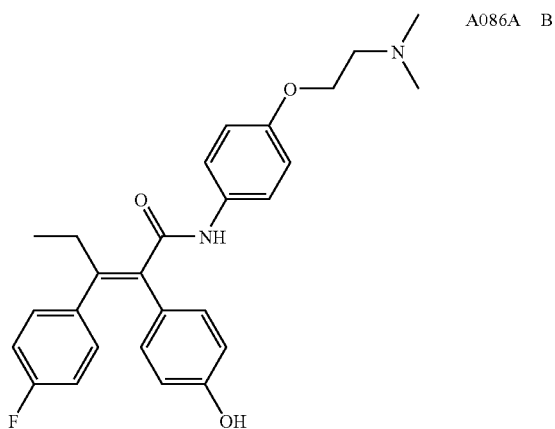 | A086A | B |
| 14 | 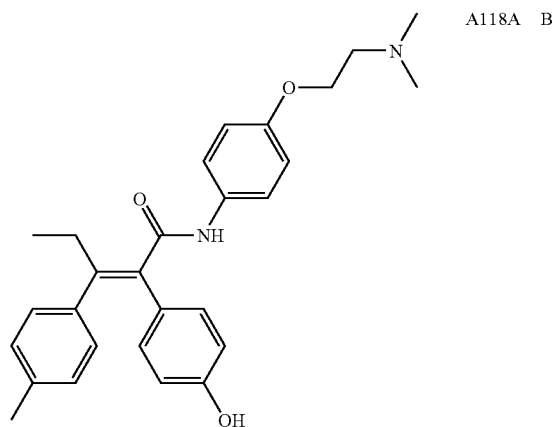 | A118A | B |

-continued
| Compound | Structure | Name | Category |
|---|---|---|---|
| 15 | 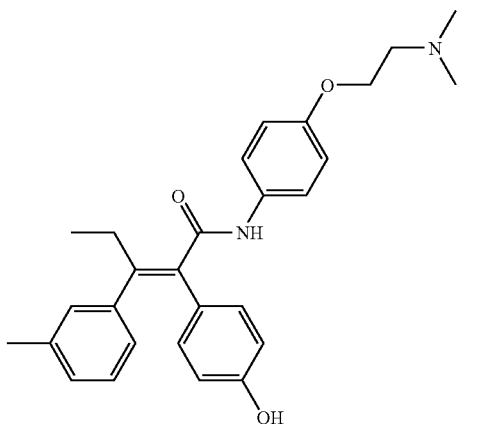 | A123A | B |
| 16 | 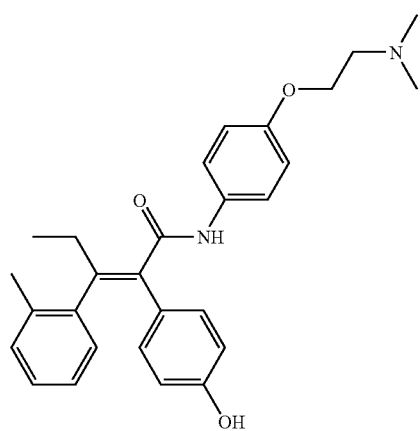 | A127A | B |
| 17 | 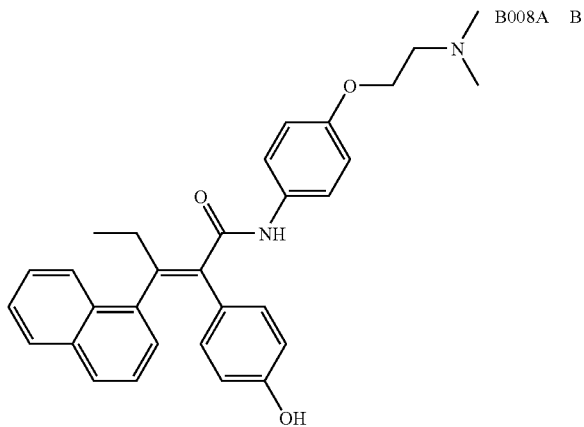 | B008A | B |

-continued

| Compound | Structure | Name | Category |
|---|---|---|---|
| 18 | 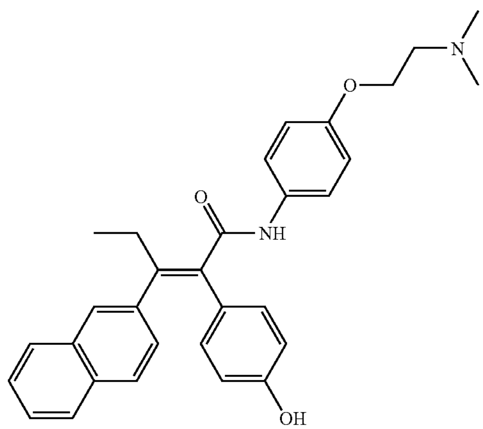 | B016A | B |
| 19 | 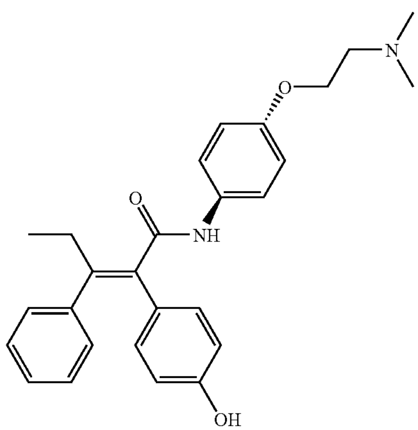 | B0 | C |
| 20 | 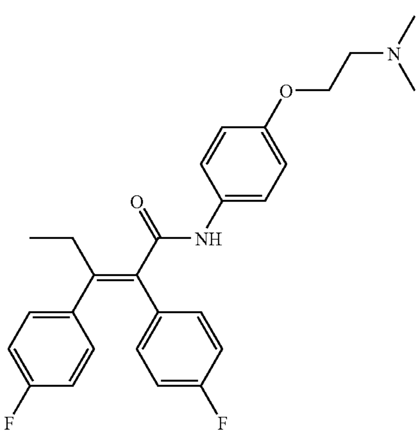 | A060A | F |
| 21 | 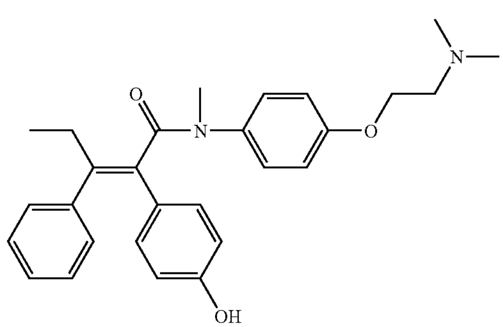 | A078A | F |

| Compound | Structure | Name | Category |
|---|---|---|---|
| 22 | 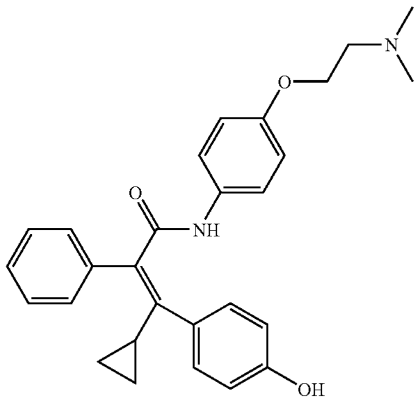 | B047A | F |
| 23 | 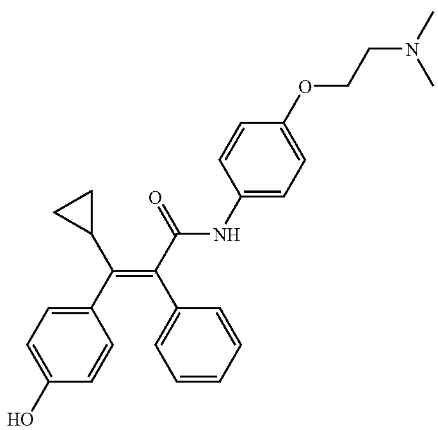 | A142A | F |
| 24 | 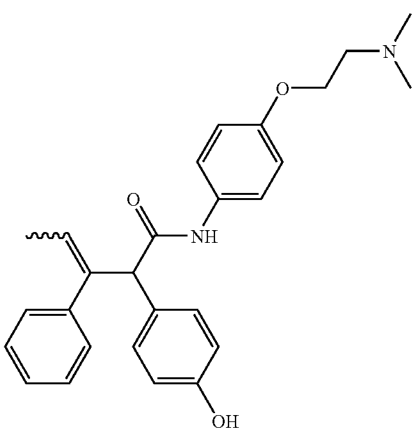 | A072A | F |

EXAMPLE 22

This example describes the identification and characterization of a previously unidentified membrane associated estrogen receptor and an assay for the identification and evaluation of SERMs.

General Methods for SERM Assays and Screening

Female Topeka guinea pigs (400-600 g), bred in the Oregon Health Sciences University institutional breeding facility and female multicolor guinea pigs (400-500 g, Elm Hill, Mass.) were used. The guinea pigs were maintained under constant temperature (26° C.) and light (on between 06:30-20:30 h). Animals were housed individually, with food and water provided ad libitum. They were ovariectomized under ketamine/xylazine anesthesia (33 mg/kg & 6 mg/kg, respectively; subcutaneous) 5-7 days prior to experimentation, and given sesame oil vehicle (0.1 mL subcutaneous) 24 h prior to experimentation. Serum estrogen concentrations were determined by radioimmunoassay (Wagner et al., *J Neurosci* 21: 2085-2093, 2001) from trunk blood collected on the day of experimentation and were less than 10 μg/mL. An additional group of animals (n=6) were ovariectomized and after one week injected with oil vehicle, estradiol benzoate (25 μg in oil) or compound 8 (example 4, 25 μg in oil) 24 h prior to sacrifice.

Wild-type C57BL/6 mice in these studies were obtained from Jackson laboratories. All animals were maintained under controlled temperature (25° C.) and photoperiod conditions (14-h light, 10-h dark; lights on between 0700 and 2100) with food and water ad libitum. Adult mice were ovariectomized under isoflurane anesthesia, and allowed to recover for 1 week. At this time the animals were injected daily for 2 days with oil vehicle, estradiol benzoate (EB; 1 µg) or compound 8 (2 or 5 µg), and anesthetized and killed by decapitation after 24 h. The uteri were collected, weighed and fixed in 4% paraformaldehyde for later histological analysis (data not shown).

Commercially Available Drugs:

Drugs were purchased from Calbiochem (LaJolla, Calif., USA) unless otherwise specified. Tetrodotoxin (TTX; Alomone, Jerusalem, Israel) was dissolved in Milli-Q $H_2O$ and further diluted with 0.1% acetic acid (final concentration 1 mM; pH 4-5). 17β-estradiol (17β-estradiol) was purchased from Steraloids (Wilton, N.H., USA), recrystallized to ensure purity and dissolved in 100% ethanol to a stock concentration of 1 mM. 17α-estradiol (1 mM, Steraloids), anti-estrogen: ICI 182, 780 (10 mM, Toeris Cookson, Ballwin, Mo.) and the selective estrogen receptor modulators 4-OH-tamoxifen (10 mM, Steraloids), raloxifene (10 mM, Eli Lilly, Indianapolis, Ind.) and compound 8 (10 mM) were also dissolved in 100% ethanol. 17β-estradiol 17-hemisuccinate: BSA (17β-estradiol-BSA, 1 mM, Steraloids) was dissolved in $H_2O$. The protein kinase A inhibitor, H-89 dihydrochloride (10 mM), the protein kinase A activator forskolin (50 mM), the protein kinase C inhibitors bisindolylmaleimide I hydrochloride (BIS, 100 µM), Gö6976 (2 mM) and rottlerin (10 mM), the phospholipase C inhibitor U73122 (20 mM), the less active analog U73343 (20 mM) and the MEK1 inhibitor PD98059 (50 mM) were dissolved in DMSO. Protein kinase A inhibitory peptide 6-22 Amide (1 mM), the protein kinase A inhibitor: Rp-cAMPS (50 mM) and Cholera toxin A subunit (1 µg/uL) were dissolved in $H_2O$. The Gq binding protein designed to mimic the C terminus of the Gq α subunit and Gs α binding protein designed to mimic the C terminus of the Gs a subunit were synthesized by PeptidoGenic Research (Livermore, Calif.). The peptide sequence for Gq peptide was Ac-LGLNLKEYNLV-OH (SEQ ID NO:1) and for Gs peptide was CRMHLRQYELL (SEQ ID NO:2). The peptides were also dissolved in $H_2O$. BAPTA tetrasodium salt (1,2-bis-(o-aminophenoxyethane)-N,N,N',N'-tetraacetic acid) was dissolved in the internal solution at a 10 mM concentration. Aliquots of the stock solutions were stored as appropriate until needed.

Statistical Analyses:

Statistical analyses for comparing between groups were performed using a one-way analysis of variance (with post hoc (Newman-Keuls) paired analysis). Differences were considered statistically significant if the probability of error was less than 5%.

Tissue Preparation:

On the day of experimentation the animal was decapitated, its brain removed from the skull and the hypothalamus dissected. The resultant hypothalamic block was mounted on a plastic cutting platform that was then secured in a vibratome well filled with ice-cold, oxygenated (95% $O_2$, 5% $CO_2$) artificial cerebrospinal fluid (aCSF, in mM: NaCl, 124; $NaHCO_3$ 26; dextrose, 10; HEPES, 10; KCl, 5; $NaH_2PO_4$, 2.6; $MgSO_4$, 2; $CaCl_2$, 1). Four coronal slices (350 µm) through the arcuate were cut. The slices were transferred to a multi-well auxiliary chamber containing oxygenated aCSF, and kept there until electrophysiological recording after approximately 2 h.

Electrophysiology:

Whole-cell patch recordings in voltage clamp were performed as previously described (Wagner et al., *J Neurosci* 21: 2085-2093, 2001). Briefly, slices were maintained in a chamber perfused with warmed (35° C.), oxygenated aCSF containing the same constituents and respective concentrations except for $CaCl_2$, which was raised to 2 mM. Artificial CSF (aCSF) and all drug solutions were perfused via a peristaltic pump at a rate of 1.5 mL/min. Drug solutions were prepared in 20 mL syringes by diluting the appropriate stock solution with aCSF, and the flow was controlled via a three-way stopcock.

For whole-cell recordings, electrodes were fabricated from borosilicate glass (World Precision Instruments, Inc., Sarasota, Fla., USA; 1.5 mm O.D.). Resultant electrodes were then filled with an internal solution containing 0.5% biocytin and consisting of the following in mM: $K^+$ gluconate, 128; NaCl, 10; $MgCl_2$, 1; EGTA, 11; HEPES, 10; ATP, 1.2; GTP, 0.4; the pH was adjusted to 7.3-7.4 with 1 N KOH; 272-315 mOsm. Voltage pulses were amplified and passed through the electrode using an Axopatch 1D preamplifier (Axon Instruments, Union City, Calif.). The resultant current deflections were monitored using a digital oscilloscope (Tektronix 2230, Beaverton, Oreg., USA). Upon the reduction of the current deflection, negative pressure was applied via a 5 mL syringe connected by polyethylene tubing to the electrode in order to form a seal (>1 GΩ). Following formation of a seal, intracellular access was achieved by suction, followed by perfusion with 1 µM TTX for at least 4-6 min to block spontaneous firing and synaptic potentials before applying the $GABA_B$ receptor agonist baclofen (FIG. 1). All the responses to baclofen were measured in voltage clamp as outward currents ($V_{hold}$=-60 mV), and only those cells that showed less than 10% change in access resistance (access resistances ranged from 20-30 MΩ) throughout the recording were included in this study. Membrane currents underwent analog-digital conversion via a Digidata 1200 interface coupled to pClamp 7.0 (Axon Instruments, Union City, Calif.). Low-pass filtering of the currents was conducted at a frequency of two KHz. The liquid junction potential was −10 mV, and was corrected for in subsequent data analysis.

Figure 2:
FIG. 2 is an image showing an example of a biocytin-filled neuron after whole-cell patch-clamp recording for 13 min illustrating the extent of the biocytin labeling.

Post-Hoc Identification of Hypothalamic Arcuate Neurons:

Following electrophysiological recording, the slices were fixed with 4% paraformaldehyde in Sorensen's phosphate buffer (pH 7.4) for 120 min, immersed overnight in 20% sucrose dissolved in Sorensen's buffer and then frozen in O.C.T. embedding medium and prepared for immunocytochemistry as previously described (Kelly et al., *Methods in Neurosciences: Pulsatility in Neuroendocrine Systems*, pp 47-67. San Diego: Academic Press, Inc, 1994.). Briefly, coronal sections (20 µm) were cut on a cryostat (Leitz Model 1720 Digital Cryostat) and mounted on Fisher SuperFrost Plus slides. Sections were washed for 5 min with 0.1 M sodium phosphate buffer (pH 7.4), and then streptavidin-Cy2 (Jackson ImmunoResearch Laboratories, PA) (1:1000) was applied for 2 h. The reaction was terminated by washing with buffer. The slices were scanned for the injected neuron with a Nikon Eclipse 800 fluorescence microscope (Nikon Instruments, Melville, N.Y.). After localization of the biocytin-filled neurons, the slides containing the appropriate sections were processed for the presence of tyrosine hydroxylase (TH) or β-endorphin using fluorescence immunohistochemistry as described previously (Kelly et al., *Methods in Neurosciences: Pulsatility in Neuroendocrine Systems*, pp 47-67. San Diego: Academic Press, Inc, 1994.). Briefly, the sections with the biocytin-identified neurons were incubated overnight with a monoclonal TH antibody at 1:10,000 (Diasorin, Stillwater, Minn.), or with a polyclonal β-endorphin antibody at 1:5,000 (Dave et al., *Endocrinology* 117: 1389-1396, 1985.), washed in 0.1 M phosphate buffer followed by incubation with a goat anti-mouse IgG-Cy3 at 1:500 or donkey anti-rabbit IgG-Cy3 at 1:500, respectively (Jackson ImmunoResearch Laboratories, PA). The sections were washed with sodium phosphate buffer, and coverslips were applied using a glycerolglycine buffer containing 5% N-propylgallate. Immunostained cells were photographed using a Nikon microscope. See FIG. 2.

Estrogen Receptor Binding Assays:

The relative binding affinity of compounds for the estrogen receptors (ER)α and (ER)β was determined using a spin column assay with commercially available full-length forms of both (ER)α and (ER)β (PanVera Corp, Madison, Wis., USA). Receptor was added to a final concentration of 15 nM to a solution containing 10 mM Tris, pH 7.5, 10% glycerol, 2 mM DTT and 1 mg/mL BSA and 3 nM [2,4,6,7,16,17-$^3$H] estradiol at 4° C. 100 μL of the solution was added to 1 μL of the ligand in ethanol, mixed gently by pipetting and incubated at 4° C. overnight. The mixture was then applied to a micro spin column containing G-25 Sephadex (Harvard Apparatus Inc.) equilibrated in binding buffer (minus tritiated estradiol) according to the manufacturer's instructions. Bound estradiol was separated from free ligand by spinning at 2000×g for 4 min at room temperature. The filtrate was then added to 2.5 mL of scintillant and counted in a liquid scintillation counter. A binding curve was fitted using a single binding site competition model with the Prism (GraphPad Software, San Diego, Calif.) statistical analysis software package. The standard deviation was determined to be less than 0.2 log units from the $EC_{50}$ value. Percent relative binding affinity was then determined by dividing the $IC_{50}$ determined for unlabeled estradiol by the ligand $IC_{50}$ and multiplying by 100.

Dispersed Single-Cell RT-PCR:

Guinea pig 350 μm coronal hypothalamic slices were cut on a vibratome from caudal to rostral and placed in an auxiliary chamber containing oxygenated aCSF. The slices were allowed to recover for 1-2 h in the chamber before dispersion. The arcuate nucleus of the hypothalamus was microdissected and incubated in 2-3 mL of Hank's balanced salt solution (HBSS in mM; $CaCl_2$, 1.26; $MgSO_4$, 1; KCl, 5.37; $KH_2PO_4$, 0.44; NaCl, 136.89; $Na_2HPO_4$, 0.34; D-glucose, 5.55; Hepes, 15 in DEPC-treated water(pH 7.3, 300 mOsm) containing 1 mg/mL protease XIV (Sigma, St. Louis, Mo.) for approximately 15 min at 37° C. The tissue was then washed four times in one volume low calcium aCSF and two times in HBSS. The cells were isolated by trituration with flame-polished Pasteur pipettes, dispersed on a dish and continuously perfused with HBSS at a rate of 1.5 mL/n. Cells were visualized using a Nikon inverted microscope and individual neurons were patched and harvested into the patch pipette by applying negative pressure. The content of the pipette was expelled into a siliconized microcentrifuge tube containing 5 μL of the following solution: 0.5 μL of 10× buffer (100 mM Tris-HCL, 500 mM KCl, 1% Triton-X 100; Promega, Madison, Wis.), 15 U RNasin (Promega), 0.5 μL 100 mM DTT and DEPC-treated water.

In addition, hypothalamic tissue was homogenized and total RNA extracted using the RNeasy kit (Qiagen, Valencia, Calif.) according to the manufacturer's protocol. The harvested cell solution and 25 ng of hypothalamic total RNA in 1 μL were denatured for 5 min at 65° C., cooled on ice for 5 min, and then single stranded cDNA was synthesized from cellular RNA by adding 50 U MuLV reverse transcriptase (Applied Biosystems, Foster City, Calif.), 1.5 μL 10× buffer, 2 mM $MgCl_2$, 0.2 μL deoxynucleotide triphosphates (dNTPs), 15 U RNasin, 10 mM DTT, 100 ng random hexamers and DEPC-treated water to a final volume of 20 μL. Cells and tissue RNA used as negative controls, were processed as described above but without reverse transcriptase. The reaction mixtures were incubated at 42° C. for 60 min, denatured at 99° C. for 5 min and cooled on ice for 5 min.

PCR was performed using 3 μL of cDNA template from each RT reaction in a 30 μL PCR reaction volume containing: 3 μL 10× buffer, 2.4 μL $MgCl_2$ (2 mM final concentration for TH, POMC, $GABA_B$-R2, PKCδ, adenylyl cyclase VII and GAPDH) or 3.6 μL $MgCl_2$ (3 mM final concentration for GAD), 0.2 mM dNTPs, 0.2 μM forward and reverse primers, 2 Units Taq DNA polymerase (Promega) and 0.22 μg TaqStart Antibody (Clontech, Palo Alto, Calif.). Taq DNA polymerase and TaqStart Antibody were combined and incubated at room temperature for 5 min, the remainder of the reaction contents were added to the tube and incubated at 94° C. for 2 min. Then, each reaction went through 60 cycles (35 cycles for GAPDH) of amplification according to the following protocols: 94° C., 45 sec; 55° C. (GAD), 57° C. (PKCδ), 58° C. ($GABA_B$-R2), 60° C. (TH and adenylyl cyclase VII), 61° C. (POMC), 63° C. (GAPDH) 45 sec; 72° C., 1 min 10 sec; with a final 72° C. extension for 5 min. Ten microliters of the PCR products were visualized with ethidium bromide on a 1.5% agarose gel.

All of the primers were synthesized by Invitrogen (Carlsbad, Calif.) and were as follows: Guinea pig GAD65; 207 bp product, forward primer 5'-GGCTCTGGTGATGGAATA-3' (SEQ ID NO:3), reverse primer 5'-CAGAATCACGCT-GTCTGTT-3' (SEQ ID NO:4), Guinea pig TH; 223 bp product, forward primer 5'-TCCACGTTATACTGGTTCAC-3' (SEQ ID NO:5), reverse primer 5'-TTGCATCACT-GAAGCTCTC-3' (SEQ ID NO:6); Guinea pig $GABA_B$-R2; 241 bp product, forward primer 5'-TGTTTGTGC-CAAAGCTCATC-3' (SEQ ID NO:7) reverse primer 5'-GT-GTCTTGCAGTTGCATAGT-3' (SEQ ID NO:8), Guinea pig POMC (accession number S78260); 344 bp product, forward primer (bases 40-60) 5'-CTGGCCTTGCTGCTTCAGAT-3' (SEQ ID NO:9) reverse primer (bases 383-363) 5'-ATGGAG-TAGGAGCGCTTGTC-3' (SEQ ID NO:10); Guinea pig GAPDH; 212 bp product (accession number CPU51572), forward primer 5'CATCCACTGGTGCTGCCAAG-3' (SEQ ID NO:11), reverse primer 5'-GTCCTCGGTGTAGC-CCAAGA-3' (SEQ ID NO:12). Human protein kinase Cδ; 251 bp product (accession number L07861) forward primer (bases 1127-1147) 5'-AAAGGCAGCTTCGGGAAGGT-3' (SEQ ID NO:13), reverse primer (bases 1377-1357) 5'-TG-GATGTGGTACATCAGGTC-3' (SEQ ID NO:14). Guinea pig adenylyl cyclase VII; 235 bp product, forward primer 5'-CTGTTCGGCAAGTTTGACCAG-3' (SEQ ID NO:15), reverse primer 5'-TGACGCCACACAGCACATT-3' (SEQ ID NO:16).

17β-Estradiol and SERMs Rapidly Attenuate the $GABA_B$ Response in Hypothalamic Dopamine and Pro-Opiomelanocortin (POMC) Neurons:

The following data demonstrate that 17β-estradiol and SERMs rapidly attenuate a baclofen-induced $GABA_B$ response in hypothalamic neurons, which indicates that these compounds affect neurotransmission through non-transcriptional events. Whole cell recordings were made in arcuate neurons (n=195) from ovariectomized female guinea pigs. FIG. 1 is a schematic illustrating the protocol for drug administration in the whole-cell patch, voltage clamp studies ($V_{hold}$=−60 mV). After seals were formed and the whole-cell configuration was obtained, slices were perfused with TTX (1 μM) for 5 min. The first $GABA_B$ receptor-mediated response was generated by perfusing the $GABA_B$ agonist baclofen (at $EC_{50}$ concentration of 5 μM) until a steady-state outward current was obtained (first response, R1). After baclofen wash out, the current returned to its predrug resting level. The cells were then treated with 17β-estradiol and/or other drugs for 15 min, and baclofen (5 μM) was perfused again, and a second response ($R^2$) was measured. The effects of 17β-estradiol and/or other drugs on the baclofen response are expressed as a percentage of $R^2$ over R1. A subgroup of these neurons (n=55) was identified using dual labeling immunocytochemistry (data and images not shown). This revealed that 41% of the cells were TH-positive (i.e. dopamine neurons) and 39% were β-endorphin-positive (i.e. POMC neurons). Moreover, based on dual immunocytochemical staining and in situ hybridization for $GAD_{65}$ a subgroup of arcuate dopamine neurons co-express GABA (Rønnekleiv, unpublished findings), which was substantiated by the scRT-PCR data (see below). For the electrophysiology analysis, only cells with gigaohm or better seals were included in this study. The mean resting membrane potential was −54.3±0.4 mV at a 0 pA holding current, and the mean input resistance was 1.9±0.3 GΩ. Moreover, fifty percent of A12 dopamine neurons exhibited a T-type $Ca^{2+}$ current and a hyperpolarization-activated, cation current ($I_h$) (Loose et al., J Neurosci 10: 3627-3634, 1990.). Seventy-one percent of the POMC neurons exhibited $I_h$ and a transient outward $K^+$ current ($I_A$) (Kelly et al., Neuroendo 52: 268-275, 1990.). Therefore, the passive membrane properties measured with whole-cell patch recording is similar to results obtained using single electrode voltage clamp recordings (Loose et al., J Neurosci 10: 3627-3634, 1990; Kelly et al., Neuroendo 52: 268-275, 1990.).

Figure 3B:
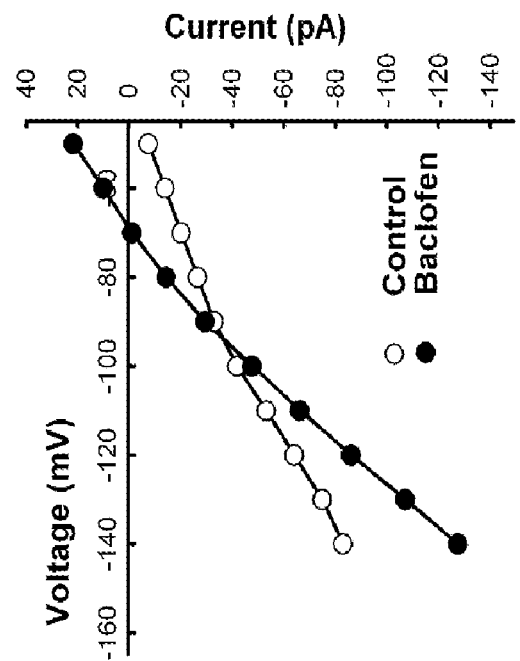
FIG. 3B is a graph of the pre- and post-baclofen I/V relationships following 17β-estradiol treatment in another cell illustrating the same reversal potential for the baclofen response.
Figure 3A:
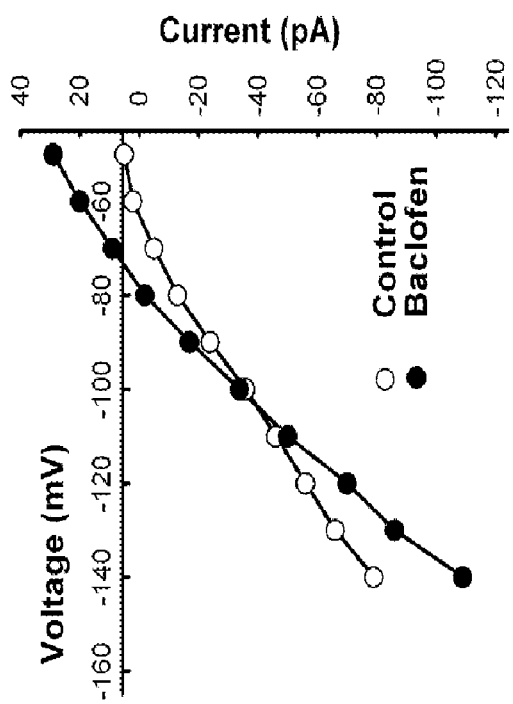
FIG. 3A is a graph illustrating the pre- and post-baclofen (5 μM) I/V relationships from a dopamine neuron.
Figure 4B:
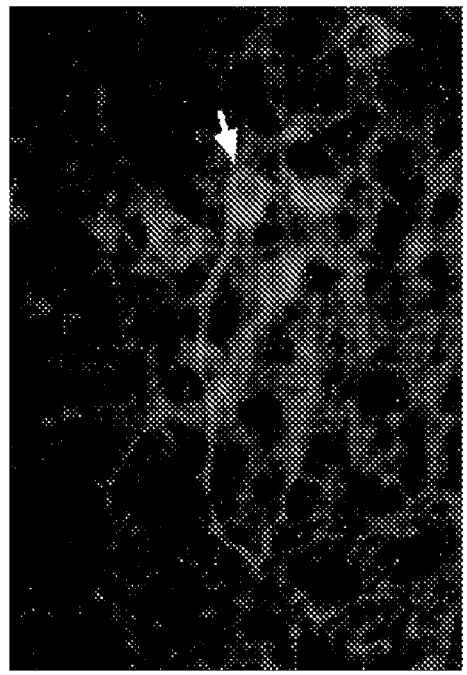
FIG. 4B is an image showing the immunocytochemical staining of tyrosine hydroxylase (TH) in the neuron imaged in FIG. 4A.
Figure 4A:
FIG. 4A is an image showing the biocytin-streptavidin-Cy2 labeling of fusiform arcuate dopamine neuron that responded to estrogen.
Figure 4D:
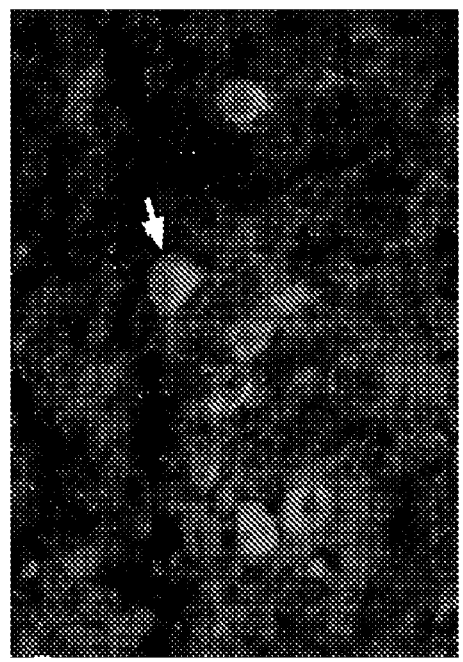
FIG. 4D is an image showing the immunocytochemical staining of β-endorphin in the neuron imaged in FIG. 4C.
Figure 4C:
FIG. 4C is an image showing the biocytin-streptavidin-Cy2 labeling of a small pyramidal arcuate POMC neuron.
Figure 5:
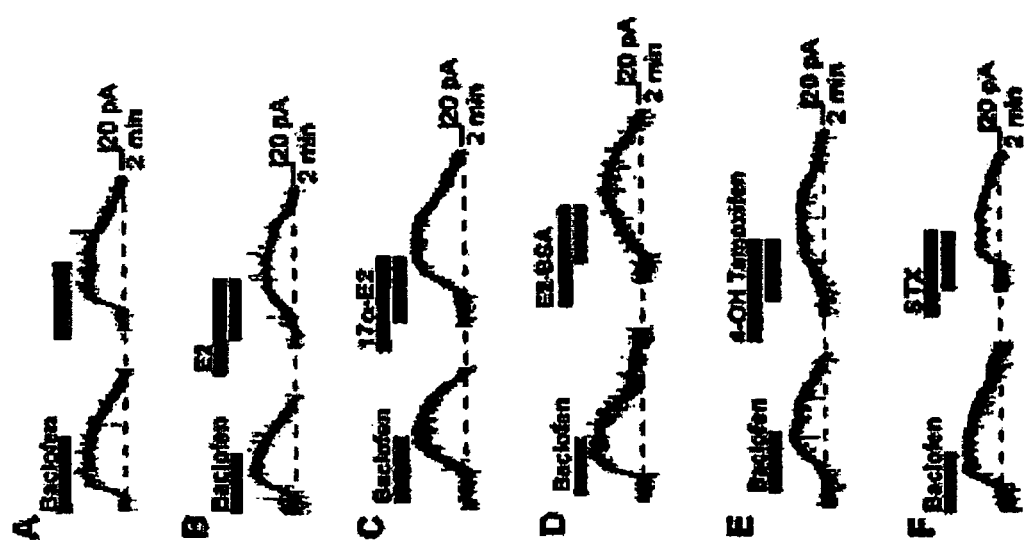
FIG. 5 includes representative traces of the $GABA_B$ responses before and after steroid treatment.
Figure 6:
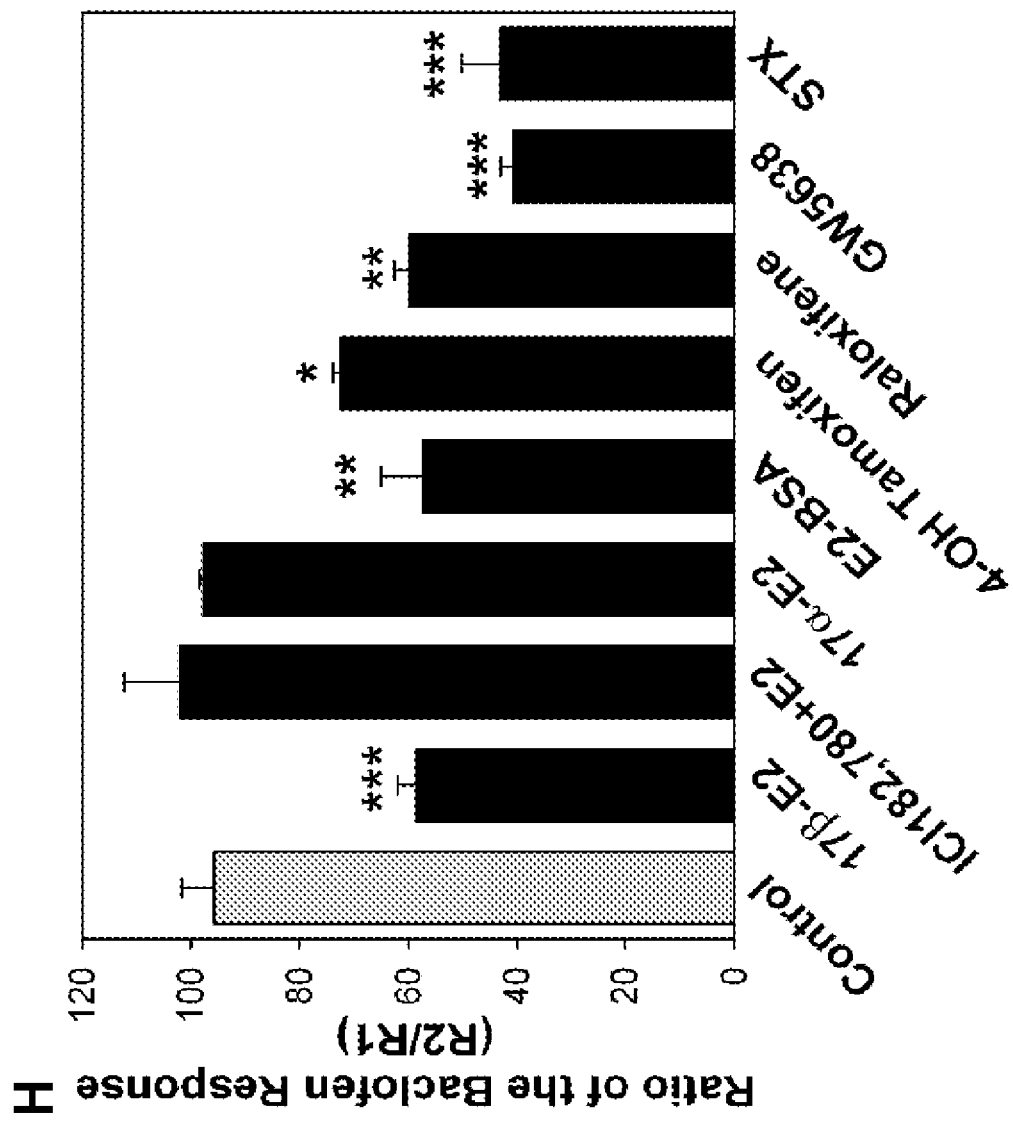
FIG. 6 includes bar graphs summarizing the effects of 17β-estradiol and SERMs on the baclofen response.

The whole-cell recording method was used to measure the rapid effects of 17β-estradiol on the activation of the G protein-coupled, inwardly-rectifying $K^+$ channel (GIRK) conductance by the $GABA_B$ receptor agonist baclofen. 17β-estradiol rapidly attenuates both p-opioid and $GABA_B$ receptor-mediated responses in hypothalamic arcuate neurons (Lagrange et al., 1994; Lagrange et al., 1996; Lagrange et al., 1997). Therefore, for measuring 17β-estradiol modulation of the $GABA_B$ response an $EC_{50}$ concentration (5 μM) of baclofen was used according to the protocol depicted in FIG. 1. A robust outward current was measured in response to baclofen that subsided after washout (FIG. 5 graph A and FIG. 6). The application of baclofen 20 min later elicited the same robust response, suggesting that desensitization and run-down were not occurring in response to successive applications of 5 μM baclofen. However, if 17β-estradiol (100 nM) was applied during the interim period (i.e. after the washout of the first application of baclofen), there was a significant (p<0.005) decrease of 41% in the response to a second application of baclofen (FIG. 5 graph B and FIG. 6). Current/voltage relationships generated before and during the application of 100 nM 17β-estradiol showed that this steroid did not change the reversal potential for the baclofen-mediated response: control $E_{baclofen}$=−88.8±3.6 mV, n=13; versus after 17β-estradiol $E_{baclofen}$=−85.4±3.9 mV, n=12 (FIGS. 3A and 3B). The effects of 17β-estradiol were stereospecific such that the biologically inactive stereoisomer 17β-estradiol (100 nM) had no effect on the baclofen response (FIG. 5 graph C and FIG. 6). Furthermore, the effects of 17β-estradiol were blocked by the anti-estrogen ICI 182,780, when co-perfused with 17β-estradiol (FIG. 6). Treatment with ICI 182,780 alone had no effect on the baclofen response (data not shown).

This previously unidentified estrogen receptor was determined to be membrane associated by using the membrane impermeable estrogen conjugate 17β-estradiol-BSA. 17β-estradiol-BSA (100 nM) was fully efficacious in inhibiting the baclofen response indicating that this estrogen receptor-mediated response is initiated at the plasma membrane (FIG. 5 graph D and FIG. 6). The integrity of the 17β-estradiol-BSA preparation was verified by performing a 17β-estradiol radioimmunoassay of the slice perfusate. No unbound 17β-estradiol was found in the media (data not shown) indicating that 17β-estradiol-BSA conjugate did not contain contaminating free 17β-estradiol.

The previously unidentified, membrane associated estrogen receptor was characterized by using several SERMs. Tamoxifen (1 μM) was inactive (p>0.05 versus control) and did not attenuate the effects of 17β-estradiol on the baclofen activation of GIRK (R2/R1 for 17β-estradiol: 58.6±3.4%, n=10; versus tamoxifen+17β-estradiol: 60.4+6.6%, n=5). However, 4-OH tamoxifen (1 μM) did partially mimic the actions of 17β-estradiol by blocking the baclofen response by 25% (FIG. 6). With reference to FIG. 6, 17β-estradiol (100 nM) attenuated the $GABA_B$ receptor-mediated outward current by 41%. The inhibitory effects of 17β-estradiol on the baclofen response were blocked by the estrogen receptor antagonist ICI 182,780 (1 μM). Bovine Serum Albumin-conjugated Estrogen (17β-estradiol-BSA, 100 nM), 4-OH tamoxifen (1 μM), raloxifene (1 μM), GW5638 (1 μM) and compound 8 (10 nM) also inhibited the baclofen response, but 17α-estradiol (1 μM) had no effect. Bars represent the mean±S.E.M. of 4-11 cells tested per group (*p<0.005, p<0.01, *p<0.05, versus vehicle-control group). Because 4-OH tamoxifen always exists as an E/Z mixture of olefin isomers (Katzenellenbogen et al., J Steroid Biochem 22: 589-596, 1985.), it is possible that only one of the isomers is active at mediating this novel estrogen response. Raloxifene (1 μM), another SERM with a hydroxylated aromatic ring, completely mimicked the actions of 17β-estradiol in terms of efficacy in the suppression of the baclofen response (FIG. 6). In contrast, the non-hydroxylated SERM GW-5638, which structurally resembles the triphenylethylene core of tamoxifen, was found to be significantly more efficacious than 17β-estradiol at inhibiting GIRK channel activation by baclofen (FIG. 6).

Compound 8 is a SERM Devoid of Nuclear ER Activity that Selectively Attenuates Rapid Responses:

All of the above mentioned compounds are high affinity ligands for the nuclear estrogen receptors, which complicates the interpretation of the observed pharmacology and makes it difficult to exclude unequivocally a role for nuclear estrogen receptors. However, compound 8 (example 4) has approximately one million-fold reduced binding affinity for the nuclear estrogen receptor (ER)α or ERβ compared to that of 17β-estradiol (Table 1). Moreover, unlike 4-OH tamoxifen, compound 8 is geometrically stable and does not exist as a mixture of E/Z olefin isomers. In addition, compound 8 has no uterotropic actions even at five times the dose of 17β-estradiol (FIGS. 6A and 6B), confirming in vivo that 8 has no 4-OH tamoxifen-like estrogenic activity mediated by the nuclear estrogen receptors. However, in the whole cell electrophysiological assay, 10 nM 8 was as efficacious as 100 nM 17β-estradiol in attenuating the $GABA_B$ response (FIG. 6).

TABLE 1

Relative binding affinities (RBA) of ligands to full length (ER)α or (ER)β*

| Ligand | Relative binding affinity (ER)α | Relative binding affinity (ER)β |
| --- | --- | --- |
| 17β-estradiol | 100 | 100 |
| 4-hydroxytamoxifen | 36 | 43 |
| GW-5638 | 5 | 8 |

TABLE 1-continued

Relative binding affinities (RBA) of ligands to full length (ER)α or (ER)β*

| Ligand | Relative binding affinity (ER)α | Relative binding affinity (ER)β |
|---|---|---|
| Compound 8 (example 4) | $4.3 \times 10^{-6}$ | $9.0 \times 10^{-6}$ |

*Relative binding affinities are expressed as a percentage of the potency of 17β-estradiol. Under the conditions described in Example 22, 17β-estradiol was found to have an $IC_{50}$ of 5 nM for (ER)α and 3 nM for (ER)β.

Figure 8:
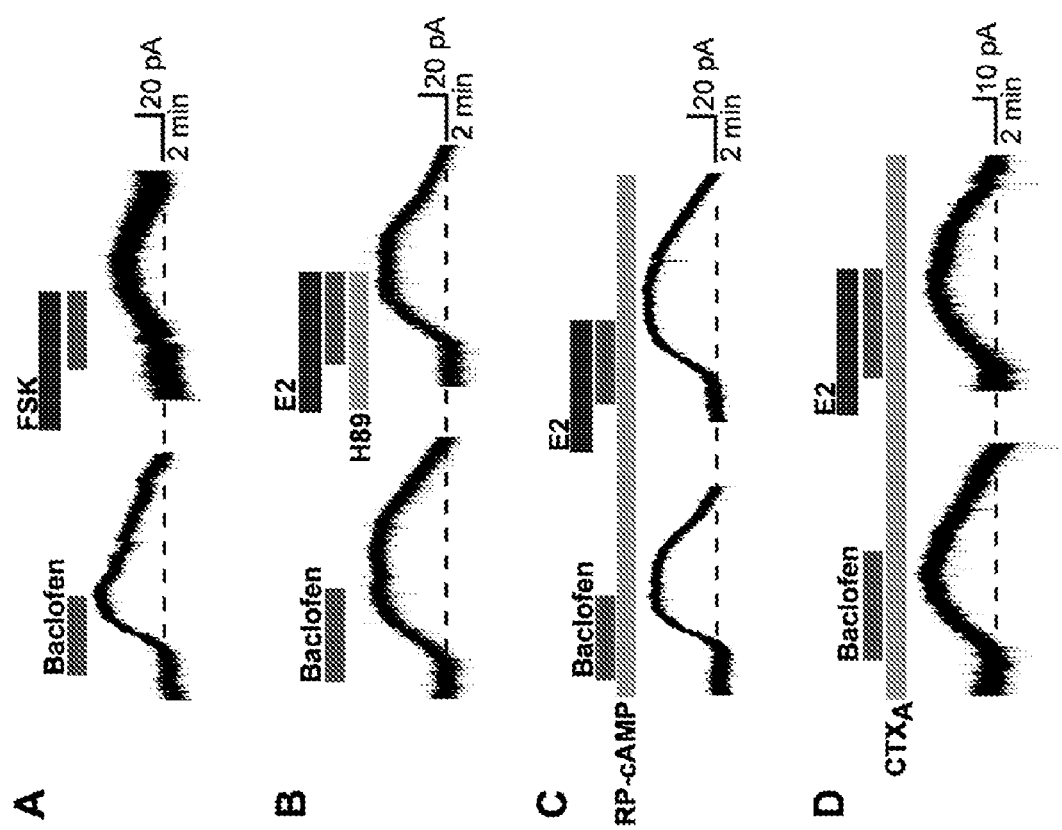
FIG. 8 includes representative traces of the baclofen responses in the presence of PKA activators or inhibitors and demonstrates that 17β-estradiol attenuation of the $GABA_B$ response involves protein kinase A.
Figure 9:
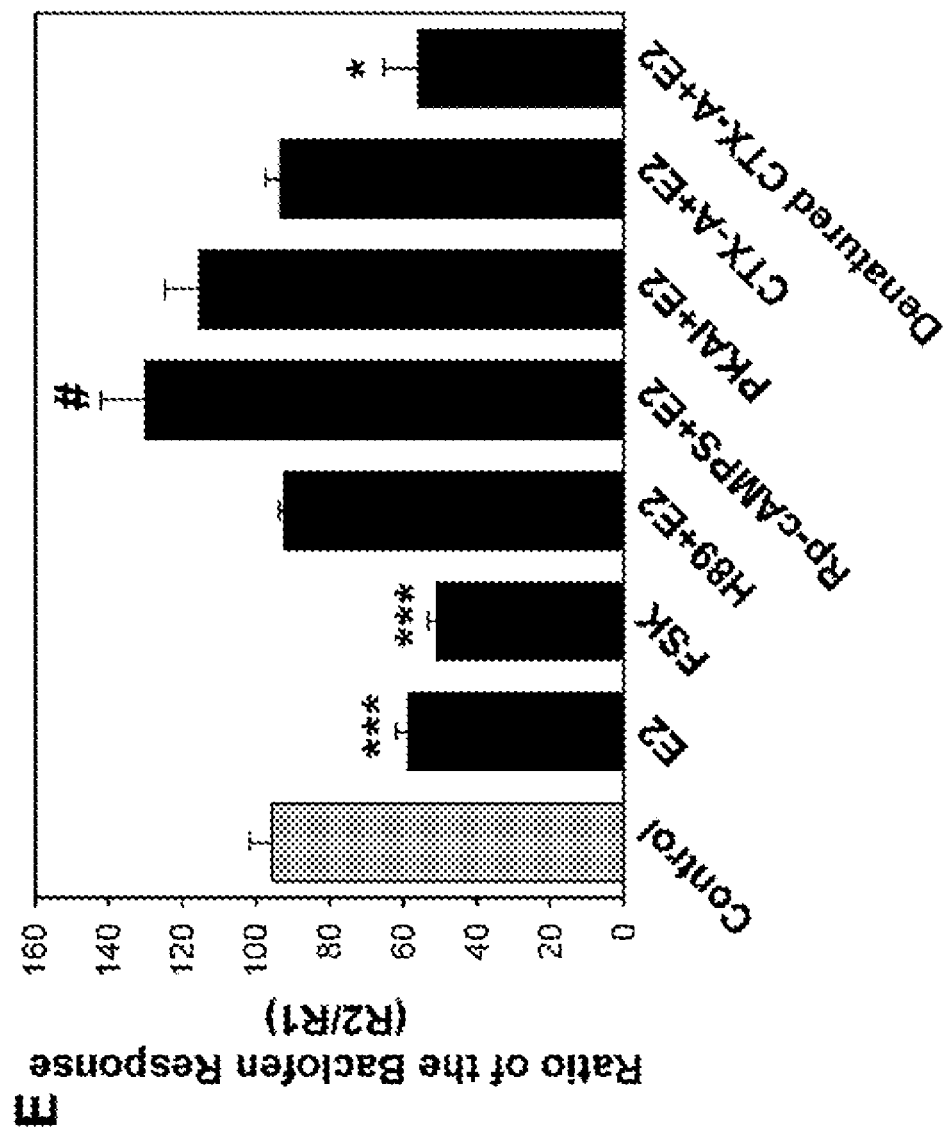
FIG. 9 is a bar graph summarizing the effects of protein kinase A (PKA) drugs on the baclofen response.

The Rapid Effect of 17β-estradiol on the $GABA_B$ Response Involves Protein Kinase A (PKA):

The involvement of specific signaling proteins in the 17β-estradiol mediated modulation of $GABA_B$ was determined by blocking different pathways. For example, if activation of the PKA pathway is involved, then the effect of 17β-estradiol on $GABA_B$ responses should be blocked by inhibiting PKA and mimicked by stimulating PKA. Thus, selective PKA inhibitors and activators were used to demonstrate that the PKA is involved. For example, as shown in FIG. 8 graph A and FIG. 9, forskolin (10 μM) could mimic the actions of 17β-estradiol to attenuate the $GABA_B$ response. On the other hand, the specific PKA inhibitor H89 (10 μM) blocked the 17β-estradiol induced suppression of the $GABA_B$ response (FIG. 8 graph B and FIG. 9).

The involvement of PKA in 17β-estradiol modulation of $GABA_B$ responses was further confirmed by the effect of the specific PKA inhibitory peptide PKI (protein kinase A Inhibitor 6-22 Amide, 20 μM) or the non-hydrolyzable cAMP analog Rp-cAMP (200 μM) that blocks PKA activation on neurons. After ~15 min of dialysis with PKI or Rp-cAMP, the 17β-estradiol-induced reduction of the $GABA_B$ response was abolished (FIG. 8 graph C and FIG. 9). Cholera toxin (CTX), which is a bacterial exotoxin secreted by *vibrio cholerae*, elevates intracellular cAMP levels in a variety of tissues by ADP-ribosylating the G-protein Gs thereby stimulating adenylyl cyclase activity in an apparently irreversible manner. Intracellular dialysis with the active unit of CTX into individual cells occluded the rapid inhibition of $GABA_B$ response by estrogen (FIG. 8 graph D and FIG. 9). These results indicate that the suppression of the $GABA_B$ response by 17β-estradiol requires the activation of PKA. FIG. 9 summarizes the effects of the PKA drugs tested. The PKA activator forskolin could mimic the effects of 17β-estradiol, the specific PKA inhibitors, H89 (10 μM), Rp-cAMPS and PKAI could block the effects. CTX-A could occlude the attenuation of the baclofen response by 17β-estradiol, but the denatured CTX-A could not. Bars represent the mean±S.E.M. of 4-11 cells tested per group (*** $p<0.005$, * and #$p<0.05$, versus vehicle-control; CTX-A+17β-estradiol versus denatured CTX-A+17β-estradiol, $p<0.05$).

Attenuation of the $GABA_B$ Response Involves Protein Kinase C□(PKCδ)□

Figure 10:
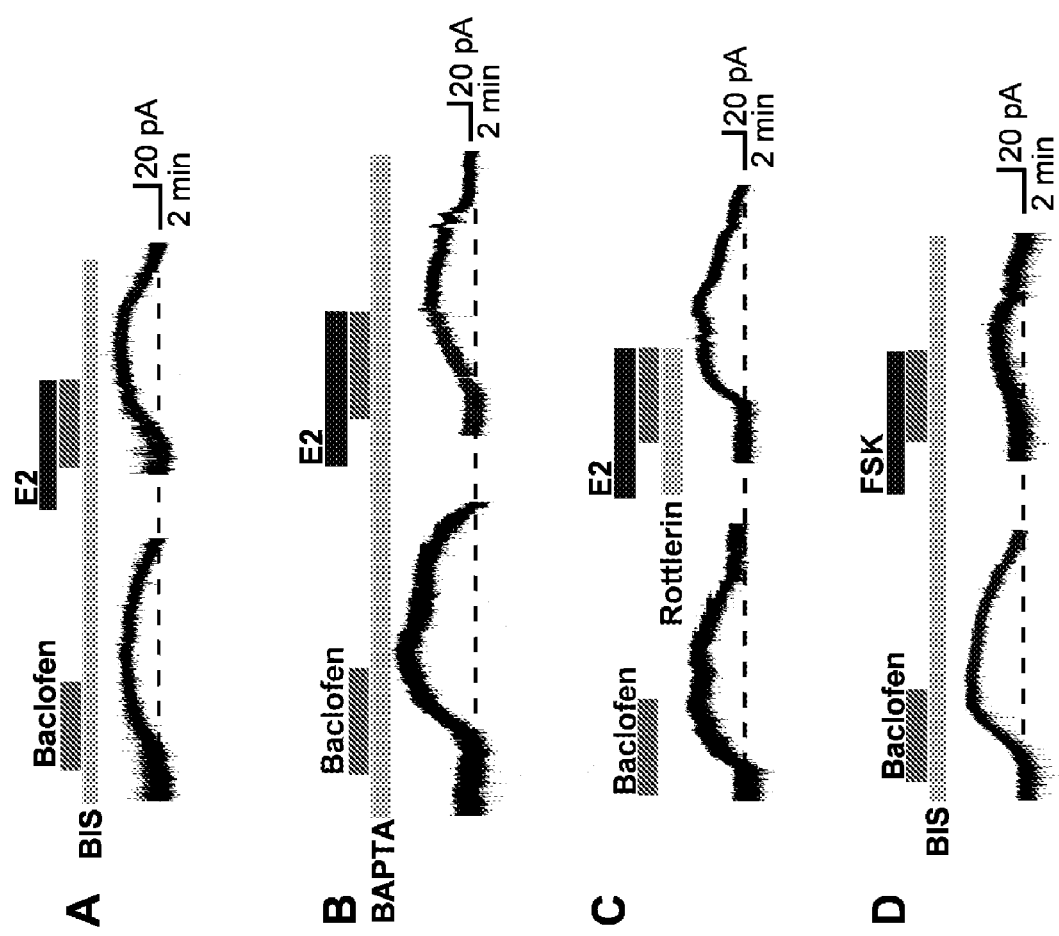
FIG. 10 includes representative traces of the baclofen responses in the presence of PKC inhibitors.
Figure 11:
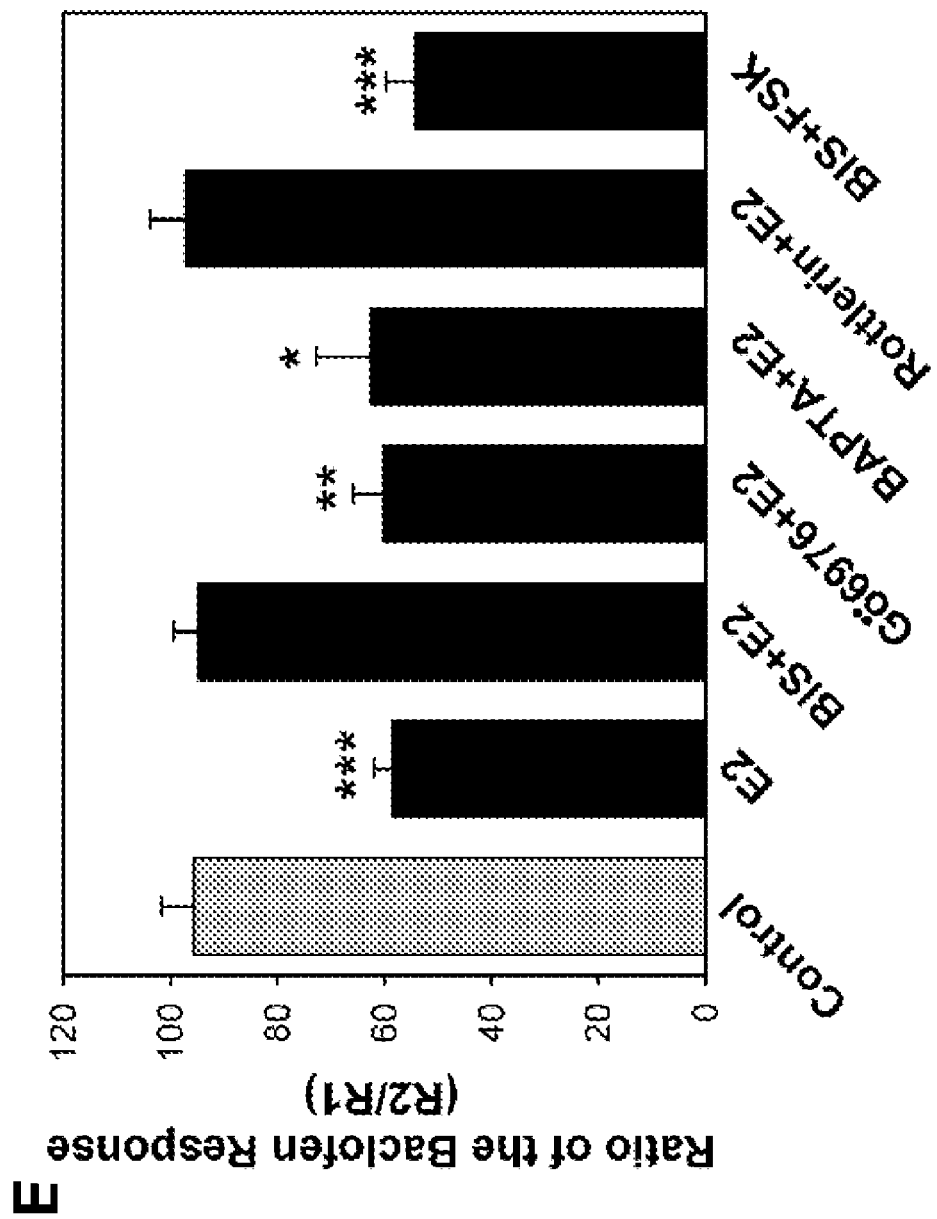
FIG. 11 is a bar graph summarizing the effects of protein kinase C (PKC) inhibitors on the baclofen response.

PKC also is involved in 17β-estradiol modulation of the $GABA_B$ response, as demonstrated by the effects of several selective PKC inhibitors. The first inhibitor, bisindolymaleimide (BIS), is a selective inhibitor of PKC that does not distinguish between the conventional, novel and atypical isoforms of PKC. The second, Gö6976, is a selective inhibitor of the conventional PKC isoforms (Martiny-Baron et al., *J Biol Chem* 268: 9194-9197, 1993; Way et al., *Trends Pharmacol Sci* 21: 181-187, 2000). Treatment of neurons with BIS nearly eliminated the effects of 17β-estradiol (FIG. 10 graph A and FIG. 11). In contrast, Gö6976 treatment was without effect (FIG. 11). Indeed, after replacing intracellular EGTA with 10 mM 1,2-bis-(o-aminophenoxyethane)-N,N,N',N'-tetraacetic acid (BAPTA), a calcium buffer with similar $Ca^{2+}$ affinity as EGTA but a much faster on rate, the estrogen inhibition of the $GABA_B$ response was still observed (FIG. 10 graph B and FIG. 11). Because conventional isoforms of PKC are unlikely to be active with this level of calcium buffering, these results further support a role for a $Ca^{2+}$-independent, novel PKC isoform in mediating the effects of estrogen. Finally, the selective PKCδ inhibitor rottlerin (5 μM) completely blocked 17β-estradiol's ability to inhibit the $GABA_B$ response in hypothalamic neurons (FIG. 10, graph C and FIG. 11). FIG. 11 summarizes the effects of the PKC inhibitors tested. Bars represent the mean±S.E.M. of 4-11 cells tested per group (* $p<0.005$,  $p<0.01$, * $p<0.05$ versus vehicle-control).

Figure 12:
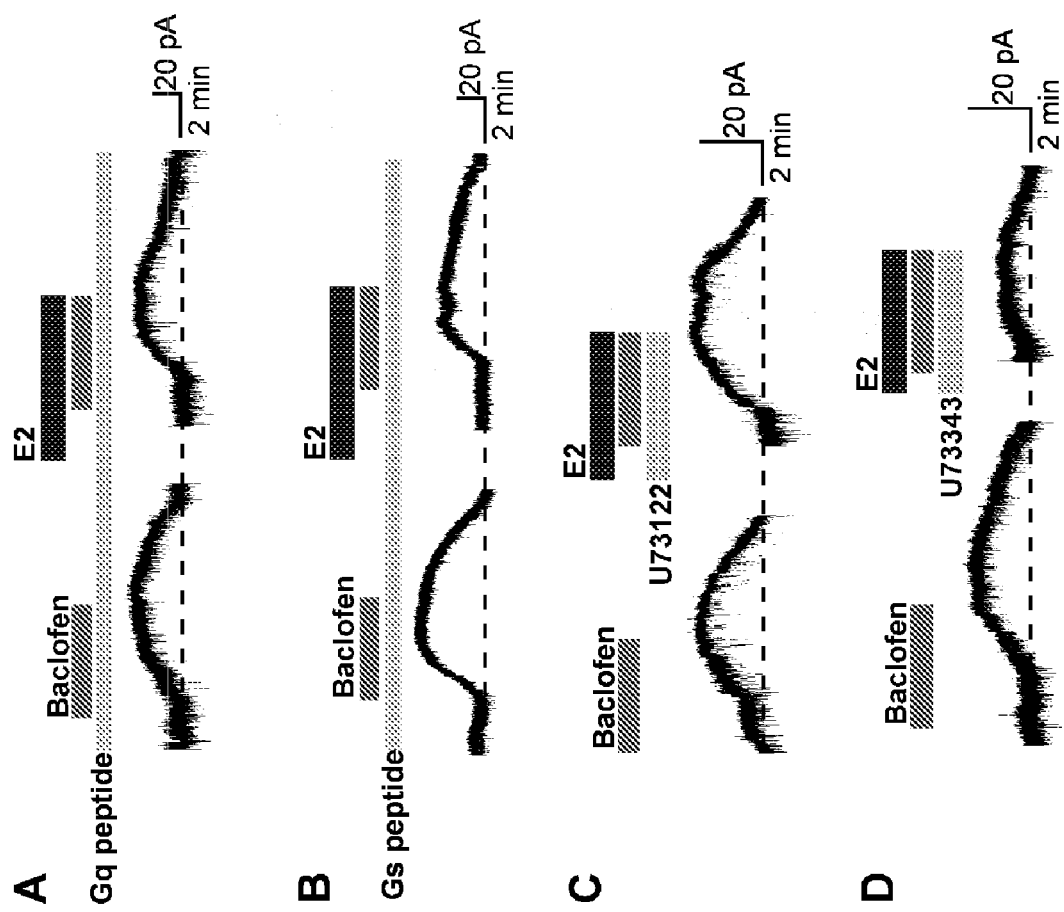
FIG. 12 includes representative traces of the baclofen responses in the presence of phospholipase C (PLC) and $Gα_q$ inhibitors.
Figure 13:
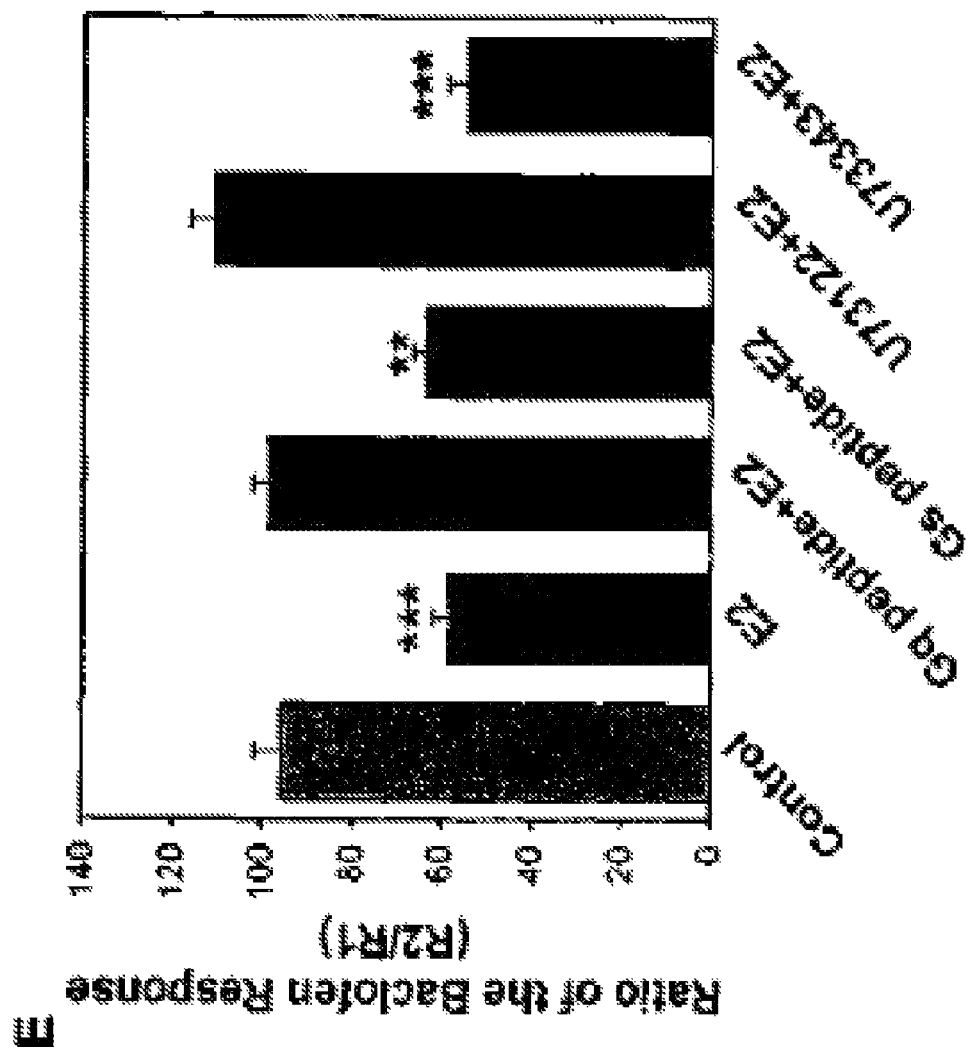
FIG. 13 is a bar graph summarizing the effects of the PLC and $Gα_q$ inhibitors.

Inhibition of the $GABA_B$ Response by 17β-Estradiol involves $G\alpha_q$:

Additional results demonstrate that the inhibition of the baclofen induced $GABA_B$ response by 17β-estradiol involves the messenger protein $G\alpha_q$. Although the specific PKC inhibitor BIS blocked the 17β-estradiol effect, forskolin (10 μM) was found to mimic the effects of estrogen in the presence of BIS blockade (FIG. 10 graph D and FIG. 11). Thus, the action of PKC is upstream of the activation of PKA. Indeed, the estrogen receptor-mediated inhibition of the $GABA_B$ response depended on the activation of $G\alpha_q$, as indicated by treating arcuate neurons with a peptide (11 amino acids) that mimics the C-terminal binding site of $G\alpha_q$ (Akhter et al., *Science* 280: 574-577,1998.). This peptide blocks the interaction between G protein coupled receptors and $G\alpha_q$ proteins. In cells dialyzed with this peptide (200 μM), the 17β-estradiol-mediated reduction of the $GABA_B$ response was significantly blocked (FIG. 12 graph A and FIG. 13) when compared to cells dialyzed with a control peptide (11 amino acids) that mimics the C-terminal domain of $G\alpha_s$ (FIG. 12 graph B and FIG. 13). Therefore, $G\alpha_q$ plays a primary role in 17β-estradiol-mediated rapid inhibition.

Moreover, the activation of phospholipase C(PLC), a well known $G\alpha_q$ effector, also plays a role. Indeed, the activation of PLCβ is required for the estrogen-induced inhibition of $GABA_B$ response as indicated by the treatment of neurons with the broad spectrum PLC inhibitor U73122 (10 μM). When U73122 (10 μM) was perfused in the extracellular-bathing media, the estrogen-mediated reduction of $GABA_B$ response was blocked (FIG. 12 graph C and FIG. 13), however the less active PLC inhibitor U73343 at the same concentration had no effect (FIG. 12 graph D and FIG. 13). With reference to FIG. 13, Bars represent the mean±S.E.M. of 4-11 cells tested per group (* $p<0.005$,  $p<0.01$ versus vehicle-control; U73122+17β-estradiol versus U73343+17β-estradiol, $p<0.05$; Gq peptide+17β-estradiol versus Gs peptide+17β-estradiol, $p<0.05$).

The Attenuation of the $GABA_B$ Response does not Involve Mitogen Activated Protein (MAP) Kinase:

Inhibition of MAP kinase activity does not prevent estrogen modulation of the baclofen response. Recent studies have shown that 17β-estradiol rapidly activates the MAP kinase pathway in primary neuronal cortical cultures and in organotypic cerebrocortical explant cultures (Watters et al., *Endocrinology* 138: 4030-4033, 1997; Singh et al., *J Neurosci* 19: 1179-1188, 1999; Singh et al., *J Neurosci* 20: 1694-1700, 2000). However, treatment with MAP kinases inhibitors PD98059 (10 μM, in the pipette) or U0126 (5 μM), did not affect 17β-estradiol inhibition of baclofen responses (R2/R1 for 17β-estradiol: 58.6±3.4%, n=10; versus PD98059+17β-estradiol: 66.1±11.8%, n=5).

Figures 14A, 14B:
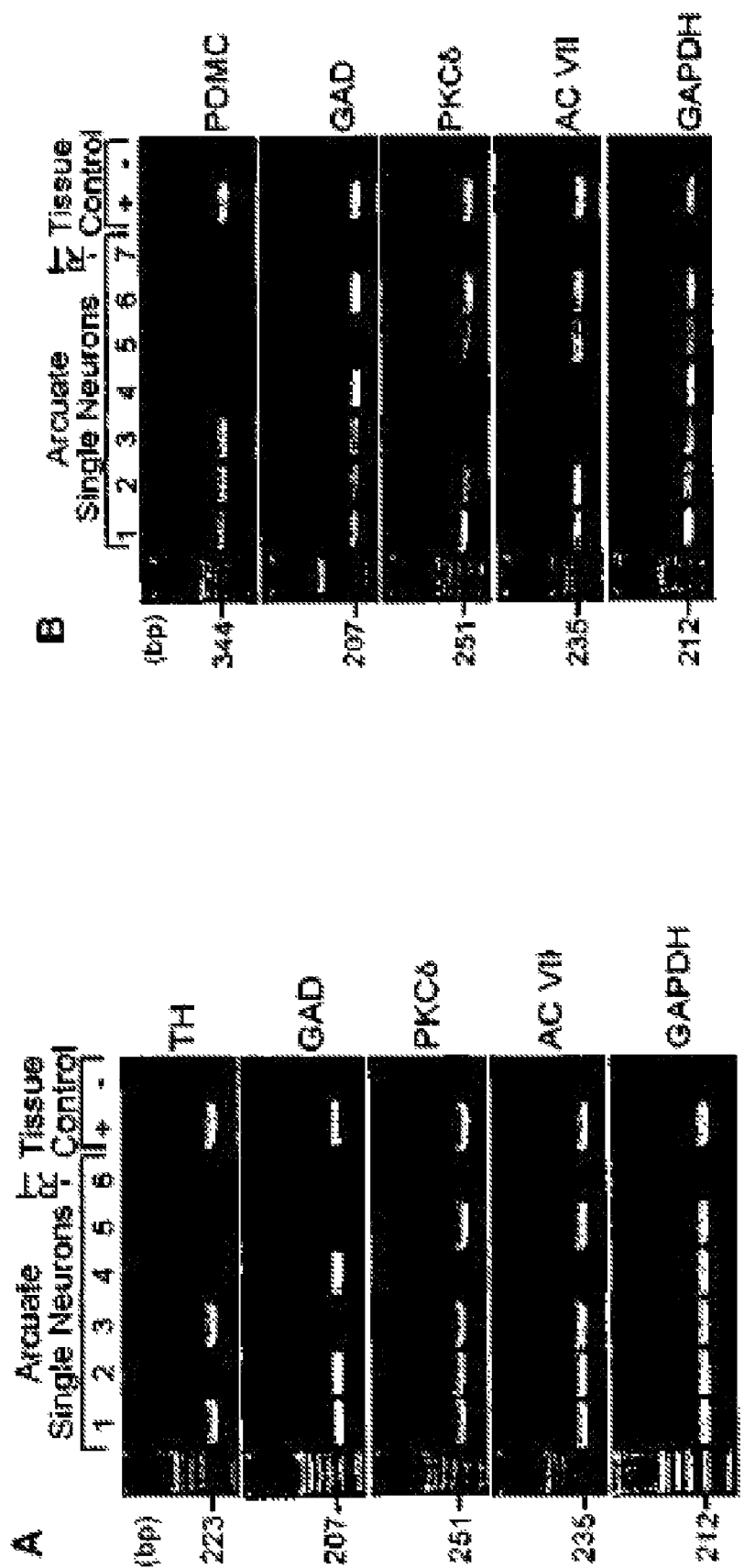
FIG. 14A is a representative gel illustrating that single arcuate neurons express mRNA for TH, GAD, PKCδ, AC VII and GAPDH.
FIG. 14B is a representative gel illustrating that single arcuate neurons express mRNA for POMC, GAD, PKCδ, AC VII and GAPDH.

Expression of $GABA_B$ receptor, PKCδ and Adenylate Cyclase VII Transcripts in Arcuate (GABA, Dopamine and POMC) Neurons:

The expression of $GABA_B$ receptor, PKCδ and adenylate cyclase VII transcripts in arcuate neurons was determined using single-cell RT-PCR from seventy-five acutely dispersed arcuate neurons. The results demonstrated that 90% of the neurons expressed $GAD_{65}$ transcripts including TH-expressing and POMC-expressing neurons (data not shown). Most importantly, 92% of the neurons expressed $GABA_B$ R2 transcripts, which correlates with the 90% response rate to baclofen. Furthermore, single cell RT-PCR results demonstrate that dopamine and POMC neurons express PKCδ and adenylyl cyclase VII transcripts. In one group of cells (n=22), PKCδ and adenylyl cyclase VII transcripts were expressed in the majority (70%) of TH neurons (FIG. 14A), including those that co-express $GAD_{65}$. TH and GAD were co-localized in 60% of this population of neurons. Due to limited amount of cDNA from individual neurons, POMC expression was determined in another group of cells (n=29), demonstrating that PKCδ and adenylyl cyclase VII transcripts were expressed in the majority (75%) of POMC neurons, including those that co-express $GAD_{65}$ (FIG. 14B). POMC and GAD were co-localized in 28% of this population of neurons. Therefore, the single cell RT-PCR data confirm the electrophysiological findings that dopamine and POMC neurons express the critical transcripts for rapid estrogen signaling. GAPDH transcripts were analyzed in the same cells as an internal control for the reverse transcriptase (RT) reaction. One cell contained no RT as a negative control (—RT). Basal hypothalamic tissue RNA was also reverse transcribed in the presence of RT (tissue controls, +). A tissue control without RT (−) was included in each trial. In addition, the following controls were included: Hank's balanced salt solution (HBSS) from the dispersed cellular milieu and a water blank, both of which were negative following RT-PCR (data not shown).

A Unique Membrane Estrogen Receptor Mediates the Rapid Effects of 17β-Estradiol:

The foregoing results demonstrate that a membrane estrogen receptor has been identified. For example, estrogen suppresses the action of the $GABA_B$ receptor agonist baclofen to activate GIRK channels in GABA, POMC, and dopamine neurons. This 17β-estradiol effect is rapid, with measurable suppression occurring within minutes after addition of 17β-estradiol. The kinetics of this response indicates mediation of the response by a membrane 17β-estradiol receptor instead of one of the classical nuclear estrogen receptors (ER)α or (ER)β, which operate by transcription regulation.

The pharmacology observed for this rapid estrogen response further supports the involvement of a novel transmembrane estrogen receptor. The membrane impermeable 17β-estradiol-BSA conjugate gives an identical response to free 17β-estradiol, as would be expected for a membrane associated receptor wherein the hormone-binding site of the receptor is accessible from the extracellular surface of the plasma membrane. The 17β-estradiol response is stereospecific with respect to the configuration of the D-ring hydroxyl group; 17β-estradiol elicits the rapid response whereas 17α-estradiol is inactive. This is notable because 17α-estradiol functions as an agonist of the nuclear estrogen receptors, albeit with slightly reduced potency compared to 17β-estradiol (Barkhem et al., *Mol Pharm* 54: 105-112, 1998.). The SERMs 4-OH tamoxifen, raloxifene, and GW-5638 all behave like 17β-estradiol in mediating this response whereas the steroidal antiestrogen ICI-182,780 antagonizes the 17β-estradiol response. Most importantly, the novel SERM 8 that is devoid of estrogen (or antiestrogen) activity with the nuclear estrogen receptors is a stronger activator of this rapid 17β-estradiol response than 17β-estradiol even at a 10-fold lower concentration. Moreover, this membrane ER has a subnanomolar affinity for estrogen as indicated by pharmacological (Schild) analysis (Lagrange et al., 1997). These results demonstrate that the pharmacology of this rapid response is different, and in the case of 8, separable from that of the nuclear estrogen receptors (Razandi et al., *Mol Endo* 13: 307-319, 1999; Levin, *J Appl Physiol* 91: 1860-1867, 2001; Chambliss et al., *Endocr Rev* 23: 665-686, 2002.).

Recently, Toran-Allerand and colleagues (Toran-Allerand et al., *J Neurosci* 22: 8391-8401, 2002) have identified a high affinity, saturable estrogen receptor, "ERX," that is associated with cavelor-like microdomains in developing neocortical neurons. This membrane-associated receptor is coupled to the activation of mitogen-activated protein kinases (MAPKs), extracellular-signal related kinase (ERK)1 and ERK2, which appear to be important for the development and survival of neurons (Watters et al., *Endocrinology* 138: 4030-4033, 1997; Singh et al., *J Neurosci* 19: 1179-1188, 1999; Singh et al., *J Neurosci* 20: 1694-1700, 2000; Ferin et al., *Recent Prog Horm Res* 40: 441-485, 1984.). ERX also has a distinct pharmacology in that 17α-estradiol is equipotent as 17β-estradiol in activating the MAP kinase pathway (Toran-Allerand et al., *J Neurosci* 22: 8391-8401, 2002; Wade et al., *Endocrinology* 142: 2336-2342, 2001). However, as demonstrated herein no effects were observed for 17α-estradiol on the $GABA_B$ response, or the μ-opioid response, which is coupled to the same family of GIRK channels in hypothalamic neurons (Lagrange et al., 1997). Similarly, Gu and Moss (Gu et al., *J Neurosci* 16: 3620-3629, 1996.) found that 17α-estradiol did not mimic the actions of 17β-estradiol in the hippocampus to potentiate the glutamate (kainate)-mediated currents in CA1 pyramidal neurons. Likewise, Mermelstein et al., *J Neurosci* 16: 595-604, 1996, found that 17α-estradiol was much less efficacious than 17β-estradiol in reducing L-type calcium currents in neostriatal neurons. Therefore, the membrane estrogen receptor that modulates channel activity in neurons via the PKC-PKA pathway is pharmacologically distinct from the receptor that is coupled to activation of ERK1/2 that promotes growth and survival.

Figure 15:
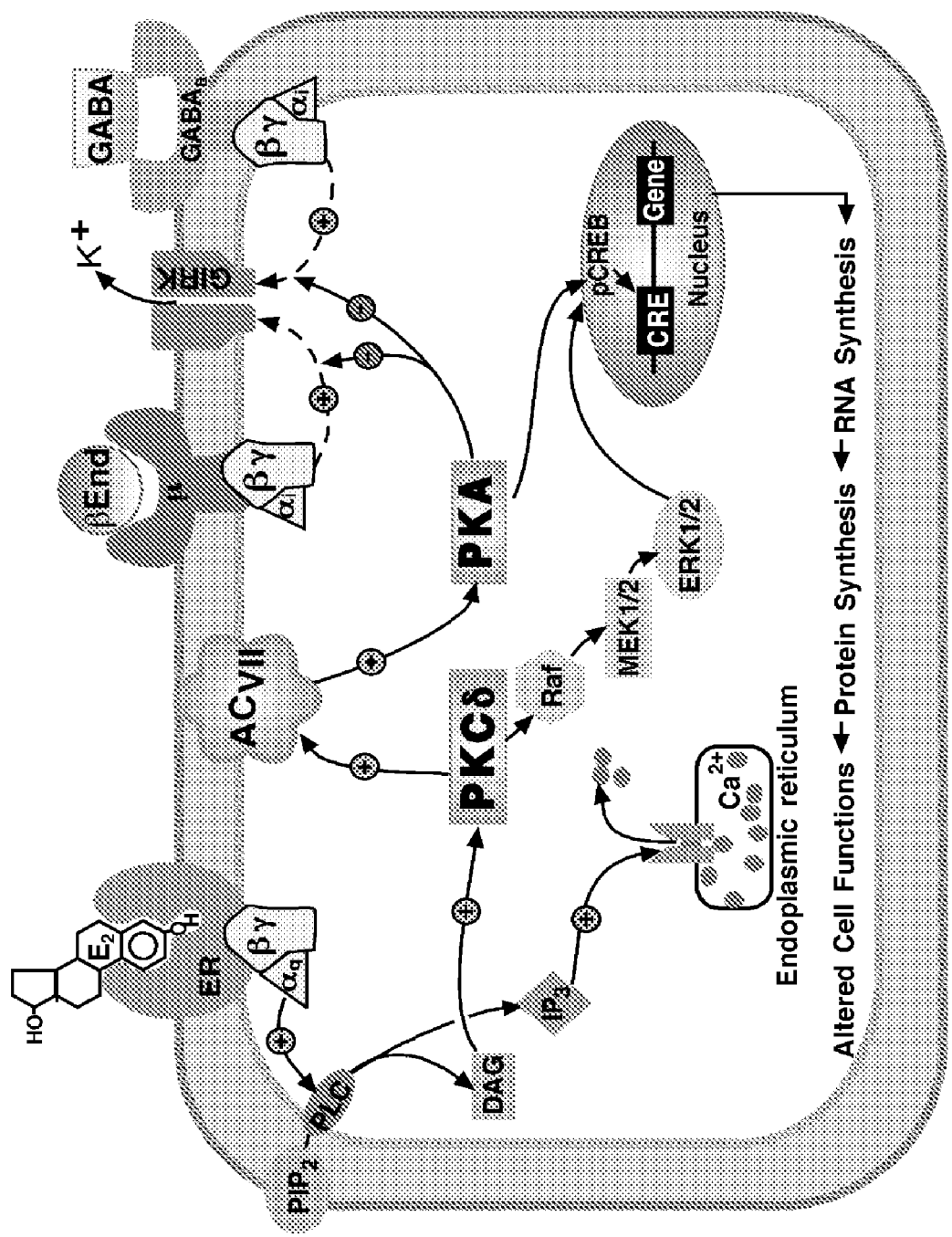
FIG. 15 is a schematic overview showing the rapid versus delayed estrogen receptor mediated modulation of neurotransmitter regulated, G protein-coupled receptors via a membrane-associated estrogen receptor in hypothalamic neurons.

17β-Estradiol Activates PKCδ and PKA to Alter the Coupling of GPCRs to $K^+$ Channels in Hypothalamic Neurons:

The data detailed herein demonstrate that the signal transduction pathway for the rapid response to estrogen in hypothalamic neurons follows that depicted in FIG. 15. With reference to FIG. 15, the sequence of events are: (1) 17β-estradiol binds to a novel transmembrane estrogen receptor; (2) ligand binding activates $G\alpha_q$; (3) activated $G\alpha_q$ in turn activates PLC; (4) activated PLC liberates DAG; (5) free DAG stimulates PKCδ; (6) PKCδ activates adenylyl cyclase (VII); (7) cAMP levels are elevated; (8) cAMP stimulates PKA; (9) PKA phosphorylates membrane targets critical for $K^+$ channel function.

Further support for the pathway shown in FIG. 15 is found in that protein kinase pathways affect $GABA_B$ receptor-mediated signaling in CNS neurons. Activation of protein kinase C suppresses the $GABA_B$ receptor-activation of GIRK channels in the hippocampal CA1 pyramidal neurons (Dutar et al., *Neuron* 1: 585-591, 1988.) and attenuates the $GABA_B$ receptor-mediated inhibition of norepinephrine release from cerebellar slices (Taniyama et al., *J Neurochem* 58: 1239-1245, 1992).

Currently, there are 12 known members of the PKC family (Way et al., *Trends Pharmacol Sci* 21: 181-187, 2000). The family is divided into three groups based on sequence homology and biochemical regulation. Class A, or conventional PKCs (PKCα, βI, βII and γ) are the well-known, $Ca^{2+}$-dependent PKCs. Class B, or novel PKCs (PKCδ, ε, θ and η), are $Ca^{2+}$ independent. Finally, Class C PKCs, or atypical PKCs (PKCζ and τ/λ), are the most divergent class. Atypical PKCs are also $Ca^{2+}$ independent and do not require diacylglycerol for activation (Way et al., *Trends Pharmacol Sci* 21: 181-187, 2000). The rapid, $GABA_B$ suppressing effects of estrogen in hypothalamic neurons were sensitive to the broad spectrum PKC inhibitor BIS, but not to Gö6976, implicating the involvement of a PKC not belonging to the conventional PKC class. In addition, estrogen's inhibition of the $GABA_B$ response was not altered by inclusion of 10 mM BAPTA in the intracellular recording patch pipette, providing confirming that the $Ca^{2+}$ dependent, conventional PKCs are not involved. However, the selective PKCδ inhibitor rottlerin blocked the actions of 17β-estradiol suggesting that this novel class PKC is a mediator of the rapid 17β-estradiol response. Moreover, the scRT-PCR data on the expression of PKCδ transcripts in arcuate neurons described herein further implicate PKCδ in the 17β-estradiol-mediated inhibition of the $GABA_B$ response. Likewise, PKCδ is involved in the estrogen-mediated inhibition of $K^+$ channels and fluid retention in female distal colonic epithelial cells, although the upstream signaling pathway is not known (Doolan et al., 2000).

PKC Activation is Upstream of PKA Activation:

PKC activation in the 17β-estradiol mediated inhibition of the $GABA_B$ is upstream of PKA activation. For example, internal perfusion of BIS completely blocked the inhibition of the baclofen response by 17β-estradiol, but did not attenuate the inhibition of the baclofen response by forskolin applied via bath perfusion. PKC is known to activate adenylyl cyclases (Jacobowitz et al., *J Biol Chem* 268: 3829-3832, 1993; Yoshimura et al., *J Biol Chem* 268: 4604-4607, 1993; Lin et al., *Br J Pharmacol* 125: 1601-1609, 1998); moreover, when adenylyl cyclase (AC) is activated by PKC, instead of by $G\alpha_s$ or forskolin, it is resistant to inhibition by $G\alpha_i$ (Pieroni et al., *Curr Opin Neurobiol* 3: 345-351, 1993.). To date, nine AC isozymes have been cloned (AC types I-IX). Notably, AC VII has a potential binding site for PKCδ that is not present in the sequences of the other adenylyl cyclases, which would allow PKCδ to directly phosphorylate AC VII (Nelson et al., *J Biol Chem* 278: 4552-4560, 2003.). GABA neurons in the cortex, hippocampus, striatum and cerebellum are immunoreactive for AC VII (Mons et al., *Brain Res* 788: 251-261, 1998.), and, as disclosed herein, hypothalamic GABA, TH and POMC neurons express AC VII transcripts.

$G\alpha_q$ Mediates the Inhibition of the $GABA_B$ Response by 17β-Estradiol Through PLC:

The results described herein show that a membrane ER is specifically coupled to the messenger $G\alpha_q$, and that this messenger protein is involved in the inhibition of the $GABA_B$ response by 17β-estradiol. This conclusion is confirmed by results observed when intracellular dialysis with a peptide fragment of $G\alpha_q$ blocked the receptor interaction with G protein. This $G\alpha_q$ peptide has been used to block $G\alpha_q$ signaling pathways in cortical pyramidal neurons (Carr et al., *J Neurosci* 22: 6846-6855, 2002.). In addition, the estrogen-mediated reduction of the $GABA_B$ response was significantly reduced by the phospholipase C inhibitor U73122 compared to cells perfused with the less active inhibitor U73343. Thus, the messenger $G\alpha_q$ is involved in the inhibition of the $GABA_B$ response by 17β-estradiol.

Most PKCs are activated by diacylglycerol and some require the presence of $Ca^{2+}$. Thus, PKCs are downstream of the phospholipase C(PLC)-inositol triphosphate/diacylglycerol signaling cascade. Because different forms of PLC can be activated by various messengers including $G\alpha_q$, $G\beta\gamma$ (PLCβ), and tyrosine kinases (PLCγ), the PKC family is involved in a diverse array of signaling cascades (Tanaka et al., *Annu Rev Neurosci* 17: 551-567, 1994; Battaini et al., *Pharmacol Res* 44: 353-361, 2001.).

EXAMPLE 23

This example describes the identification of estrogen receptor antagonists and the determination of antagonist potency using Schild analysis. The general protocol for this analysis is disclosed by Lagrange et al., 1997. Cumulative concentration-response curves are generated by applying increasing concentrations of the selective estrogen receptor agonist, compound 8, in the whole cell electrophysiological assay described above. Increasing concentrations of baclofen are applied until the drug-induced outward current reaches a new steady level. The $EC_{50}$ values for both baclofen and compound 8 are calculated using SigmaPlot (Jandel Scientific, Costa Madre, Calif.) software to determine the best fit to the logistic equation. Cells are then superfused with 1 nM solution of the potential estrogen receptor antagonist. Increasing concentrations of compound 8 (as applied in generating the initial concentration-response curve above) are then applied to generate a second response curve. The cells are then treated with a 2 nm solution of the potential antagonist and the concentration response curve repeated. This process is repeated with increasing concentrations of the potential antagonist to generate multiple concentration response curves. Linear regression fit of the data {log(Dose Ratio-1) versus-log [antagonist concentration]} yields a slope of −1.0 when compound 8 and the proposed antagonist bind to the previously unidentified membrane associated estrogen receptor disclosed herein.

EXAMPLE 24

This example describes the evaluation of the cardioprotective activity of the disclosed compounds and provides a method for identifying novel cardioprotective selective estrogen receptor modulators. Apolipoprotein E-deficient C57/B1J (apo E KO) mice (available from Taconic Farms), 4-7 weeks of age, are ovariectomized. The animals are randomized by weight into groups (n=12-15 mice per group). The mice are treated with the disclosed compound or 17β-estradiol sulfate (at 1 mg/kg/day) in the diet using a protocol wherein the amount of consumed is measured weekly, and the dose adjusted accordingly, based on animal weight. The diet used is a Western-style diet (57U5) that is prepared by Purina and contains 0.50% cholesterol, 20% lard and 25 IU/KG Vitamin E. The mice are dosed/fed using this paradigm for a period of 12 weeks. Control animals are fed the Western-style diet and receive no compound. At the end of the study period, the animals are euthanized and plasma samples obtained. The hearts are perfused in situ, first with saline and then with neutral buffered 10% formalin solution.

Total cholesterol and triglycerides are determined using enzymatic methods with commercially available kits from Boehringer Mannheim and Wako Biochemicals, respectively. Separation and quantification of plasma lipoproteins are performed, and each lipoprotein fraction is quantified by multiplying the total cholesterol value by the relative percent area of each respective chromatogram peak.

Aortic atherosclerosis is quantified by carefully isolating the aortas and placing the vessels in formalin fixative for 48-72 h before handling. Atherosclerotic lesions are identified using Oil Red O staining. The vessels are briefly destained, and then imaged. The lesions are quantified en face along the aortic arch and lesion assessment is performed on the vessels, specifically on the region contained within the aortic arch from the proximal edge of the brachio-cephalic trunk to the distal edge of the left subclavian artery. Aortic atherosclerosis data can be expressed as percent lesion involvement strictly within this defined luminal area.

EXAMPLE 25

This example describes the evaluation of prophylactic neuroprotection using the disclosed compounds in response to oxygen deprivation/reperfusion, and provides a method for identifying novel neuroprotective selective estrogen receptor modulators. Female Mongolian gerbils (available from, for example, Charles River Laboratories, Kingston, N.Y.) after acclimation, are anesthetized with isoflurane and ovariectomized (day 0). Beginning the following morning (day 1), gerbils are treated subcutaneously with either vehicle (10% EtOH/corn oil), 17β-estradiol (1 mg/kg, sc) or a compound disclosed herein. Prior to day 6, the gerbils are fasted overnight (to facilitate consistent ischemic injury) and then subjected to global ischemia surgery. The surgery proceeds by anesthetizing the gerbils with isoflurane, visualizing the common carotid arteries via a mid-line neck incision and simultaneously occluding both arteries for 5 minutes with microaneurysm clips. Following occlusion, the clips are removed to allow cerebral reperfusion and the neck incision is closed with wound clips. On day 12, gerbils are exposed to a lethal dose of $CO_2$, the brains frozen on dry ice and stored at $-80°$ C.

The degree of neuronal protection is evaluated by in situ hybridization analysis of neurogranin mRNA. Briefly, 20 µM coronal cryostat sections are collected on gelatin-coated slides, dried and stored at $-80°$ C. At the time of processing, the desiccated slide boxes are warmed to room temperature, the slides postfixed in 4% paraformaldehyde, treated with acetic anhydride and then delipidated and dehydrated with chloroform and ethanol. Processed section-mounted slides are then hybridized with 200 µL ($6×10^6$ DPM/slide) of an antisense or sense (control) riboprobe for Neurogranin ($^{35}$S-UTP-labeled NG-241; bases 99-340) in a 50% formamide hybridization mix and incubated overnight at 55° C. in a humidified slide chamber without coverslipping. The following morning, the slides are collected in racks, immersed in 2×SSC (0.3 M NaCl, 0.03 M sodium citrate; pH 7.0)/10 mM DTT, treated with RNase A (20 µg/ml) and washed (2×30 min) at 67° C. in 0.1×SSC to remove nonspecific label. After dehydration, the slides are opposed to BioMax (BMR-1; Kodak) X-ray film overnight.

The level of neurogranin hybridization signal is used to quantitatively assess the degree of neuronal loss in the CA1 region after injury and to evaluate the efficacy of 17β-estradiol and the disclosed compounds. Neurogranin mRNA is selected for these studies because it is highly expressed in the hippocampal neurons including CA1, but absent in glia and other cell types present in this brain region. Therefore, measurement of the amount of neurogranin mRNA present represents surviving neurons. Relative optical density measurements of neurogranin hybridization signal are obtained from film autoradiograms with a computer based image analysis system (C-Imaging Inc., Pittsburgh, Pa.). The results from 6 sections (40 µm apart) per animal are averaged and statistically evaluated. Numerical values are reported as the mean±S.E.M. One-way analysis of variance is used to test for differences in the level of neurogranin mRNA and all statements of non-difference in the results section imply that $p>0.05$.

EXAMPLE 26

This example describes the evaluation of cognition enhancement achieved using the disclosed compounds. Ovariectomized rats (n=50) are habituated to an 8-arm radial arm maze for 10-min periods on each of 5 consecutive days. Animals are water-deprived prior to habituation and testing. A 100 µL aliquot of water placed at the ends of each arm serves as reinforcement. Acquisition of a win-shift task in the radial arm maze is accomplished by allowing the animal to have access to one baited arm. After drinking, the animal exits the arm and re-enters the central compartment, where it now has access to the previously visited arm or to a novel arm. A correct response is recorded when the animal chooses to enter a novel arm. Each animal is given 5 trials per day for 3 days. After the last acquisition trial, the animals are assigned to one of the following 4 groups: (1) Negative controls: injected with 10% DMSO/sesame oil vehicle once daily for 6 days (1 µg/kg, subcutaneous). (2) Positive controls: injected with 17β-estradiol benzoate for 2 days and tested 4 days after the second injection (17β-estradiol benzoate at 10 µg/0.1 mL per rat). (3) 17β-estradiol will be injected daily for 6 days (20 µg/kg, subcutaneous). (4) Test compound: injected daily for 6 days (doses may vary). All injections will begin after testing on the last day of acquisition. The last injection for groups 1, 3, and 4 will take place 2 h before testing for working memory.

The test for working memory is a delayed non-matching-to-sample task (DNMS) utilizing delays of 15, 30, or 60 seconds. This task is a variation of the acquisition task in which the rat is placed in the central arena and allowed to enter one arm as before. A second arm is opened once the rat traverses halfway down the first arm, and again the rat is required to choose this arm. When it has traveled halfway down this second arm, both doors are closed and the delay is instituted. Once the delay has expired, both of the original two doors, and a third novel door, are opened simultaneously. A correct response is recorded when the animal travels halfway down the third, novel arm. An incorrect response is recorded when the animal travels halfway down either the first or second arms. Each animal will receive 5 trials at each of the three delay intervals for a total of 15 trials per subject.

It will be apparent to those skilled in the art that various modifications and variations can be made in the present compounds, compositions and methods without departing from the scope or spirit of the disclosure. Other embodiments of the compounds, compositions and methods will be apparent to those skilled in the art from consideration of the specification and practice of the procedures disclosed herein. It is intended that the specification and examples be considered as exemplary only, with a true scope and spirit of the invention being indicated by the following claims.

What is claimed is:

1. A compound according to the formula:

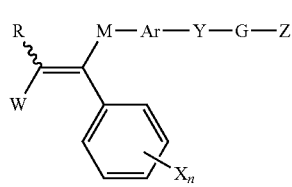

or a pharmaceutically acceptable salt thereof, wherein

R is aryl, cycloalkyl, or phenyl (optionally substituted with a hydroxy or a lower aliphatic group);

W is naphthyl (optionally substituted with hydroxy, halogen, or lower alkyl);

M is a carbonyl, —(C=O)NR$_1$—, or —(C=S)NR$_1$—;

Ar is an aromatic group;

X is independently, at each occurrence, hydrogen, hydroxy, alkoxy, or halogen, wherein n=1-2;

Y is —O—, —NR$_2$—, or —S—;

G is a linker group;

Z is hydroxy, boronate, sulfate, sulfonate, phosphate, phosphonate, carboxy, amino, dimethylamino, piperidino or a charged group;

R$_1$ is hydrogen, lower alkyl or aralkyl; and

R$_2$ is hydrogen or lower alkyl.

2. The compound according to claim 1, wherein the compound has the formula

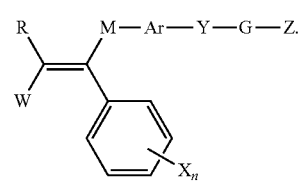

3. The compound according to claim 1, wherein the compound has the formula

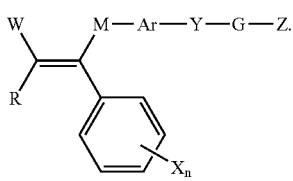

4. The compound according to claim 1, wherein Ar is a phenylenyl group.

5. The compound according to claim 1, wherein M is —(C=O)NH—.

6. The compound according to claim 1, wherein G is a lower alkylenyl group.

7. The compound according to claim 1, wherein Z is —COO, or —NR$_2$R$_3$R$_4^+$, wherein R$_2$, R$_3$, and R$_4$ are each, independently, H, methyl, or ethyl.

8. The compound according to claim 1, wherein Y is oxygen and -G-Z has a formula selected from the group consisting of:

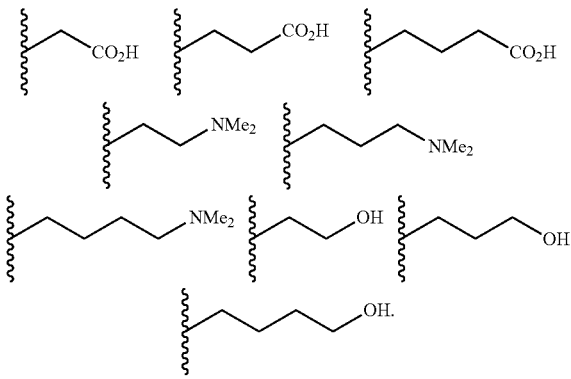

9. The compound according to claim 1, wherein X is independently, one or more of hydroxy or fluoride.

10. The compound according to claim 1 wherein R is phenyl optionally substituted with hydroxyl or cycloalkyl.

11. A compound according to the formula:

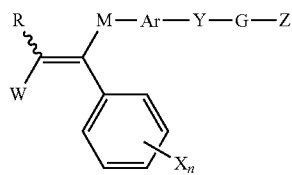

or a pharmaceutically acceptable salt thereof,
wherein
R is H or a lower alkyl;
W is naphthyl (optionally substituted with hydroxy, halogen, or lower alkyl);
M is a carbonyl, —(C=O)NR$_1$—, or —(C=S)NR$_1$—;
Ar is an aromatic group;
X is independently at each occurrence, hydroxy, alkoxy, or halogen, wherein n=1-2;
Y is —O—, —NR$_2$—, or —S—;
G is a linker group;
Z is hydroxyl, boronate, sulfate, sulfonate, phosphate, phosphonate, carboxy, amino, dimethylamino, piperidino or a charged group;
R$_1$ is hydrogen, lower alkyl or aralkyl; and
R$_2$ is hydrogen or lower alkyl.

12. The compound according to claim 11, wherein the compound has the formula:

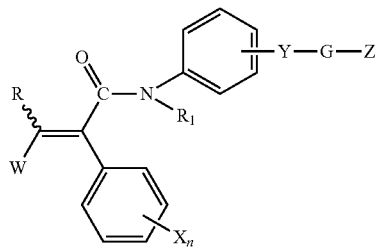

wherein R$_1$ is hydrogen, a lower alkyl or an aralkyl group.

13. The compound according to claim 11, wherein Ar is a phenylenyl group.

14. The compound according to claim 11, wherein M is —(C=O)NH—.

15. The compound according to claim 11, wherein G is a lower alkylenyl group.

16. The compound according to claim 11, wherein Z is —COO, or —NR$_2$R$_3$R$_4^+$, wherein R$_2$, R$_3$, and R$_4$ are each, independently, H, methyl, or ethyl.

17. The compound according to claim 11, wherein Y is oxygen and -G-Z has a formula selected from the group consisting of:

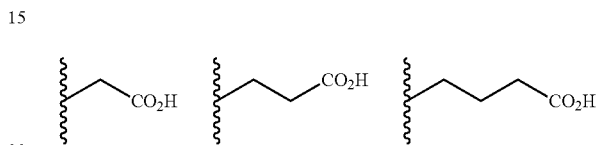

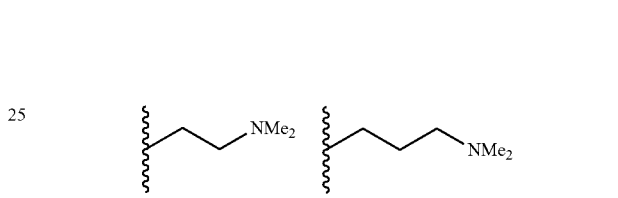

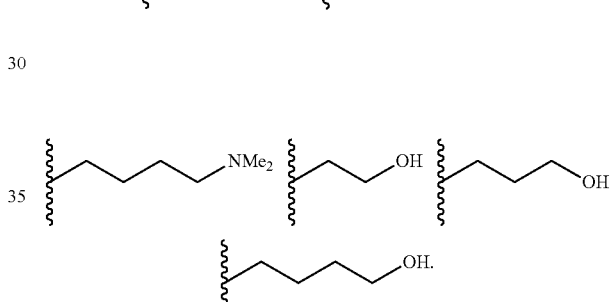

18. The compound according to claim 11, wherein X is independently, one or more of hydroxy or fluoride.

19. The compound according to claim 11 wherein W is naphthyl optionally substituted with hydroxyl or fluoride.

20. The compound according to claim 11 wherein the compound has the formula:

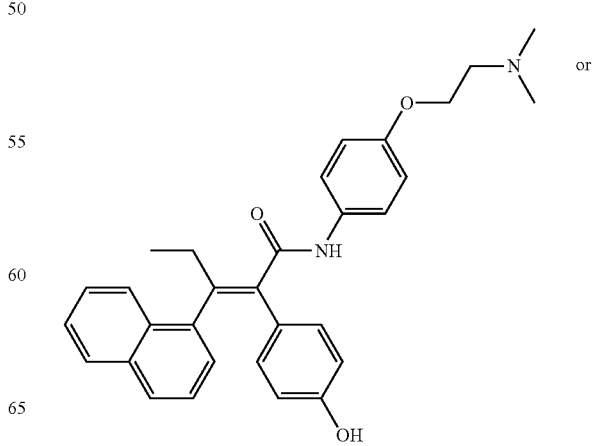

-continued

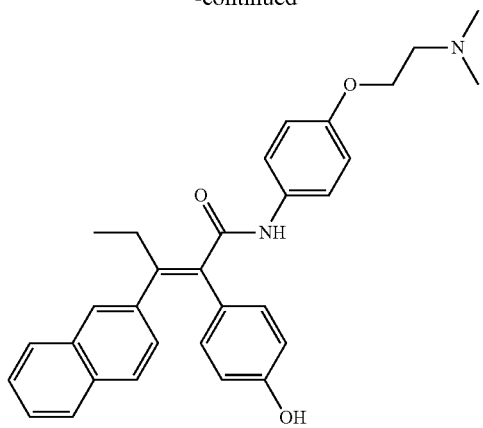

21. A compound according to the formula:

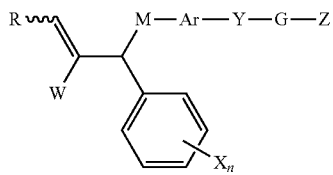

or a pharmaceutically acceptable salt thereof,
wherein R is hydrogen or a lower alkyl;
W is naphthyl (optionally substituted with hydroxy, halogen, or lower alkyl);
M is a carbonyl, $—(C=O)NR_1—$, or $—(C=S)NR_1—$;
Ar is an aromatic group;
X is independently at each occurrence, hydroxy, alkoxy, or halogen, wherein n=1-2;
Y is $—O—$, $—NR_1—$, or $—S—$;
G is a linker group;
Z is a carboxyl, hydroxy or amino group, wherein the amino group is optionally substituted with an alkyl; and
$R_1$ is hydrogen or lower alkyl.

22. The compound according to claim 21, wherein Ar is a phenylenyl group.

23. The compound according to claim 21, wherein M is $—(C=O)NH—$.

24. The compound according to claim 21, wherein G is a lower alkylenyl group.

25. The compound according to claim 21, wherein Z is $—COO$, or $—NR_2R_3R_4^+$, wherein $R_2$, $R_3$, and $R_4$ are each, independently, H, methyl, or ethyl.

26. The compound according to claim 21, wherein Y is oxygen and -G-Z has a formula selected from the group consisting of:

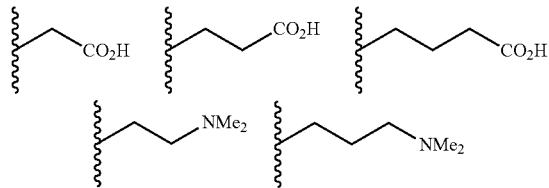

-continued

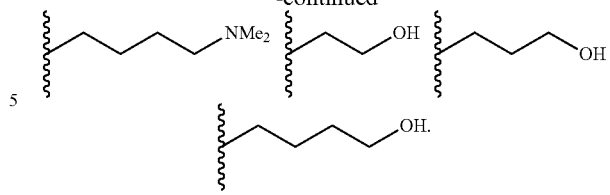

27. A compound according to the formula:

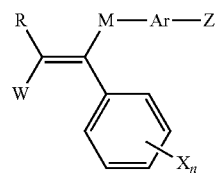

or a pharmaceutically acceptable salt thereof,
wherein R is aryl, cycloalkyl, lower alkyl, phenyl optionally substituted with hydroxyl or lower aliphatic group;
W is naphthyl (optionally substituted with H, hydroxyl, halogen, or methyl);
M is a carbonyl, $—(C=O)NR_1—$, or $—(C=S)NR_1—$;
Ar is an aromatic group;
X is independently at each occurrence, hydroxy, alkoxy, or halogen, wherein n=1-2;
G is a linker group; and
Z is hydroxy.

28. The compound according to claim 27, wherein Ar is a phenylenyl group.

29. The compound according to claim 27, wherein M is $—(C=O)NH—$.

30. The compound according to claim 28, wherein Z is $—OH$.

31. A compound according to the formula:

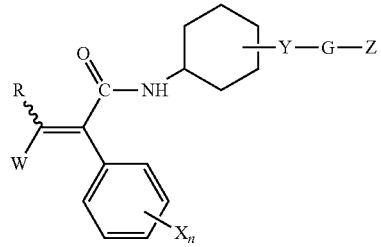

or a pharmaceutically acceptable salt thereof,
wherein R is aryl, cycloalkyl, lower alkyl, phenyl optionally substituted with hydroxy or a lower aliphatic group;
W is naphthyl (optionally substituted with hydroxy, halogen, or lower alkyl);
X is independently at each occurrence, hydroxy, alkoxy, or halogen, wherein n=1-2;
Y is $—O—$, $—NR_1—$, or $—S—$;
G is a linker group;
Z is a carboxyl, hydroxy or amino group, wherein the amino group is optionally substituted with an alkyl; and
$R_1$ is hydrogen or lower alkyl.

32. The compound according to claim 31, wherein G is a lower alkylenyl group.

33. The compound according to claim 31, wherein Z is $—COO$, or $—NR_2R_3R_4^+$, wherein $R_2$, $R_3$, and $R_4$ are each, independently, H, methyl, or ethyl.

34. The compound according to claim 31, wherein Y is oxygen and -G-Z has a formula selected from the group consisting of:
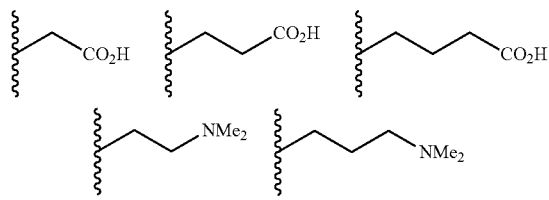
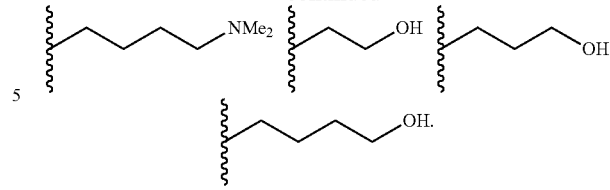
35. A composition, comprising a pharmaceutically effective amount of a compound of claim 1, 11, 21, 27 or 31.
* * * * *